(12) United States Patent
Moon

(10) Patent No.: US 10,278,645 B2
(45) Date of Patent: May 7, 2019

(54) BODY-WORN VITAL SIGN MONITOR

(75) Inventor: Jim Moon, Porland, OR (US)

(73) Assignee: SOTERA WIRELESS, INC., San Diego, CA (US)

( * ) Notice: Subject to any disclaimer, the term of this patent is extended or adjusted under 35 U.S.C. 154(b) by 295 days.

(21) Appl. No.: 12/762,822

(22) Filed: Apr. 19, 2010

(65) Prior Publication Data

US 2011/0224508 A1 Sep. 15, 2011

Related U.S. Application Data

(60) Provisional application No. 61/312,624, filed on Mar. 10, 2010.

(51) Int. Cl.
*A61B 5/00* (2006.01)
*G06F 19/00* (2018.01)
*H04W 4/02* (2018.01)

(52) U.S. Cl.
CPC ............. *A61B 5/6824* (2013.01); *A61B 5/00* (2013.01); *A61B 5/0002* (2013.01); *G06F 19/00* (2013.01); *A61B 5/411* (2013.01); *A61B 5/746* (2013.01); *A61B 5/7465* (2013.01); *H04W 4/02* (2013.01)

(58) Field of Classification Search
CPC ....... A61B 5/0002; A61B 5/411; A61B 5/746; A61B 5/6824; H04W 4/02
See application file for complete search history.

(56) References Cited

U.S. PATENT DOCUMENTS

| 4,086,916 A | 5/1978 | Freeman et al. |
| 4,263,918 A | 4/1981 | Swearingen et al. |
| 4,270,547 A | 6/1981 | Steffen et al. |
| 4,305,400 A | 12/1981 | Logan |
| 4,577,639 A | 3/1986 | Simon et al. |
| 4,582,068 A | 4/1986 | Phillipps et al. |
| 4,653,498 A | 3/1987 | New, Jr. et al. |
| 4,710,164 A | 12/1987 | Levin et al. |

(Continued)

FOREIGN PATENT DOCUMENTS

| EP | 0443267 A1 | 8/1991 |
| GB | 2329250 A | 3/1999 |

(Continued)

OTHER PUBLICATIONS

"PDF-Pro for iPhone & iPod touch User Manual" Jul. 2009, < http://epapyrus.com/en/files/PDF-Pro%20User%20Manual(Eng).pdf > accessed on Apr. 20, 2012.*

(Continued)

*Primary Examiner* — Michael W Kahelin
*Assistant Examiner* — Shirley X Jian
(74) *Attorney, Agent, or Firm* — Acuity Law Group, PC; Michael A. Whittaker

(57) ABSTRACT

The invention provides a body-worn vital sign monitor that measures a patient's vital signs (e.g. blood pressure, SpO2, heart rate, respiratory rate, and temperature) while simultaneously characterizing their activity state (e.g. resting, walking, convulsing, falling) and posture (upright, supine). The monitor processes this information to minimize corruption of the vital signs and associated alarms/alerts by motion-related artifacts. It also features a graphical user interface (GUI) rendered on a touchpanel display that facilitates a number of features to simplify and improve patient monitoring and safety in both the hospital and home.

13 Claims, 28 Drawing Sheets

(56) References Cited

U.S. PATENT DOCUMENTS

| | | |
|---|---|---|
| 4,722,351 A | 2/1988 | Phillipps et al. |
| 4,802,486 A | 2/1989 | Goodman et al. |
| 4,807,638 A | 2/1989 | Sramek |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,224,928 A | 7/1993 | Sibalis et al. |
| 5,247,931 A | 9/1993 | Norwood |
| 5,289,824 A | 3/1994 | Mills et al. |
| 5,316,008 A | 5/1994 | Suga et al. |
| 5,339,818 A | 8/1994 | Baker et al. |
| 5,448,991 A | 9/1995 | Polson et al. |
| 5,465,082 A | 11/1995 | Chaco |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,575,284 A | 11/1996 | Athan et al. |
| 5,588,427 A | 12/1996 | Tien |
| 5,593,431 A | 1/1997 | Sheldon |
| 5,632,272 A | 5/1997 | Diab et al. |
| 5,645,060 A | 7/1997 | Yorkey |
| 5,649,543 A | 7/1997 | Hosaka et al. |
| 5,661,632 A * | 8/1997 | Register ............ 361/679.3 |
| 5,680,870 A | 10/1997 | Hood et al. |
| 5,685,299 A | 11/1997 | Diab et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | Delorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lichter et al. |
| 6,160,478 A | 12/2000 | Jacobsen et al. |
| 6,168,569 B1 | 1/2001 | McEwen et al. |
| 6,198,394 B1 * | 3/2001 | Jacobsen et al. ......... 340/573.1 |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 * | 7/2001 | Anderson et al. ......... 348/333.1 |
| 6,263,222 B1 | 7/2001 | Diab et al. |
| 6,287,262 B1 * | 9/2001 | Amano et al. ............. 600/500 |
| 6,334,065 B1 | 12/2001 | Al-Ali et al. |
| 6,371,921 B1 | 4/2002 | Caro et al. |
| 6,388,240 B2 | 5/2002 | Schulz et al. |
| RE37,852 E | 9/2002 | Aso et al. |
| 6,443,890 B1 | 9/2002 | Schulze et al. |
| 6,480,729 B2 | 11/2002 | Schulz et al. |
| 6,491,647 B1 | 12/2002 | Bridger et al. |
| 6,503,206 B1 | 1/2003 | Li et al. |
| 6,516,289 B2 | 2/2003 | David |
| 6,526,310 B1 | 2/2003 | Carter et al. |
| 6,527,729 B1 | 3/2003 | Turcott |
| 6,533,729 B1 | 3/2003 | Khair et al. |
| 6,541,756 B2 | 4/2003 | Schulz et al. |
| 6,544,173 B2 | 4/2003 | West et al. |
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,597,384 B1 * | 7/2003 | Harrison ............... 345/204 |
| 6,605,038 B1 | 8/2003 | Teller et al. |
| 6,606,993 B1 | 8/2003 | Wiesmann et al. |
| 6,616,606 B1 | 9/2003 | Petersen et al. |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 * | 9/2004 | Mault et al. ............ 600/300 |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,882,335 B2 * | 4/2005 | Saarinen ............ G06F 1/1605<br>345/156 |
| 6,893,396 B2 | 5/2005 | Schulze et al. |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 * | 1/2006 | Suzuki et al. .......... 340/539.12 |
| 6,997,882 B1 | 2/2006 | Parker et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,079,888 B2 | 7/2006 | Oung et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 * | 4/2008 | Suzuki et al. ............. 600/500 |
| 7,355,512 B1 | 4/2008 | Al-Ali |
| 7,373,191 B2 | 5/2008 | Delonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |

(56) References Cited

U.S. PATENT DOCUMENTS

| | | |
|---|---|---|
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,558,057 B1 * | 7/2009 | Naksen ............. G06F 1/1613 |
| | | 361/679.3 |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,102,458 B2 * | 1/2012 | Kaneda et al. ........... 348/333.01 |
| 8,137,270 B2 | 3/2012 | Keenan et al. |
| 8,167,800 B2 * | 5/2012 | Ouchi et al. .................. 600/301 |
| 8,810,512 B2 * | 8/2014 | Andersson ............ G06F 1/1626 |
| | | 345/158 |
| 9,436,767 B2 * | 9/2016 | Gordon ............. G06F 17/30867 |
| 2001/0004234 A1 | 6/2001 | Petelenz et al. |
| 2001/0011993 A1 * | 8/2001 | Saarinen .............. G06F 1/1605 |
| | | 345/156 |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0122469 A1 | 6/2006 | Martel |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 * | 11/2007 | Park et al. .................... 345/649 |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |

(56) References Cited

U.S. PATENT DOCUMENTS

| | | |
|---|---|---|
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |
| 2008/0039731 A1 | 2/2008 | McCombie et al. |
| 2008/0077026 A1 | 3/2008 | Banet et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | Leboeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0266326 A1* | 10/2008 | Porwal .................. G06F 1/1613 345/659 |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1* | 1/2009 | Ouchi et al. .................. 600/301 |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1* | 3/2009 | Yokoyama et al. .......... 600/509 |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198132 A1* | 8/2009 | Pelissier et al. .............. 600/443 |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0256113 A1 | 10/2009 | Liu et al. |
| 2009/0259113 A1 | 10/2009 | Liu et al. |
| 2009/0262074 A1* | 10/2009 | Nasiri et al. .................. 345/158 |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | McCombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |

(56) References Cited

U.S. PATENT DOCUMENTS

| | | | |
|---|---|---|---|
| 2011/0257555 A1 | 10/2011 | Banet et al. | |
| 2011/0275907 A1 | 11/2011 | Inciardi et al. | |
| 2012/0007891 A1* | 1/2012 | Chiang | G06F 1/1626 345/650 |
| 2012/0011469 A1* | 1/2012 | Chiang | G06F 1/1626 715/788 |
| 2012/0050161 A1* | 3/2012 | Andersson | G06F 1/1626 345/158 |
| 2012/0065525 A1 | 3/2012 | Douniama et al. | |
| 2012/0123232 A1 | 5/2012 | Najarian et al. | |
| 2013/0109928 A1* | 5/2013 | Menzel | 600/301 |
| 2014/0258870 A1* | 9/2014 | Gordon | G06F 1/1694 715/733 |

FOREIGN PATENT DOCUMENTS

| | | |
|---|---|---|
| WO | 1999032030 A1 | 7/1999 |
| WO | 2006005169 A1 | 1/2006 |
| WO | 2007024777 A2 | 3/2007 |
| WO | 2007143535 A2 | 12/2007 |
| WO | 2008110788 A1 | 9/2008 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

International Search Report and Written Opinion dated Jul. 22, 2011 in PCT/US2011/027843.
Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Cretikos et al., The Objective Medical Emergency Team Activation Criteria: a case-control study. Resuscitation Apr. 2007;73(1):62-72.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., An improved algorithm for respiration signal extraction from electrocardiogram measured by conductive textile electrodes using instantaneous frequency estimation. Med Bio Eng Comput 2008;46:147-158.
PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare . . . Jan. 30-Feb. 1, 2008: 169-172.
Wolf et al., Development of a Fall Detector and Classifier based on a Triaxial Accelerometer Demo Board. 2007:210-213.
Non-Final Office Action issued by the US Patent and Trademark Office dated Apr. 30, 2012 in U.S. Appl. No. 12/762,790.
Non-Final Office Action issued by the US Patent and Trademark Office dated Mar. 30, 2012 in U.S. Appl. No. 12/469,236.
Non-Final Office Action issued by the US Patent and Trademark Office dated Apr. 3, 2012 in U.S. Appl. No. 12/469,094.
Restriction Requirement issued by the US Patent and Trademark Office dated Feb. 2, 2012 in U.S. Appl. No. 12/469,222.
Non-Final Office Action issued by the US Patent and Trademark Office dated Mar. 27, 2012 in U.S. Appl. No. 12/559,426.
Non-Final Office Action issued by the US Patent and Trademark Office dated Apr. 3, 2012 in U.S. Appl. No. 12/559,039.
Non-Final Office Action issued by the US Patent and Trademark Office dated Dec. 29, 2011 in U.S. Appl. No. 12/559,080.
Response to Non-Final Office Action dated Mar. 19, 2012 in U.S. Appl. No. 12/559,080.
Notice of Allowance issued by the US Patent and Trademark Office dated Apr. 2, 2012 in U.S. Appl. No. 12/559,080.
Non-Final Office Action issued by the US Patent and Trademark Office dated Dec. 15, 2011 in U.S. Appl. No. 12/560,077.
Non-Final Office Action issued by the US Patent and Trademark Office dated Mar. 8, 2012 in U.S. Appl. No. 12/560,093.
Restriction Requirement issued by the US Patent and Trademark Office dated Dec. 14, 2012 in U.S. Appl. No. 12/560,093.
Response to Restriction Requirement submitted Feb. 15, 2012 in U.S. Appl. No. 12/560,093.
Non-Final Office Action issued by the US Patent and Trademark Office dated Mar. 1, 2012 in U.S. Appl. No. 12/560,104.
Restriction Requirement issued by the US Patent and Trademark Office dated Jan. 19, 2012 in U.S. Appl. No. 12/469,115.
Response to Restriction Requirement submitted Feb. 15, 2012 in U.S. Appl. No. 12/469,115.
Restriction Requirement issued by the US Patent and Trademark Office dated Nov. 14, 2011 in U.S. Appl. No. 12/469,127.

(56) References Cited

OTHER PUBLICATIONS

Response to Restriction Requirement submitted Feb. 15, 2012 in U.S. Appl. No. 12/469,127.
Non-Final Office Action issued by the US Patent and Trademark Office dated Mar. 9, 2012 in U.S. Appl. No. 12/469,127.
Non-Final Office Action issued by the US Patent and Trademark Office dated Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 5, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.
Non-Final Office Action issued by the US Patent and Trademark Office dated Jun. 11, 2012 in U.S. Appl. No. 12/469,222
Non-Final Office Action issued by the US Patent and Trademark Office dated Jun. 8, 2012 in U.S. Appl. No. 12/650,383.
Non-Final Office Action issued by the US Patent and Trademark Office dated Jun. 8, 2012 in U.S. Appl. No. 12/650,392.
Non-Final Office Action issued by the US Patent and Trademark Office dated Jun. 20, 2012 in U.S. Appl. No. 12/762,751.
International Search Report and Written Opinion dated Jun. 29, 2012 issued in PCT/US2012/025640.
Non-Final Office Action issued by the US Patent and Trademark Office dated Jul. 5, 2012 in U.S. Appl. No. 12/560,138.
Signal Strength. Oct. 6, 2008. http://web.archive.org/web/20081006200523/http://!en.wikipedia.org/wiki/Signal_strength.
Non-Final Office Action issued by the US Patent and Trademark Office dated May 24, 2012 in U.S. Appl. No. 12/560,111.
Restriction Requirement issued by the US Patent and Trademark Office dated Apr. 24, 2012 in U.S. Appl. No. 12/469,107.
Response to Restriction Requirement dated Jun. 14, 2012 in U.S. Appl. No. 12/469,107.
Non-Final Office Action issued by the US Patent and Trademark Office dated Jul. 18, 2012 in U.S. Appl. No. 12/650,389.
Chan et al., Noninvasive and Cuffless Measurements of Blood Pressure for Telemedicine. Proceedings of the 23rd Annual International Conference of the IEEE Engineering in Medicine and Biology Society 2001:3 pages.
Fung, Advisory System for Administration of Phenylephrine Following Spinal Anesthesia for Cesarean Section. Master's Thesis. University of British Columbia 2002: 119 pages.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Nitzan et al., Effects of External Pressure on Arteries Distal to the Cuff During Sphygmomanometry. IEEE Transactions on Biomedical Engineering, Jun. 2005;52(6):1120-1127.
USB 2.0 Specification Engineering Change Notice. Oct. 20, 2000.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College,Cambridge, UK, Aug. 19-22, 2007.
Zislin et al., Ways of Improving the Accuracy of Arterial Pressure Oscillometry. Biomedical Engineering 2005;39(4):174-178.
International Search Report and Written Opinion dated May 29, 2012 issued in PCT/US2012/025648.
Non-Final Office Action issued by the US Patent and Trademark Office dated Aug. 3, 2012 in U.S. Appl. No. 12/762,925.
Non-Final Office Action issued by the US Patent and Trademark Office dated Aug. 3, 2012 in U.S. Appl. No. 12/762,963.
Non-Final Office Action issued by the US Patent and Trademark Office dated Aug. 20, 2012 in U.S. Appl. No. 12/762,777.
Non-Final Office Action issued by the US Patent and Trademark Office dated Aug. 21, 2012 in U.S. Appl. No. 12/469,107.
Non-Final Office Action issued by the US Patent and Trademark Office dated Aug. 24, 2012 in U.S. Appl. No. 12/762,936.
International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office dated May 26, 2011 in U.S. Appl. No. 12/469,151
Response to Non-Final Office Action dated Nov. 25, 2011 in U.S. Appl. No. 12/469,151.
Notice of Allowance issued by the US Patent and Trademark Office dated Feb. 1, 2012 in U.S. Appl. No. 12/469,151.
Non-Final Office Action issued by the US Patent and Trademark Office dated Aug. 4, 2011 in U.S. Appl. No. 12/469,182.
Response to Non-Final Office Action dated Nov. 25, 2011 in U.S. Appl. No. 12/469,182.
Notice of Allowance issued by the US Patent and Trademark Office dated Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office dated Apr. 12, 2012 in U.S. Appl. No. 12/559,429.
Non-Final Office Action issued by the US Patent and Trademark Office dated Apr. 12, 2012 in U.S. Appl. No. 12/559,430.
Non-Final Office Action issued by the US Patent and Trademark Office dated Apr. 24, 2012 in U.S. Appl. No. 12/559,435.
Non-Final Office Action issued by the US Patent and Trademark Office dated Apr. 25, 2012 in U.S. Appl. No. 12/762,733.
Non-Final Office Action issued by the US Patent and Trademark Office dated Apr. 27, 2012 in U.S. Appl. No. 12/762,822.
Non-Final Office Action issued by the US Patent and Trademark Office dated Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
International Search Report and Written Opinion dated Apr. 27, 2012 as reported in PCT/US2011/067441.
Non-Final Office Action issued by the US Patent and Trademark Office dated May 7, 2012 in U.S. Appl. No. 12/469,115.
Non-Final Office Action issued by the US Patent and Trademark Office dated May 9, 2012 in U.S. Appl. No. 12/762,836.
Non-Final Office Action issued by the US Patent and Trademark Office dated May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6)JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.
Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office dated May 11, 2012 in U.S. Appl. No. 12/762,846.
Non-Final Office Action issued by the US Patent and Trademark Office dated May 11, 2012 in U.S. Appl. No. 12/762,874.
Non-Final Office Action issued by the US Patent and Trademark Office dated Aug. 30, 2012 in U.S. Appl. No. 12/469,202.

(56) References Cited

OTHER PUBLICATIONS

Non-Final Office Action issued by the US Patent and Trademark Office dated Aug. 31, 2012 in U.S. Appl. No. 12/469,213.
Non-Final Office Action issued by the US Patent and Trademark Office dated Sep. 14, 2012 in U.S. Appl. No. 12/650,374.
Drinnan et al., Relation between heart rate and pulse transit time during paced respiration. Physiol. Meas. Aug. 2001;22(3):425-432.
Flash et al., The Coordination of Arm Movements: An Experimentally Confirmed Mathematical Model. J Neurosci. Jul. 1985;5(7):1688-1703.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.
Non-Final Office Action issued by the US Patent and Trademark Office dated Sep. 17, 2012 in U.S. Appl. No. 12/469,192.
Gallagher, Comparison of Radial and Femoral Arterial Blood Pressure in Children after Cardiopulmonary Bypass. J Clin Monit. Jul. 1985;1(3):168-171.
Park et al., Direct Blood Pressure Measurements in Brachial and Femoral Arteries in Children. Circulation Feb. 1970;41(2)231-237.
Talkowski, Quantifying Physical Activity in Community Dwelling Older Adults Using Accelerometry. University of Pittsburgh (Dissertation) 2008:1-91.
Non-Final Office Action issued by the US Patent and Trademark Office dated Sep. 17, 2012 in U.S. Appl. No. 12/650,354.
Non-Final Office Action issued by the US Patent and Trademark Office dated Sep. 21, 2012 in U.S. Appl. No. 12/469,115.
Non-Final Office Action issued by the US Patent and Trademark Office dated Sep. 26, 2012 in U.S. Appl. No. 12/560,104.
Packet Definition. The Linux Information Project Jan. 8, 2006 http://www.linfo.org/packet.html.
RS-232. Wikipedia Dec. 5, 2008 http:l/web.archive.org/web/20081205160754/http:/len.wikipedia.org/wiki/RS-232.
Response to Non-Final Office Action issued in U.S. Appl. No. 12/469,236 dated Sep. 27, 2012.
Response to Non-Final Office Action issued in U.S. Appl. No. 12/487,283 dated Sep. 27, 2012.
Non-Final Office Action issued by the US Patent and Trademark Office dated Sep. 28, 2012 in U.S. Appl. No. 12/560,087.
Response to Non-Final Office Action issued in U.S. Appl. No. 12/762,836 dated Oct. 9, 2012.
Non-Final Office Action issued by the US Patent and Trademark Office dated Oct. 9, 2012 in U.S. Appl. No. 12/762,726.
Response to Non-Final Office Action issued in U.S. Appl. No. 12/559,429 dated Oct. 12, 2012.
Response to Non-Final Office Action issued in U.S. Appl. No. 12/559,430 dated Oct. 12, 2012.
Final Office Action issued by the US Patent and Trademark Office dated Oct. 22, 2012 in U.S. Appl. No. 12/762,822.
Response to Non-Final Office Action issued in U.S. Appl. No. 12/559,435 dated Oct. 23, 2012.
Final Office Action issued by the US Patent and Trademark Office dated Oct. 24, 2012 in U.S. Appl. No. 12/599,429.
Final Office Action issued by the US Patent and Trademark Office dated Oct. 24, 2012 in U.S. Appl. No. 12/599,430.
Non-Final Office Action issued by the US Patent and Trademark Office dated Oct. 23, 2012 in U.S. Appl. No. 12/762,944.
Response to Non-Final Office Action issued in U.S. Appl. No. 12/762,733 dated Oct. 25, 2012.
Final Office Action issued by the US Patent and Trademark Office dated Oct. 25, 2012 in U.S. Appl. No. 12/599,426.
Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.
Benefits of Digital Sensors. Gems Sensors. Feb. 14, 2008. http://web.archive.org/web/20080214122230/http://www.sensorland.com/HowPage054.html.
Final Office Action issued by the US Patent and Trademark Office dated Oct. 25, 2012 in U.S. Appl. No. 12/762,790.
Final Office Action issued by the US Patent and Trademark Office dated Oct. 26, 2012 in U.S. Appl. No. 12/762,836.
Non-Final Office Action issued by the US Patent and Trademark Office dated Oct. 30, 2012 in U.S. Appl. No. 12/559,386.
Non-Final Office Action issued by the US Patent and Trademark Office dated Nov. 6, 2012 in U.S. Appl. No. 12/559,379.
Non-Final Office Action issued by the US Patent and Trademark Office dated Nov. 6, 2012 in U.S. Appl. No. 12/650,370.
Poon and Zhang, Cuff-Less and Noninvasive Measurements of Arterial Blood Pressure by Pulse Transit Time. Conf Proc IEEE Eng Med Biol Soc. 2005;6:5877-5880.
Non-Final Office Action issued by the US Patent and Trademark Office dated Nov. 7, 2012 in U.S. Appl. No. 12/559,392.
Non-Final Office Action issued by the US Patent and Trademark Office dated Oct. 24, 2012 in U.S. Appl. No. 12/559,403.
Non Final Office Action issued by the United States Patent and Trademark Office in U.S. Appl. No. 12/559,413 dated Nov. 9, 2012.
Response to Office Action issued in U.S. Appl. No. 12/762,846 dated Nov. 13, 2012.
Response to Office Action issued in U.S. Appl. No. 12/762,874 dated Nov. 13, 2012.
Response to Office Action issued in U.S. Appl. No. 12/560,111 dated Nov. 26, 2012.
Response to Office Action issued in U.S. Appl. No. 11/930,881 dated Nov. 26, 2012.
Final Rejection issued by the United States Patent and Trademark Office in U.S. Appl. No. 12/559,419 dated Nov. 16, 2012.
Non Final Office Action issued by the United States Patent and Trademark Office in U.S. Appl. No. 12/559,408 dated Nov. 23, 2012.
Response to Office Action issued in U.S. Appl. No. 12/138,199 dated Nov. 29, 2012.
Response to Office Action issued in U.S. Appl. No. 12/650,383 dated Dec. 7, 2012.
Response to Office Action issued in U.S. Appl. No. 12/650,392 dated Dec. 7, 2012.
Final Rejection issued by the United States Patent and Trademark Office in U.S. Appl. No. 12/559,435 dated Dec. 12, 2012.
Final Rejection issued by the United States Patent and Trademark Office in U.S. Appl. No. 12/560,111 dated Dec. 12, 2012.
Clifford et al., Measuring Tilt with Low-g Accelerometers. Freescale Semiconductor, Inc., 2005:8 pages.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor for Extreme Environments. Conf Proc IEEE Eng Med Biol Soc. 2004;3:2192-2195.
Thongpithoonrat et al., Networking and Plug-and-Play of Bedside Medical Instruments. Conf Proc IEEE Eng Med Biol Soc. 2008;2008:1514-1517.
Yang et al., Research on Multi-Parameter Physiological Monitor Based on CAN Bus. IFMBE Proceed. 2008;19:417-419.
Zeltwanger, Controller Area Network and CANopen in Medical Equipment. Bus Briefing: Med Dev Manuf Technol. 2002:34-37.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Non Final Office Action issued by the United States Patent and Trademark Office in U.S. Appl. No. 13/432,976 dated Dec. 14, 2012.
Final Rejection issued by the United States Patent and Trademark Office in U.S. Appl. No. 12/762,733 dated Dec. 20, 2012.
Final Rejection issued by the United States Patent and Trademark Office in U.S. Appl. No. 12/762,846 dated Dec. 20, 2012.
Final Rejection issued by the United States Patent and Trademark Office in U.S. Appl. No. 12/650,392 dated Jan. 3, 2013.

(56) References Cited

OTHER PUBLICATIONS

Final Rejection issued by the United States Patent and Trademark Office in U.S. Appl. No. 12/487,283 dated Jan. 3, 2013.
Non Final Office Action issued by the United States Patent and Trademark Office in U.S. Appl. No. 13/292,923 dated Jan. 14, 2013.
Notice of Allowance issued by the United States Patent and Trademark Office in U.S. Appl. No. 11/470,708 dated Jan. 18, 2013.
International Search Report and Written Opinion issued in PCT/US2012/064302 dated Jan. 15, 2013.
Supplemental European Search Report issued in EP 10778376 dated Jan. 31, 2013.
Final Office Action issued by the United States Patent and Trademark Office in U.S. Appl. No. 12/559,039 dated Feb. 11, 2013
Reddan et al., Intradialytic Blood Volume Monitoring in Ambulatory Hemodialysis Patients: A Randomized Trial. J Am Soc Nephrol. Jul. 2005;16(7):2162-2169.
Final Office Action issued by the United States Patent and Trademark Office in U.S. Appl. No. 12/469,222 dated Feb. 13, 2013.
Non Final Office Action issued by the United States Patent and Trademark Office in U.S. Appl. No. 12/650,383 dated Feb. 15, 2013.
Non Final Office Action issued by the United States Patent and Trademark Office in U.S. Appl. No. 13/346,408 dated Feb. 25, 2013.
Final Office Action issued by the United States Patent and Trademark Office in U.S. Appl. No. 12/650,389 dated Mar. 14, 2013.
Klabunde, Mean Arterial Pressure. Cardiovascular Physiology Concepts. Mar. 8, 2007.http://web.archive.org/web/20070308182914/http://www.cvphysiology.com/Blood%20Pressure/BP006.htm.
Final Office Action issued by the United States Patent and Trademark Office in U.S. Appl. No. 12/762,874 dated Mar. 14, 2013.
Non Final Office Action issued by the United States Patent and Trademark Office in U.S. Appl. No. 13/196,326 dated Mar. 22, 2013.
De Scalzi et al., Relationship Between Systolic Time Intervals and Arterial Blood Pressure. Clin Cardiol. 1986;9:545-549.
Ahlstrom et al., Noninvasive investigation of blood pressure changes using the pulse wave transit time: a novel approach in the monitoring of hemodialysis patients. J Artif Organs. 2005;8(3):192-197.
Final Office Action issued by the United States Patent and Trademark Office in U.S. Appl. No. 12/762,751 dated Mar. 29, 2013.
Extended European Search Report and Written Opinion issued in EP 11754055 dated Jun. 17, 2015.

* cited by examiner

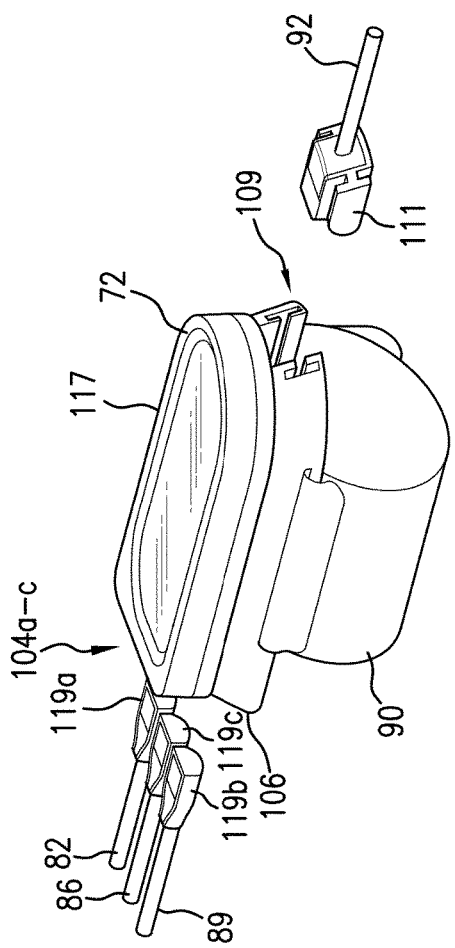
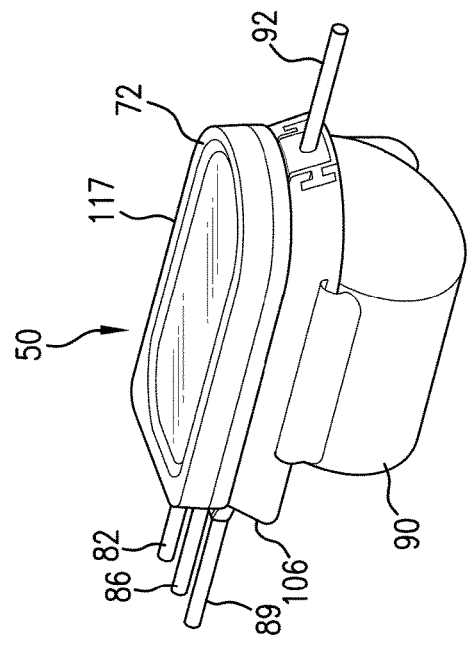
FIG.22A
FIG.22B

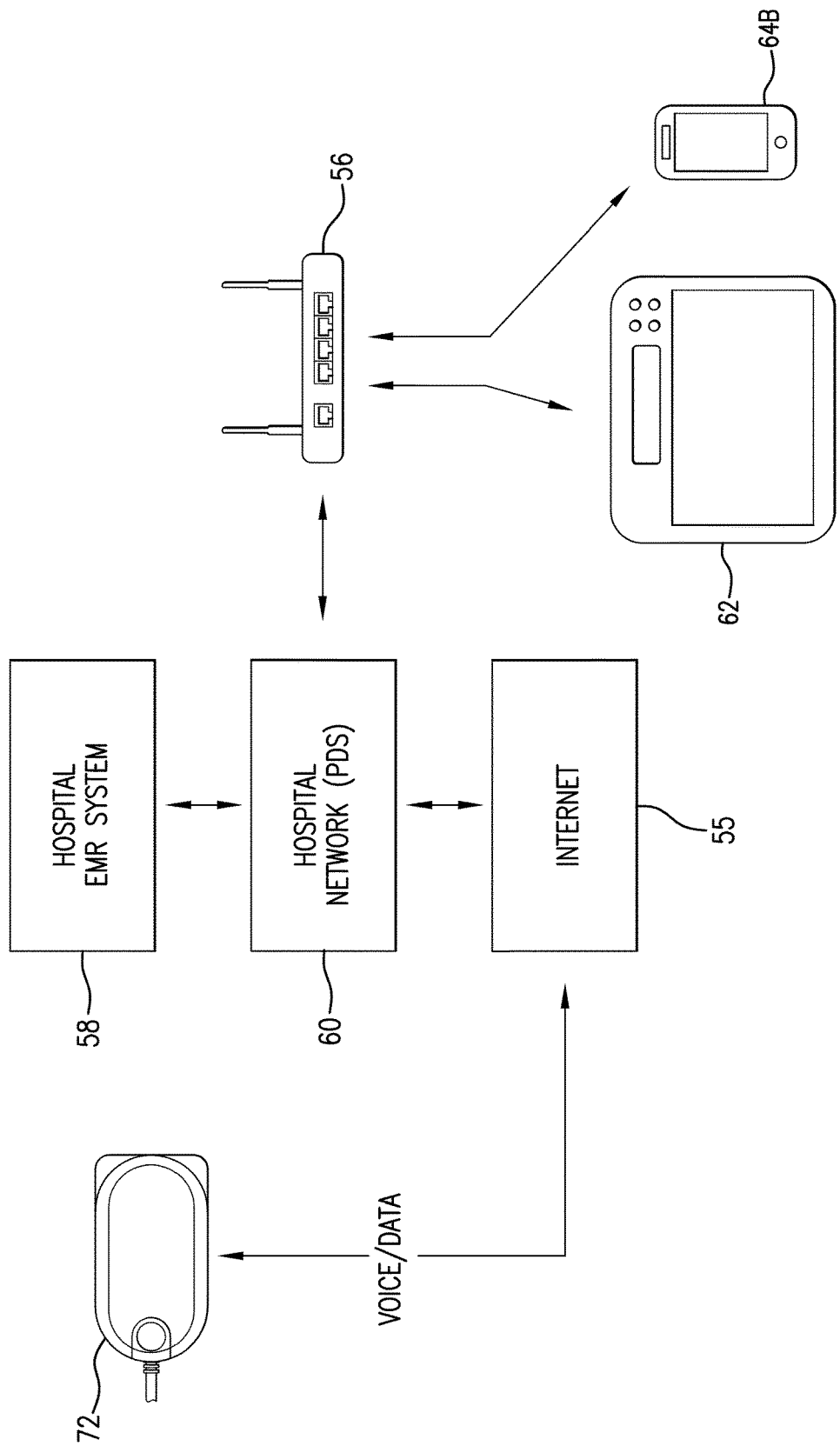

BODY-WORN VITAL SIGN MONITOR

CROSS REFERENCES TO RELATED APPLICATIONS

This application claims the benefit of U.S. Provisional Application No. 61/312,624, filed Mar. 10, 2010, entitled "BODY-WORN VITAL SIGN MONITOR", which is incorporated herein in its entirety.

STATEMENT REGARDING FEDERALLY SPONSORED RESEARCH OR DEVELOPMENT

Not Applicable

BACKGROUND OF THE INVENTION

Field of the Invention

The present invention relates to medical devices for monitoring vital signs, e.g., arterial blood pressure.

Description of the Related Art

Conventional vital sign monitors are used throughout the hospital, and are particularly commonplace in high-acuity areas such as the intensive care unit (ICU), emergency department (ED), or operating room (OR). Patients in these areas are generally sick and require a high degree of medical attention, typically provided by a relatively high ratio of clinicians compared to lower-acuity areas of the hospital. Outside the ICU and OR, clinicians typically measure vital signs such as systolic, diastolic, and mean arterial blood pressures (SYS, DIA, MAP), respiratory rate (RR), oxygen saturation (SpO2), heart rate (HR), and temperature (TEMP) with portable or wall-mounted vital sign monitors. It can be difficult to effectively monitor patients in this way, however, because measurements are typically made every few hours, and the patients are often ambulatory and not constrained to a single hospital room. This poses a problem for conventional vital sign monitors, which are typically heavy and unwieldy, as they are not intended for the ambulatory population. To make a measurement, a patient is typically tethered to the monitor with a series of tubes and wires. Some companies have developed ambulatory vital sign monitors with limited capabilities (e.g. cuff-based blood pressure using oscillometry and SpO2 monitoring), but typically these devices only make intermittent, rather than continuous, measurements. And even these measurements tend to work best on stationary patients, as they are easily corrupted by motion-related artifacts.

Most vital signs monitors feature a user interface that shows numerical values and waveforms associated with the vital signs, alarm parameters, and a 'service menu' that can be used to calibrate and maintain the monitor. Some monitors have internal wireless cards that communicate with a hospital network, typically using protocols such as 802.11b/g.

One of the most important parameters measured with vital signs monitors is blood pressure. In critical care environments like the ICU and OR, blood pressure can be continuously monitored with an arterial catheter inserted in the patient's radial or femoral artery. Alternatively, blood pressure can be measured intermittently with a cuff using oscillometry, or manually by a clinician using auscultation. Most vital sign monitors perform both catheter and cuff-based measurements of blood pressure. Blood pressure can also be monitored continuously with a technique called pulse transit time (PTT), defined as the transit time for a pressure pulse launched by a heartbeat in a patient's arterial system. PTT has been shown in a number of studies to correlate to SYS, DIA, and MAP. In these studies, PTT is typically measured with a conventional vital signs monitor that includes separate modules to determine both an electrocardiogram (ECG) and Spo2. During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows.

SpO2 is typically measured with a bandage or clothespin-shaped sensor that clips to a patient's finger and includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation detected by the photodetector to determine the patient's blood oxygen saturation level and a time-dependent waveform called a photoplethysmograph (PPG). Time-dependent features of the PPG indicate both pulse rate and a volumetric absorbance change in an underlying artery caused by the propagating pressure pulse.

Typical PTT measurements determine the time separating a maximum point on the QRS complex (indicating the peak of ventricular depolarization) and a foot of the PPG waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff and oscillometry. Typically during the calibration process the blood pressure cuff is applied to the patient, used to make one or more blood pressure measurements, and then left for future measurements. Going forward, the calibration measurements are used, along with a change in PTT, to measure the patient's continuous blood pressure (cNIBP). PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure both ECG and PPG waveforms which are then processed to determine PTT.

SUMMARY OF THE INVENTION

To improve the safety of hospitalized patients, particularly those in lower-acuity areas, it is desirable to have a body-worn monitor that continuously measures all vital signs from a patient, provides tools for effectively monitoring the patient, and wirelessly communicates with a hospital's information technology (IT) network. Preferably the monitor operates algorithms featuring: 1) a low percentage of false positive alarms/alerts; and 2) a high percentage of true positive alarms/alerts. The term 'alarm/alert', as used herein, refers to an audio and/or visual alarm generated directly by a monitor worn on the patient's body, or alternatively a remote monitor (e.g., a central nursing station). To accomplish this, the invention provides a body-worn monitor that measures a patient's vital signs (e.g. cNIBP, Spo2, HR, RR, and TEMP) while simultaneously characterizing their activity state (e.g. resting, walking, convulsing, falling) and posture (upright, supine). The body-worn monitor processes this information to minimize corruption of the vital signs and associated alarms/alerts by motion-related artifacts.

The body-worn monitor features a graphical user interface (GUI) rendered on a touchpanel display that facilitates a number of features to simplify and improve patient monitoring and safety in both the hospital and home. For example, the monitor features a battery-powered, wrist-worn transceiver that processes motion-related signals generated with an internal motion sensor (e.g. an accelerometer). When the transceiver's battery runs low, the entire unit can be swapped out by simply 'bumping' the original transceiver with a new one having a fully charged battery. Accelerometers within the transceivers detect the 'bump', digitize the corresponding signals, and wirelessly transmit them to a patient data server (PDS) within the hospital's network. There, the signals are analyzed and patient information (e.g. demographic and vital sign data) formerly associated with the original transceiver is re-associated with the new transceiver. A clinician can view the data using a computer functioning as a remote viewing device (RVD), such as a conventional computer on wheels (COW).

The body-worn monitor additionally includes a speaker, microphone, and software that collectively facilitate voice over IP (VOIP) communication. With these features, the wrist-worn transceiver can be used as a two-way communicator allowing, e.g., the patient to alert a clinician during a time of need. Additionally, during medical procedures or diagnoses, the clinician can enunciate annotations directly into the transceiver. These annotations along with vital sign information are wirelessly transmitted to the PDS and ultimately a hospital's electronic medical records (EMR) system, where they are stored and used for post-hoc analysis of the patient. In a related application, the transceiver includes a barcode scanner that, prior to administering medications, scans barcodes associated with the patient, clinician, and medications. The transceiver sends the decoded barcode information back to the PDS, where a software program analyzes it to determine that there are no errors in the medication or the rate at which it is delivered. A signal is then sent from the PDS to the GUI, clearing the clinician to administer the medications.

The body-worn monitor can determine a patient's location in addition to their vital signs and motion-related properties. Typically, the location-determining sensor and the wireless transceiver operate on a common wireless system, e.g. a wireless system based on 802.11a/b/g/n, 802.15.4, or cellular protocols. In this case a location is determined by processing the wireless signal with one or more algorithms known in the art. These include, for example, triangulating signals received from at least three different wireless base stations, or simply estimating a location based on signal strength and proximity to a particular base station. In still other embodiments the location sensor includes a conventional global positioning system (GPS).

VOIP-based communications typically take place between the body-worn monitor and a remote computer or telephone interfaced to the PDS. The location sensor, wireless transceiver, and first and second voice interfaces can all operate on a common wireless system, such as one of the above-described systems based on 802.11 or cellular protocols. In embodiments, the remote computer, for example, can be a monitor that is essentially identical to the transceiver worn by the patient, and can be carried or worn by a clinician. In this case the monitor associated with the clinician features a display wherein the user can select to display information (e.g. vital signs, location, and alarms) corresponding to a particular patient. This monitor can also include a voice interface so the clinician can communicate with the patient.

The wrist-worn transceiver's touchpanel display can render a variety of different GUIs that query the patient for their pain level, test their degree of 'mentation', i.e. mental activity, and perform other functions to assist and improve diagnosis. Additionally, the transceiver supports other GUIs that allow the patient to order food within the hospital, change the channel on their television, select entertainment content, play games, etc. To help promote safety in the hospital, the GUI can also render a photograph or video of the patient or, in the case of neo-natal patients, their family members.

The body-worn monitor can include a software framework that generates alarms/alerts based on threshold values that are either preset or determined in real time. The framework additionally includes a series of 'heuristic' rules that take the patient's activity state and motion into account, and process the vital signs accordingly. These rules, for example, indicate that a walking patient is likely breathing and has a regular heart rate, even if their motion-corrupted vital signs suggest otherwise.

The body-worn monitor features a series of sensors that attach to the patient to measure time-dependent PPG, ECG, ACC, oscillometric (OSC), and impedance pneumography (IP) waveforms. A microprocessor (CPU) within the monitor continuously processes these waveforms to determine the patient's vital signs, degree of motion, posture and activity level. Sensors that measure these signals typically send digitized information to the wrist-worn transceiver through a serial interface, or bus, operating on a controlled area network (CAN) protocol. The CAN bus is typically used in the automotive industry, and allows different electronic systems to effectively and robustly communicate with each other with a small number of dropped packets, even in the presence of electrically noisy environments. This is particularly advantageous for ambulatory patients that may generate signals with large amounts of motion-induced noise.

Blood pressure is determined continuously and non-invasively using a technique, based on PTT, which does not require any source for external calibration. This technique, referred to herein as the 'Composite Technique', determines blood pressure using PPG, ECG, and OSC waveforms. The Composite Technique is described in detail in the co-pending patent application, the contents of which are fully incorporated herein by reference: BODY-WORN SYSTEM FOR MEASURING CONTINUOUS NON-INVASIVE BLOOD PRESSURE (CNIBP) (U.S. Ser. No. 12/650,354; filed Nov. 15, 2009). In other embodiments, PTT can be calculated from time-dependent waveforms other than the ECG and PPG, and then processed to determine blood pressure. In general, PTT can be calculated by measuring a temporal separation between features in two or more time-dependent waveforms measured from the human body. For example, PTT can be calculated from two separate PPGs measured by different optical sensors disposed on the patient's fingers, wrist, arm, chest, ear, or virtually any other location where an optical signal can be measured using a transmission or reflection-mode optical configuration. In other embodiments, PTT can be calculated using at least one time-dependent waveform measured with an acoustic sensor, typically disposed on the patient's chest. Or it can be calculated using at least one time-dependent waveform measured using a pressure sensor, typically disposed on the patient's bicep, wrist, or finger. The pressure sensor can include, for example, a pressure transducer, piezoelectric sensor, actuator, polymer material, or inflatable cuff.

Specifically, in one aspect, the invention provides a method for monitoring a patient featuring the following steps: (a) associating a first set of vital sign information measured from the patient with a first transceiver that includes a first motion sensor; (b) storing the first set of vital sign information in a computer memory; (c) contacting the first transceiver with a second transceiver that includes a second motion sensor, the contacting causing the first motion sensor to generate a first motion signal and the second motion sensor to generate a second motion signal; (d) processing the first and second motion signals to determine that the first transceiver is to be replaced by the second transceiver; and (e) associating a second set of vital sign information with the patient, the second set of vital sign information measured with the second transceiver.

In embodiments, both the first and second motion sensors are accelerometers that generate time-dependent waveforms (e.g. ACC waveforms). Contacting the two transceivers typically generates waveforms that include individual 'pulses' (e.g. a sharp spike) caused by rapid acceleration and deceleration detected by the respective accelerometers. Typically the pulses are within waveforms generated along the same axes in both transceivers. The pulses can be collectively processed (using, e.g., an autocorrelation algorithm) to determine that they are generated during a common period of time. In embodiments, amplitudes of the first and second pulses are required to exceed a pre-determined threshold value in order for the second transceiver to replace the first transceiver. Pulses that meet this criterion are wirelessly transmitted to a remote server, where they are processed as described above. If the server determines that the second transceiver is ready to replace the first transceiver, it transmits instruction information to the transceivers to guide the replacement process. This instruction information, for example, is displayed by the GUIs of both transceivers. Once the replacement process is complete, vital sign information measured by the second transceiver is stored along with that measured by the first transceiver in a computer memory (e.g. a database) on the remote computer. The vital sign information can include conventional vital signs (e.g. HR, SYS, DIA, RR, and TEMP), along with the time-dependent waveforms used to calculate the vital signs (e.g. PPG, ECG, OSC, IP) and motion-related properties (ACC). Patient demographic information (e.g. name, gender, weight, height, date of birth) can also be associated with both the first and second sets of vital sign information.

In another aspect, the invention provides a method for pairing a patient monitor with a remote display device (e.g. an RVD) using a methodology similar to that described above. The display device is typically a portable display device (e.g. a personal digital assistant, or PDA), or a remote computer, such as a COW or central nursing station. The method includes the following steps: (a) contacting either a display device or an area proximal to the display device with the transceiver to generate a motion signal with its internal accelerometer; (b) transmitting the motion signal to a computer; (c) processing the motion signal with the computer to associate the transceiver with the display device; (d) measuring a set of vital sign information from the patient with the transceiver; and (e) displaying the set of vital sign information on the display device. Here, the act of contacting the display device with the transceiver generates a pulse in the ACC waveform, as described above. Processing done by the computer analyzes both the pulse and a location of the display device to associate it with the transceiver.

Several methods can be used to determine the location of the display device. For example, the wireless transmitter within the transceiver is configured to operate on a wireless network, and algorithms operating on the remote computer and can analyze signals between the transceiver and wireless access points within the network (e.g. RSSI signals indicating signal strength) to determine an approximate location of the transceiver and thus the display device which it contacts. In embodiments the algorithms can involve, e.g., triangulating at least three RSSI values, or simply estimating location by determining the nearest access point from a single RSSI value. Triangulation typically involves using a map grid that includes known locations of multiple wireless access points and display devices within a region of the hospital; the map grid is determined beforehand and typically stored, e.g., in a database. For example, the approximate location of the transceiver can be determined using triangulation. Then the nearest display device, lying with a known location within a pre-determined radius, is paired with the transceiver. Typically the pre-determined radius is between 1-5 m.

In another aspect, the invention provides a body-worn monitor including first and second sensors attached to the patient, and a processing component that interfaces to both sensors and processes signals from them to calculate at least one vital sign value. A wireless transmitter receives the vital sign value and transmits it over a wireless interface, and additionally provides a two-way communications system configured to transmit and receive audio signals over the same wireless interface. In embodiments, the two-way communications system includes a speaker and a microphone, both of which are integrated into the transceiver. Typically the wireless interface is a hospital-based wireless network using an 802.11 protocol (e.g. 802.11a/b/g/n). A VOIP system typically runs on the wireless network to supply two-way voice communications. Alternatively the wireless network is based on a cellular protocol, such as a GSM or CDMA protocol.

Typically the body-worn monitor features a wrist-worn transceiver that functions as a processing component, and includes a touchpanel display configured to render both patient and clinician interfaces. The touchpanel display is typically a liquid crystal display (LCD) or organic light-emitting diode display (OLED) display with a clear touchpanel utilizing established resistive or capacitive technologies adhered to its front surface. The patient interface is typically rendered by default, and includes a graphical icon that, when initiated, activates the two-way communications system. The clinician interface typically requires a security code (entered using either a 'soft' numerical keypad or through a barcode scanner) to be activated. The transceiver typically includes a strap configured to wrap around the patient's arm, and most typically the wrist; this allows it to be worn like a conventional wristwatch, which is ideal for two-way communications between the patient and a clinician.

In a related aspect, the invention provides a wrist-worn transceiver wherein the two-way communications system described above, or a version thereof, is used as a voice annotation system. Such a system receives audio signals (typically from a clinician), digitizes them, and transmits the resulting digital audio signals, or a set of parameters determined from these signals, over the wireless interface to a computer memory. The audio signals are typically used to annotate vital sign information. They can be used, for example, to indicate when a pharmaceutical compound is administered to the patient, or when the patient undergoes a specific therapy. Typically the voice annotation uses the same speaker used for the two-way communication system. It also may include a speech-to-text converter that converts audio annotations from the clinician into text fields that can be easily stored alongside the vital sign information. In embodiments, both a text field and the original audio annotation are stored in a computer memory (e.g. database), and can be edited once stored. In other embodiments, a pre-determined text field (indicating, e.g., that a specific medication is delivered at a time/date automatically determined by the transceiver) is used to annotate the vital sign information. In still other embodiments, a set of parameters determined from the digital audio signals can include an icon or a numerical value. Annotations in the database can be viewed afterwards using a GUI that renders both the vital sign information (shown, e.g., in a graphical form) and one or more of the annotations (e.g. icon, text field, numerical value, or voice annotation).

In another aspect, the invention provides a wrist-worn transceiver featuring a GUI that the patient can use to indicate their level of pain. Here, the GUI typically includes a touchpanel display configured to render a set of input fields, with each input field in the set indicating a different level of pain. Once contacted, the input fields generate a signal that is processed to determine the patient's level of pain. This signal can be further processed and then wirelessly transmitted to a remote computer for follow-on analysis.

In embodiments, the touchpanel display features a touch-sensitive area associated with each input field that generates a digital signal (e.g. a number) after being contacted. Each input field is typically a unique graphical icon such as a cartoon or numerical value indicating an escalating level of pain. The transceiver can also include a voice annotation system similar to that described above so the patient can specifically describe their pain (e.g. its location) using their own voice. This information can be wirelessly transmitted to a remote computer (e.g. a PDS) featuring a display device (e.g. an RVD). This system can render both vital sign information and a parameter determined from the pain signal, and can additionally include an alarming system that activates an alarm if the pain signal or a parameter calculated therefrom exceeds a pre-determined threshold.

In a related aspect, the invention provides a wrist-worn transceiver that includes a mentation sensor configured to collect data input characterizing the patient's level of mentation (e.g. mental acuity). This information, along with traditional vital signs and the waveforms they are calculated from, is wirelessly transmitted to a remote computer for analysis. In embodiments, the mentation sensor is a touchpanel display that renders a GUI to collect information characterizing the patient's level of mentation. For example, the GUI can render a series of icons, a game, test, or any other graphical or numerical construct that can be used to evaluate mentation. In a specific embodiment, for example, the GUI includes a set of input fields associated with a numerical value. Here, the mentation 'test' features an algorithm to determine if the input fields are contacted by the patient in a pre-determined numerical order. Upon completion, the test results can be evaluated to generate a mentation 'score'. In this aspect, the wrist-worn transceiver also includes a two-way communication system that receives audio information from the patient. This audio information can be used for conventional communication purposes, and can additionally be analyzed to further gauge mentation. As in previous embodiments, the mentation score can be sent with vital sign information to a PDS/RVD for follow-on analysis. These systems may include an alarming system that generates an alarm if the mentation parameter or a parameter calculated therefrom exceeds a pre-determined threshold.

In another aspect, the invention provides a wrist-worn transceiver featuring a motion sensor (e.g. an accelerometer, mercury switch, or tilt switch) that generates a motion signal indicating the transceiver's orientation. The processing component within the transceiver processes the motion signal and, in response, orients the GUI so that it can be easily viewed in 'rightside up' configuration, i.e. with text rendered in a conventional manner from left to right. If the transceiver is moved (e.g., so that it is viewed by a clinician instead of a patient), the accelerometers generate new motion signals, and the GUI is 'flipped' accordingly. Typically, for example, the GUI is rendered in either a first orientation or a second orientation, with the two orientations separated by 180 degs., and in some cases by 90 degs. In embodiments, the first orientation corresponds to a 'patient GUI', and the second orientation corresponds to a 'clinician GUI'. This allows, for example, the appropriate GUI to be automatically rendered depending on the transceiver's orientation. The clinician GUI typically includes medical parameters, such as vital signs and waveforms, whereas the patient GUI typically includes non-medical features, such as a 'nurse call button', time/date, and other components described in more detail below.

In preferred embodiments, the motion sensor is a 3-axis accelerometer configured to generate a time-domain ACC waveform. During a measurement, the processing component additionally analyzes the waveform to determine parameters such as the patient's motion, posture, arm height, and degree of motion.

In another aspect of the invention, the wrist-worn transceiver features a display device configured to render at least two GUIs, with the first GUI featuring medical content, and the second GUI featuring non-medical content relating to entertainment, food service, games, and photographs. The photograph, for example, can include an image of the patient or a relative of the patient; this latter case may be particularly useful in neo-natal hospital wards. To capture the photograph, the body-worn monitor may include a digital camera, or a wireless interface to a remote digital camera, such as that included in a portable computer or cellular telephone.

In other embodiments, the second GUI is configured to render menus describing entertainment content, such as television (e.g. different channels or pre-recorded content), movies, music, books, and video games. In this case, the touchpanel display can be used to select the content or, in embodiments, play a specific game. The wireless transmitter within the transceiver is further configured to transmit and receive information from a remote server configured to store digital representations of these media sources. In still other embodiments, the second GUI is configured to display content relating to a food-service menu. Here, the wireless transmitter is further configured to transmit and receive information from a remote server configured to interface with a food-service system.

In another aspect, the invention provides a system for monitoring a patient that includes a vital sign monitor configured to be worn on the patient's body, and a remote computer. The vital sign monitor features connection means (e.g. a flexible strap or belt) configured to attach a transceiver to the patient's body, and sensor with a sensing portion (e.g. electrodes and an optical sensor) that attaches to the patient to measure vital sign information. A mechanical housing included in the transceiver covers a wireless decoder, processing component, and wireless transmitter, and supports a display component. The wireless decoder (e.g. a barcode scanner or radio frequency identification (RFID) sensor) is configured to detect information describing a medication, a medication-delivery rate, a clinician, and the patient. For example, this information may be encoded in a barcode or RFID tag located on the patient, clinician, medication, or associated with an infusion pump. The processing component is configured to process: 1) the vital sign information to generate a vital sign and a time-dependent waveform; and 2) information received by the wireless decoder to generate decoded information. The wireless transmitter within the mechanical housing receives information from the processing component, and transmits it to a remote computer. In response the remote computer processes the information and transmits an information-containing packet back to the vital sign monitor.

In embodiments, the remote computer performs an analyzing step that compares information describing both the medication and the patient to database information within a database. The database may include, for example, a list of acceptable medications and acceptable medication-delivery rates corresponding to the patient. In some cases both the vital sign information and the decoded information are collectively analyzed and compared to values in the database to affect treatment of the patient. For example, this analysis may determine that a patient with a low blood pressure should not receive medications that further lower their blood pressure. Or it may suggest changing a dosage level of the medication in order to compensate for a high heart rate value. In general, the remote computer can analyze one or more vital sign values corresponding to a patient, along with the patient's demographic information, medical history, and medications, and determine acceptable medications and medication-delivery rates based on this analysis. In response, the computer can transmit a packet back to the vital sign monitor, which renders its contents on the display. The packet can include a message confirming that a particular medication and medication-delivery rate are acceptable for the patient, and may also include a set of instructions for delivering the medication and performing other therapies.

Still other embodiments are found in the following detailed description of the invention, and in the claims.

BRIEF DESCRIPTION OF THE DRAWINGS

FIGS. 22A and 22B show, respectively, three-dimensional images of the wrist-worn transceiver before and after receiving cables from other sensors within the body-worn monitor;

FIG. 28 shows an alternate IT configuration of the invention where the wrist-worn transceiver of FIG. 1 communicates with the PDS through an internal cellular modem connected to the Internet.

DETAILED DESCRIPTION OF THE INVENTION

System Overview

Figure 1:
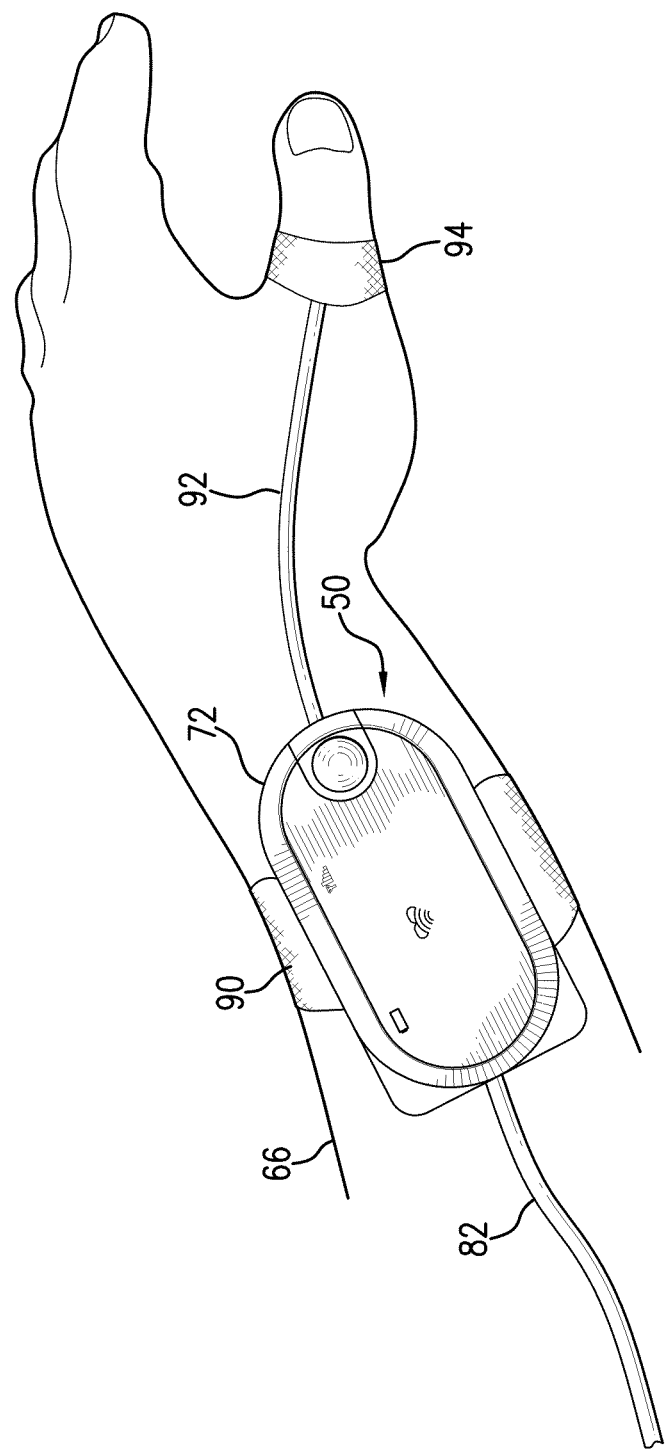
FIG. 1 is a schematic drawing showing the wrist-worn transceiver of the invention attached to a patient's wrist.

FIG. 1 shows a transceiver 72 according to the invention that attaches to a patient's wrist 66 using a flexible strap 90. The transceiver 72 connects through a first flexible cable 92 to a thumb-worn optical sensor 94, and through a second flexible cable 82 to an ECG circuit and a series of chest-worn electrodes (not shown in the figure). During a measurement, the optical sensor 94 and chest-worn electrodes measure, respectively, time-dependent optical waveforms (e.g. PPG) and electrical waveforms (e.g. ECG and IP), which are processed as described below to determine vital signs and other physiological parameters such as cNIBP, SpO2, HR, RR, TEMP, pulse rate (PR), and cardiac output (CO). Once measured, the transceiver 72 wirelessly transmits these and other information to a remote PDS and RVD. The transceiver 72 includes a touchpanel display that renders a GUI 50 which, in turn, displays the vital signs, physiological parameters, and a variety of other features described in detail below. Collectively, the transceiver 72 and GUI 50 incorporate many features that are normally reserved for non-medical applications into a body-worn vital sign monitor that continuously monitors ambulatory patients as they move throughout the hospital.

Figure 2:
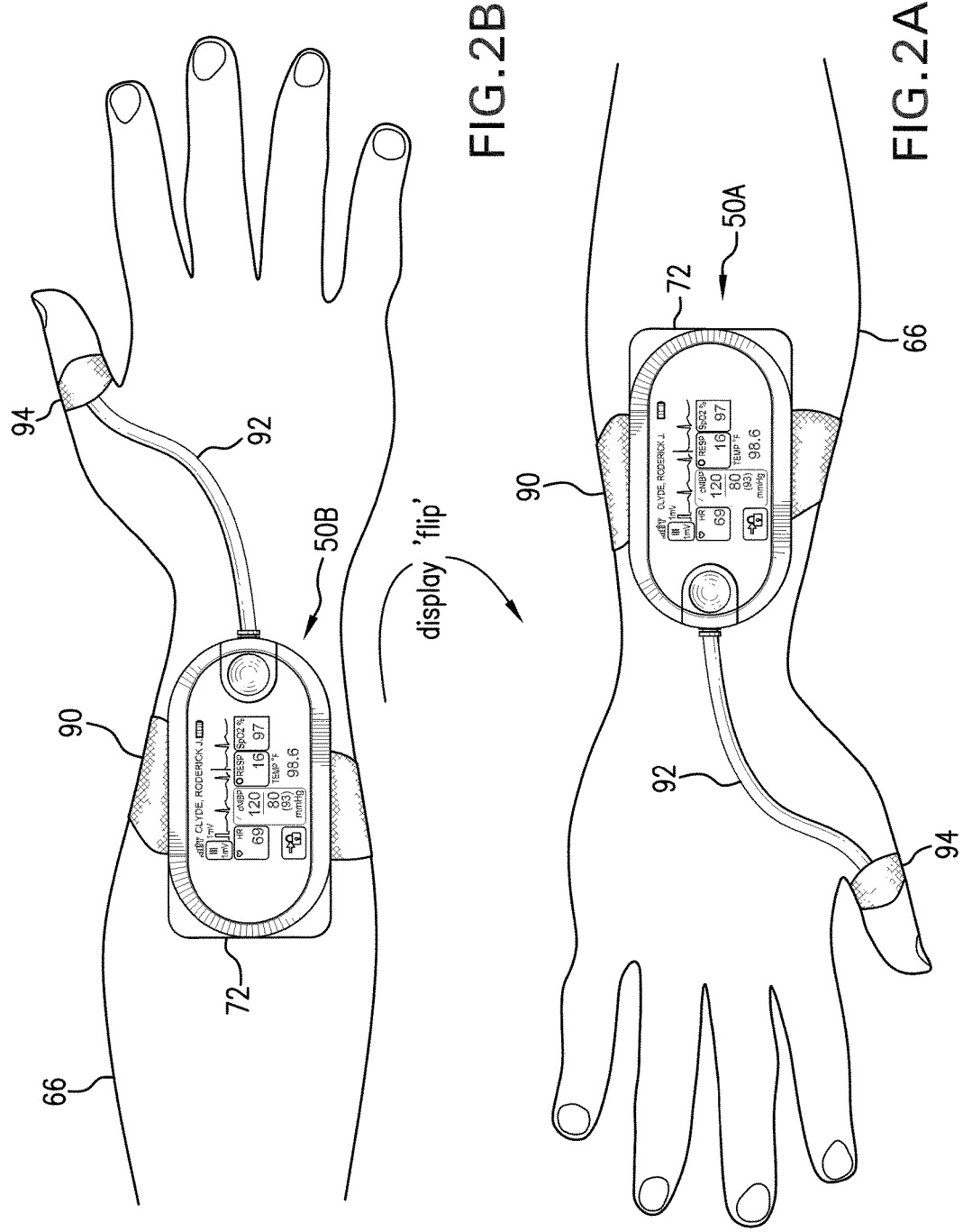
FIGS. 2A and 2B show, respectively, schematic drawings of the wrist-worn transceiver of FIG. 1 oriented 'rightside up' so that a patient can view the GUI, and 'upside down' so that a clinician can view the GUI.

The transceiver 72 includes an embedded accelerometer that senses its motion and position, and in response can affect properties of the GUI. Referring to FIGS. 2A and 2B, for example, time-resolved ACC waveforms from the accelerometer can be processed with a microprocessor within the transceiver to detect orientation of the touchpanel display. This information can then be analyzed to determine if it is the clinician or patient who is viewing the display. In response, the GUI can 'flip' so that it is properly oriented (i.e. 'rightside up', as opposed to being upside down) for the viewer. For example, as shown in FIG. 2A, when the transceiver 72 is worn on the patient's right wrist 66 the internal accelerometer generates ACC waveforms that are processed by the microprocessor to determine this orientation. The GUI 50A is adjusted according so that it is always oriented with numbers and text arranged rightside up and read from left to right. When the patient's arm is rotated, as shown in FIG. 2B, the ACC waveforms change accordingly because the accelerometer's axes are swapped with respect to gravity. Such a situation would occur, for example, if a clinician were to orient the patient's arm in order read the transceiver's display. In this case, the ACC waveforms are processed to determine the new orientation, and the GUI 50B is flipped so it is again rightside up, and can be easily read by the clinician.

The internal accelerometer can also detect if the transceiver is 'bumped' by an external object. In this case, the ACC waveform will feature a sharp 'spike' generated by rapid acceleration and deceleration caused by the bumping process. As described in detail below, such a bumping process can serve as a fiducial marker that initiates a specific event related to the transceiver, such as a battery swap or process that involves pairing the transceiver to an external wireless system or display.

The accelerometer within the transceiver, when combined with other accelerometers within the body-worn monitor, can also be used to determine the patient's posture, activity level, arm height and degree of motion, as described in detail below. Use of one or more accelerometers to detect such motion-related activities is described, for example, in the following patent applications, the contents of which are incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009).

Figure 3:
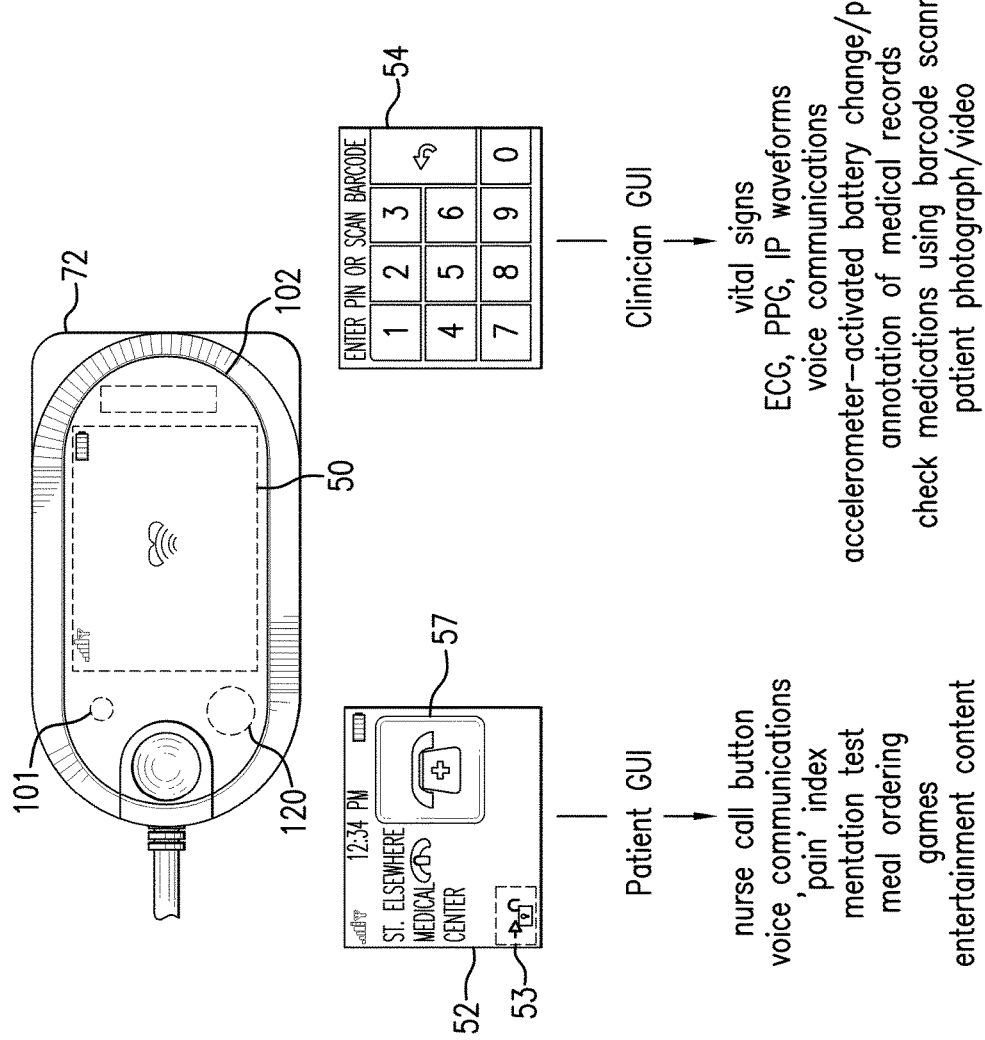
FIG. 3 shows a schematic drawing of the wrist-worn transceiver of FIG. 1 and a list of features available in both a patient GUI and a clinician GUI.

Referring to FIG. 3, in addition to the GUI 50, the transceiver 72 includes a high-fidelity speaker 120, a microphone 101, and a barcode scanner 102 which, respectively, enunciates audible information, measures voice signals from both the patient and a clinician, and scans graphical barcodes to decode numerical information describing the patient and their medication. Signals from these and other components are processed to supply information to either a 'patient GUI' 52 or a 'clinician GUI' 54. The patient GUI 52, for example, typically includes features that are decoupled from a standard clinical diagnosis; these include a nurse call button, voice communications, a 'pain' index, a mentation test to estimate the patient's cognitive abilities, meal ordering within the hospital, games, and a controller for entertainment content, e.g. to adjust parameters (e.g. channels, volume) for a standard television set. The clinical GUI 54, in comparison, includes features that are used for clinical diagnoses and for operating the transceiver in a hospital environment. The primary features of this GUI 54 include displaying vital signs (e.g. cNIBP, SpO2, HR, RR, TEMP), other medical parameters (e.g. PR, CO), and waveforms (PPG, ECG, IP). Secondary features of the clinical GUI include voice communications, battery-change and pairing operations using the above-described 'bump' methodology, voice annotation of medical records and diagnoses, a method for checking medications using the barcode scanner 102, and display of a photograph or video describing the patient.

During normal operation, the GUI renders 50 simple icons indicating that the transceiver is powered on and operational (e.g., a 'beating heart'), the strength of the wireless signal (e.g. a series of bars with escalating height), and the battery level (e.g. a cartoon of a battery with a charge-dependent gauge). The transceiver 72 displays these icons until the touchpanel display is contacted by either the patient or a clinician. This process yields the patient GUI 52, which features a large icon 57 showing a telephone (which is used for nurse call applications, as described below), and a smaller icon 53 showing a lock which, when tapped, enables the clinician to 'unlock' the transceiver and utilize the clinician interface 54. The transceiver 72 immediately renders a GUI that shows vital signs and waveform information if the patient's physiological condition requires immediate medical attention, e.g. in the case of cardiac arrest.

Figure 6:
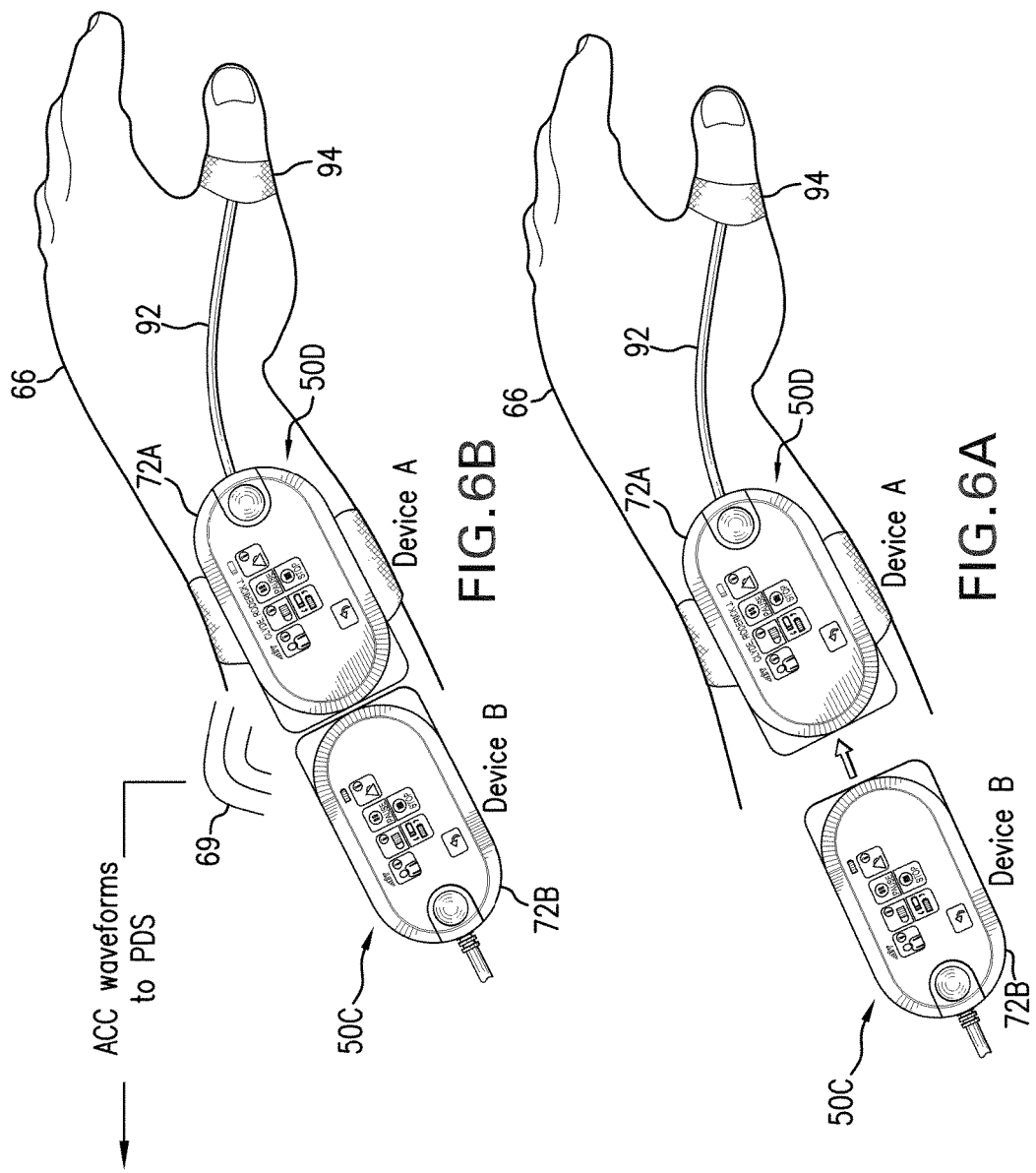
FIGS. 6A and 6B show, respectively, schematic drawings of a new transceiver having a fully charged battery being swapped with an original transceiver having a depleted battery before and after deploying the 'bump' methodology.
Figure 20:
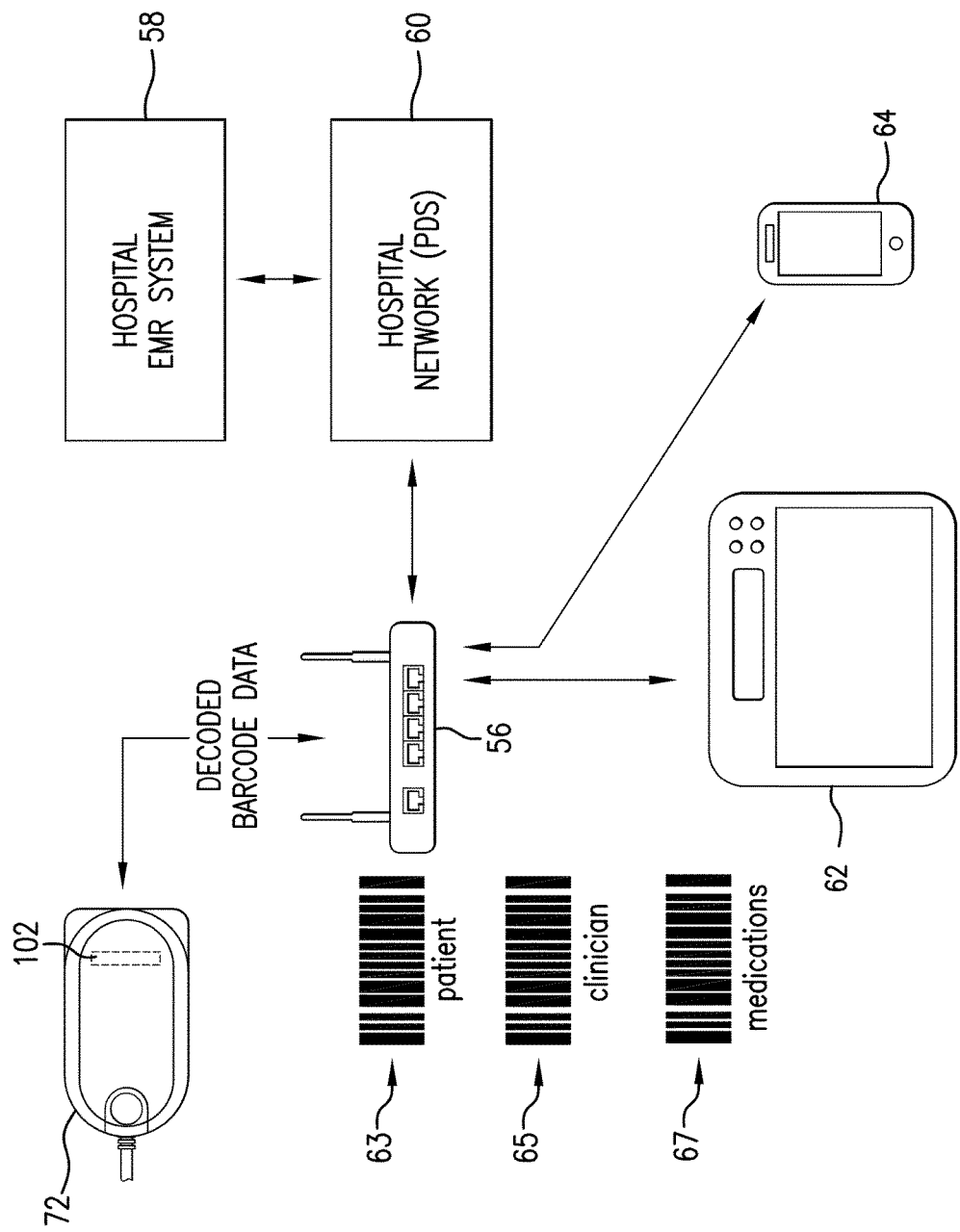
FIG. 20 shows a schematic drawing of the barcode scanner in the wrist-worn transceiver scanning barcodes associated with a patient, clinician, and medication, and sending the decoded barcode information to the PDS.

The clinician interface 54 is password-protected to prevent the patient or any other non-clinician from viewing important and potentially confusing medical information. A password can either be entered as a standard personal identification number (PIN) by tapping keys on a numerical keypad (as shown in FIG. 3), or by simply swiping a barcode printed on the clinician's hospital badge across the barcode scanner 102. The microprocessor within the transceiver unlocks the clinician interface following either of these events, and enables all the features associated with the interface, which are described in detail below. For example, with this interface the clinician can view vital signs and waveforms to make a medical diagnosis, as described with reference to FIG. 24. If the transceiver's battery charge is running low, the clinician can swap in a new transceiver and transfer data from the original transceiver simply by 'bumping' the two transceivers together, as described with reference to FIGS. 6-8. Medical records can be voice-annotated and stored on the PDS or a hospital's EMR using the process shown in FIGS. 11-13. The patient's medication can be checked by scanning and processing information encoded in barcodes associated with the patient, clinician, and medication, as shown in FIG. 20. All of this functionality is programmed within the transceiver and the body-worn monitor, and can be accomplished without tethering the patient to a conventional vital sign monitor typically mounted on a wall in the hospital or a rolling stand. Ultimately this allows the patient to wear a single body-worn monitor as they transition throughout the various facilities within the hospital, e.g. the ED, ICU, x-ray facility, and operating room.

Hardware in Body-Worn Monitor

Figure 4:
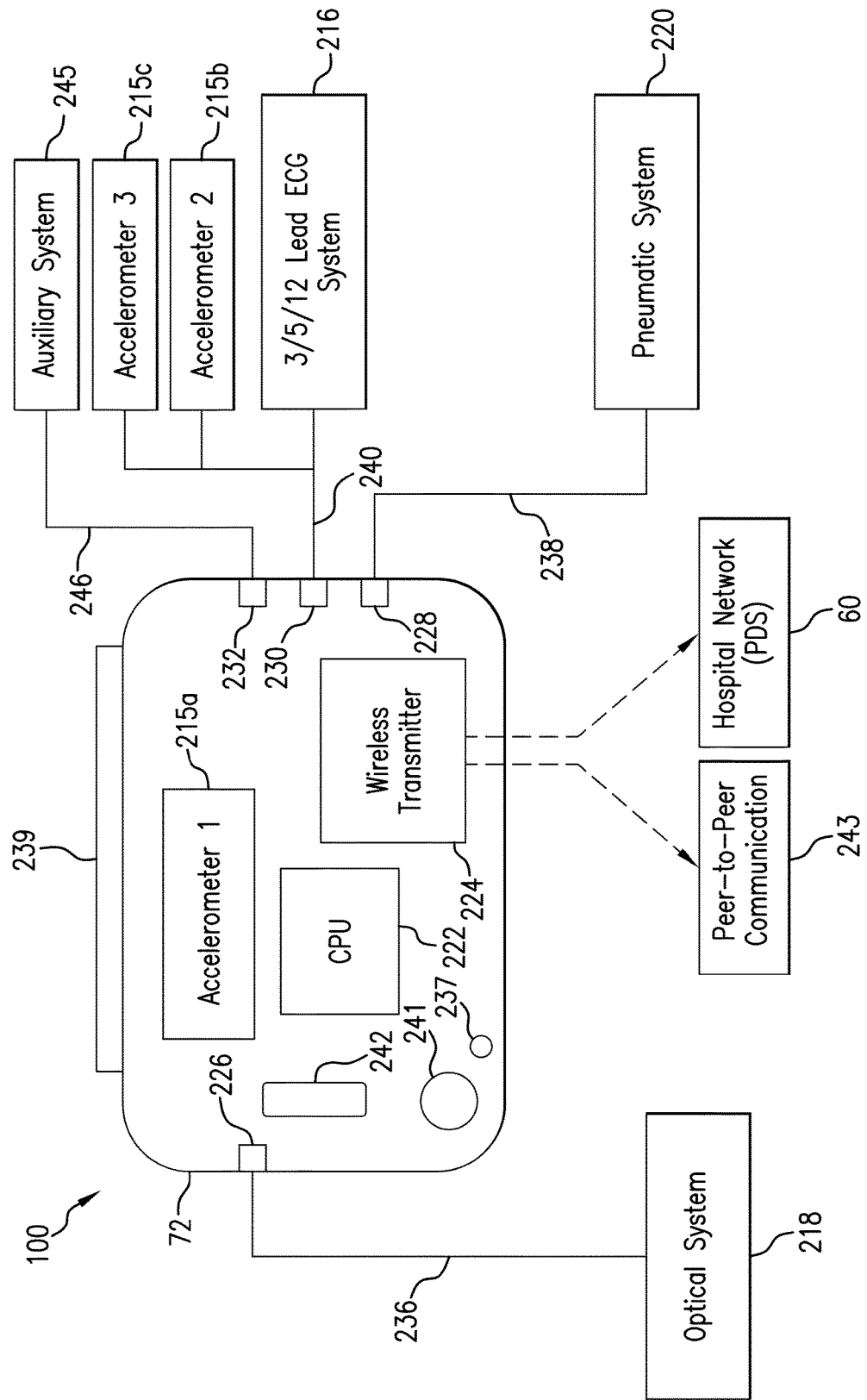
FIG. 4 shows a schematic drawing of the body-worn monitor featuring sensors for measuring ECG, PPG, ACC, OSC, and IP waveforms, and systems for processing these to determine a patient's vital signs.
Figure 5:
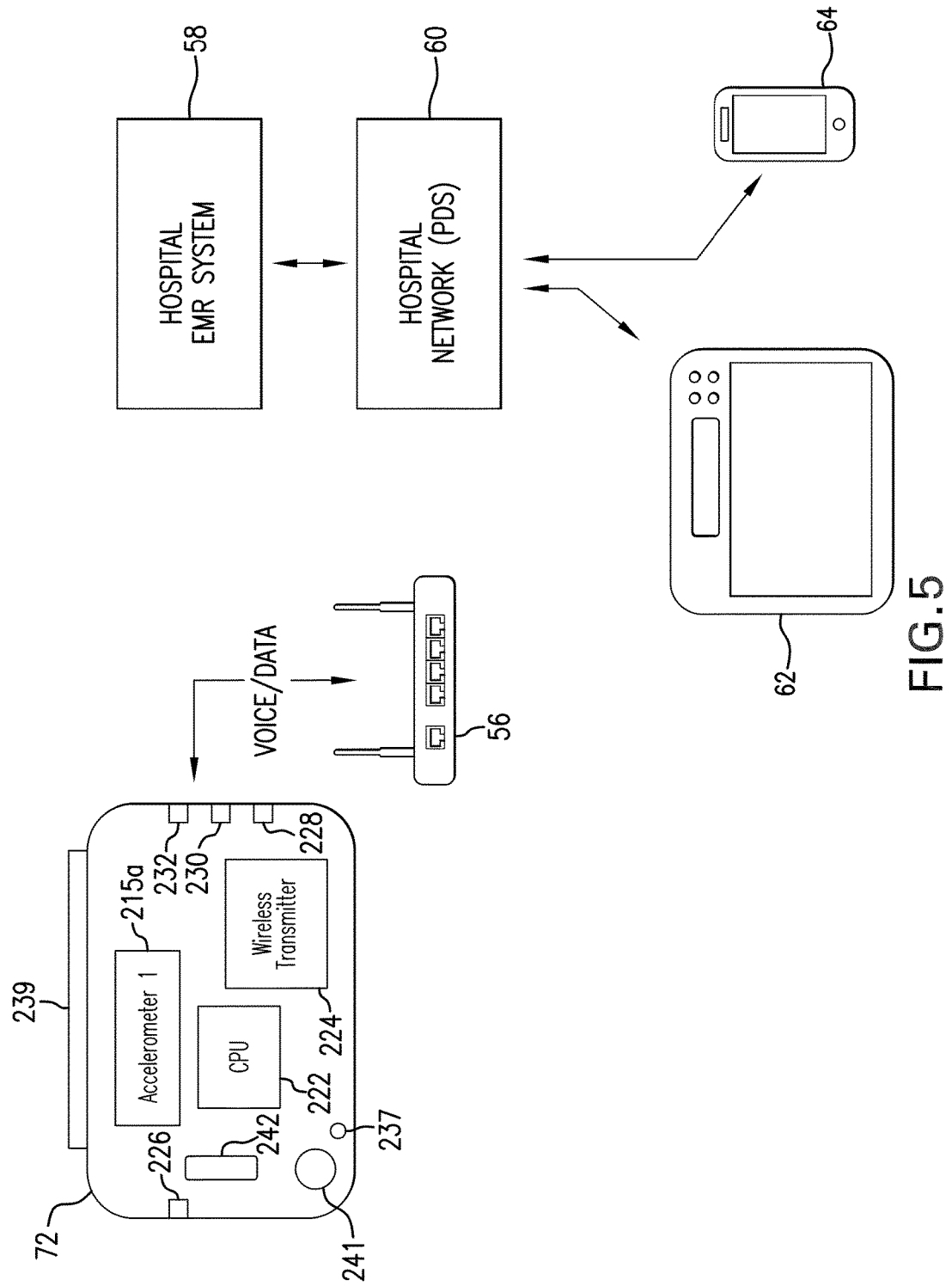
FIG. 5 shows a schematic drawing of an IT configuration of the invention where the body-worn monitor of FIG. 4 is connected through a wireless network to a PDS and hospital EMR.

FIGS. 4 and 5 show schematic drawings of a body-worn monitor 100 used to measure vital signs from a patient and render the different GUIs described above (FIG. 4), along with a wireless system over which the transceiver 72 sends information through a hospital network 60 to either a remote RVD, e.g. a computer 62 or hand-held device 64 (FIG. 5). Referring to FIG. 4, the body-worn monitor 100 features a wrist-worn transceiver 72 that continuously determines vital signs and motion-related properties from an ambulatory patient in a hospital. The monitor 100 is small, lightweight, and comfortably worn on the patient's body during their stay in the hospital; its specific form factor is described in detail below with reference to FIGS. 21 and 22. It provides continuous monitoring, and features a software framework that determines alarms/alerts if the patient begins to decompensate. Such systems are described in the following co-pending patent applications, the contents of which have been previously incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). The framework processes both the patient's motion and their vital sign information with algorithms that reduce the occurrence of false alarms.

A combination of features makes the body-worn monitor 100 ideal for ambulatory patients within the hospital. For example, as shown in FIG. 5, the transceiver 72 features a wireless transmitter 224 that communicates through a collection of wireless access points 56 (e.g. routers based on 802.11 protocols) within a hospital network 60, which includes a PDS. From the PDS 60 data are sent to an RVD (e.g. a portable tablet computer 62) located at a central nursing station, or to a local computer (e.g. a hand-held PDA 64) carried by the clinician. In embodiments, data can be sent to the PDA 64 through a peer-to-peer wireless connection. The specific mode of communication can be determined automatically (using, e.g., a signal strength associated with the wireless connection), or manually through an icon on the GUI.

The transceiver 72 features a CPU 222 that communicates through a digital CAN interface, or bus, to external systems featuring ECG 216, external accelerometers 215b-c, pneumatic 220, and auxiliary 245 sensors. Each sensor 215b-c, 216, 220, 245 is 'distributed' on the patient to minimize the bulk and weight normally associated with conventional vital sign monitors, which typically incorporate all electronics associated with measuring vital signs in a single plastic box. Moreover, each of these sensors 215b-c, 216,220, 245 generate digital signals close to where they actually attach to the patient, as opposed to generating an analog signal and sending it through a relatively long cable to a central unit for processing. This can reduce noise due to cable motion which is often mapped onto analog signals. Cables 240, 238, 246 used in the body-worn monitor 210 to transmit packets over the CAN bus typically include five separate wires bundled together with a single protective cladding: the wires supply power and ground to the remote ECG system 216, accelerometers 215b-c, pneumatic 220, and auxiliary systems 245; provide high/low signal transmission lines for data transmitted over the CAN protocol; and provide a grounded electrical shield for each of these four wires. There are several advantages to this approach. First, a single pair of transmission lines in the cable (i.e. the high/low signal transmission lines) can transmit multiple digital waveforms generated by completely different sensors. This includes multiple ECG waveforms (corresponding, e.g., to vectors associated with three, five, and twelve-lead ECG systems) from the ECG circuit, along with ACC waveforms associated with the x, y, and z axes of accelerometers within the body-worn monitor 100. The same two wires, for example, can transmit up to twelve ECG waveforms (measured by a twelve-lead ECG system), and six ACC waveforms (measured by the accelerometers 215b-c). Limiting the transmission line to a pair of conductors reduces the number of wires attached to the patient, thereby decreasing the weight and any cable-related clutter. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts.

The ECG 216, pneumatic 220, and auxiliary 245 systems are stand-alone systems that each includes a separate CPU, analog-to-digital converter, and CAN transceiver. During a measurement, they connect to the transceiver 72 through cables 240, 238, 246 and connectors 230, 228, 232 to supply digital inputs over the CAN bus. The ECG system 216, for example, is completely embedded in a terminal portion of its associated cable. Systems for three, five, and twelve-lead ECG monitoring can be swapped in an out simply by plugging the appropriate cable (which includes the ECG system 216) into a CAN connector 230 on the wrist-worn transceiver 72, and the attaching associated electrodes to the patient's body.

As described above, the transceiver 72 renders separate GUIs that can be selected for either the patient or a clinician. To do this, it includes a barcode scanner 242 that can scan a barcode printed, e.g., on the clinician's badge. In response it renders a GUI featuring information (e.g. vital signs, waveforms) tailored for a clinician that may not be suitable to the patient. So that the patient can communicate with the clinician, the transceiver 72 includes a speaker 241 and microphone 237 interfaced to the CPU 222 and wireless system 224. These components allow the patient to communicate with a remote clinician using a standard VOIP protocol. A rechargeable Li:ion battery 239 powers the transceiver 72 for about four days on a single charge. When the battery charge runs low, the entire transceiver 72 is replaced using the 'bump' technique described in detail below.

Three separate digital accelerometers 215a-c are non-obtrusively integrated into the monitor's form factor; two of them 215b-c are located on the patient's body, separate from the wrist-worn transceiver 72, and send digitized, motion-related information through the CAN bus to the CPU 222. The first accelerometer 215a is mounted on a circuit board within the transceiver 72, and monitors motion of the patient's wrist. The second accelerometer 215b is incorporated directly into the cable 240 connecting the ECG system 216 to the transceiver 72 so that it can easily attach to the patient's bicep and measure motion and position of the patient's upper arm. As described below, this can be used to orient the screen for viewing by either the patient or clinician. Additionally, signals from the accelerometers can be processed to compensate for hydrostatic forces associated with changes in the patient's arm height that affect the monitor's cNIBP measurement, and can be additionally used to calibrate the monitor's blood pressure measurement through the patient's 'natural' motion. The third accelerometer 215c is typically mounted to a circuit board that supports the ECG system 216 on the terminal end of the cable, and typically attaches to the patient's chest. Motion and position of the patient's chest can be used to determine their posture and activity states, which as described below can be used with vital signs for generating alarm/alerts. Each accelerometer 215a-c measures three unique ACC waveforms, each corresponding to a separate axis (x, y, or z) representing a different component of the patient's motion. To determine posture, arm height, activity level, and degree of motion, the transceiver's CPU 222 processes signals from each accelerometer 215a-c with a series of algorithms, described in the following pending patent applications, the contents of which have been previously incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). In total, the CPU 222 can process nine unique, time-dependent signals corresponding to the three axes measured by the three separate accelerometers. Algorithms determine parameters such as the patient's posture (e.g., sitting, standing, walking, resting, convulsing, falling), the degree of motion, the specific orientation of the patient's arm and how this affects vital signs (particularly cNIBP), and whether or not time-dependent signals measured by the ECG 216, optical 218, or pneumatic 220 systems are corrupted by motion.

To determine blood pressure, the transceiver 72 processes ECG and PPG waveforms using a measurement called with Composite Technique, which is described in the following patent application, the contents of which have been previously incorporated herein by reference: BODY-WORN SYSTEM FOR MEASURING CONTINUOUS NON-INVASIVE BLOOD PRESSURE (cNIBP) (U.S. Ser. No. 12/650,354; filed Nov. 15, 2009). The Composite Technique measures ECG and PPG waveforms with, respectively, the ECG 216 and optical 218 systems. The optical system 218 features a thumb-worn sensor that includes LEDs operating in the red ($\lambda$~660 nm) and infrared ($\lambda$~900 nm) spectral regions, and a photodetector that detects their radiation after it passes through arteries within the patient's thumb. The ECG waveform, as described above, is digitized and sent over the CAN interface to the wrist-worn transceiver 72, while the PPG waveform is transmitted in an analog form and digitized by an analog-to-digital converter within the transceiver's circuit board. The pneumatic system 220 provides a digitized pressure waveform and oscillometric blood pressure measurements through the CAN interface; these are processed by the CPU 222 to make cuff-based 'indexing' blood pressure measurements according to the Composite Technique. The indexing measurement typically only takes about 40-60 seconds, after which the pneumatic system 220 is unplugged from its connector 228 so that the patient can move within the hospital without wearing an uncomfortable cuff-based system. The optical waveforms measured with the red and infrared wavelengths can additionally be processed to determine SpO2 values, as described in detail in the following patent application, the contents of which is incorporated herein by reference: BODY-WORN PULSE OXIMETER (U.S. Ser. No. 12/559,379; filed Sep. 14, 2009).

Collectively, these systems 215a-c, 216, 218, and 220 continuously measure the patient's vital signs and motion, and supply information to the software framework that calculates alarms/alerts. A third connector 232 also supports the CAN bus and is used for auxiliary medical devices 245 (e.g. a glucometer, infusion pump, system for measuring end-tidal CO2) that is either worn by the patient or present in their hospital room.

Once a measurement is complete, the transceiver 72 uses the internal wireless transmitter 224 to send information in a series of packets to a PDS 60 within the hospital. The wireless transmitter 224 typically operates on a protocol based on 802.11, and can communicate with the PDS 60 through an existing network within the hospital as described above with reference to FIG. 5. Information transmitted by the transceiver alerts the clinician if the patient begins to decompensate. The PDS 60 typically generates this alarm/alert once it receives the patient's vital signs, motion parameters, ECG, PPG, and ACC waveforms, and information describing their posture, and compares these parameters to preprogrammed threshold values. As described in detail below, this information, particularly vital signs and motion parameters, is closely coupled together. Alarm conditions corresponding to mobile and stationary patients are typically different, as motion can corrupt the accuracy of vital signs (e.g., by adding noise), and induce artificial changes in them (e.g., through acceleration of the patient's heart and respiratory rates) that may not be representative of the patient's actual physiology.

Swapping and Pairing Transceivers Using 'Bump' Methodology

FIGS. 6A, 6B, 7, and 8 show how a wrist-worn transceiver 72A with a depleted battery can be swapped with a similar transceiver 72B having a fully charged battery using the 'bump' methodology described above. Prior to the swap, as shown in FIG. 6A, both transceivers are readied by activating the appropriate GUI 50C, 50D following the screens shown in FIG. 8. This process activates firmware on each transceiver 72A, 72B indicating that the swap is about to occur. In response, each transceiver sends a packet through the wireless access point 56 and to the hospital network and PDS 60. The packet describes a transceiver-specific address, e.g. a MAC address associated with its wireless transmitter. Once this is done, the GUIs 50C, 50D on both transceivers 72A, 72B indicate to a clinician that they can be 'bumped' together, and that the swap can proceed.

At this point, as shown in FIG. 6A, the new transceiver 72B (with the fully charged battery) is then bumped against the old transceiver 72A (with the depleted battery). Internal accelerometers within both transceivers 72A, B detect the bumping process and, in response, independently generate ACC waveforms 130, 132, both featuring a sharp spike indicating the rapid acceleration and deceleration due to the bumping process. Typically the ACC waveforms 130, 132 correspond to the same axes in both transceivers. The ACC waveforms are digitized within each transceiver and then transmitted through the wireless access point 56 to the PDS 60, where they are stored in a computer memory and analyzed with a software program that is activated when both devices are 'readied', as described above. The software program compares formatted versions of the ACC waveforms 130', 132' to detect the rapid spikes, as shown by the graph 140 in FIG. 7. The rapid spikes in the waveforms 130', 132' should occur within a few microseconds of each other, as indicated by the shaded window 142 in the graph 140. Other transceivers operating on the network may generate similar motion-related spikes due to movements of the patient wearing them, but the probability that such spikes occur at the exact same time as the transceivers being swapped is extremely low. The software program interprets the concurrence of the spikes as indicating that data stored on the old transceiver 72A is to be transferred to the new transceiver 72B. The data, for example, includes demographic information describing the patient (e.g. their name, age, height, weight, photograph), the medications they are taking, and all the vital sign and waveform information stored in memory in the old transceiver 72A. Following the bump, this information is associated with the address corresponding to the new transceiver 72B. At this time information may also be sent from the PDS so it can be stored locally on the new transceiver. When all the relevant information is transferred over, the GUIs 50C, 50D on both transceivers 72A, 72B indicate that they can be swapped. At this point, cables connected to the optical sensor and ECG electrodes are unplugged from the old transceiver 72A, and plugged into the new transceiver 72B. The clinician then attaches the new transceiver to the patient's wrist, and commences measuring vital signs from the patient as described above.

In other embodiments, a time period corresponding to a portion (e.g. a peak value) of the motion-generated spike is determined on each of the wrist-worn transceivers that are bumped together. Each transceiver then sends its time period to the PDS, where they are collectively analyzed to determine if they are sufficiently close in value (e.g. within a few hundred milliseconds). If this criterion is met, software on the PDS assumes that the transceivers are ready to be swapped, and performs the above-described steps to complete this process.

Figure 8:
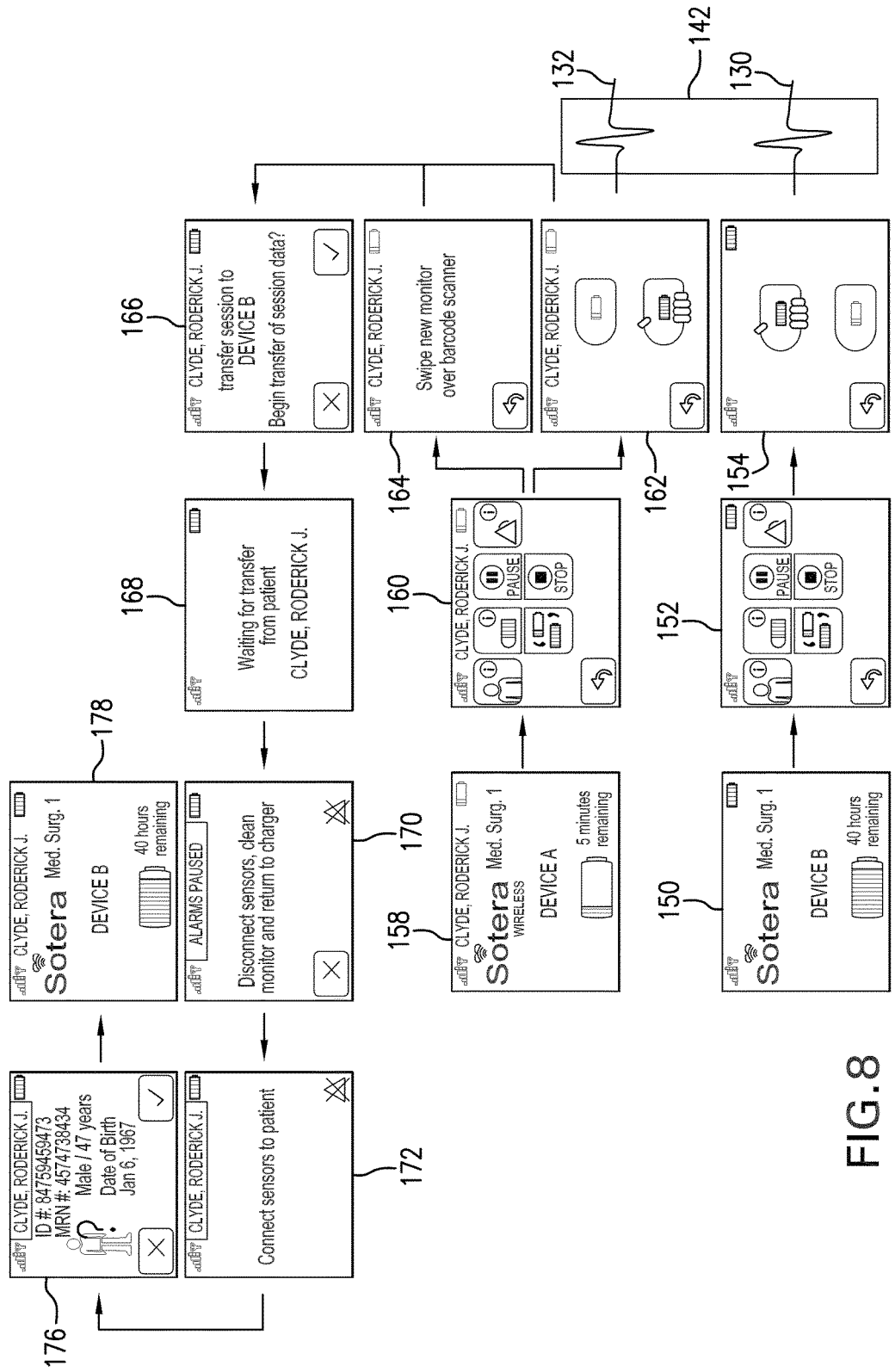
FIG. 8 shows screen captures from a GUI used to guide a clinician through the 'bump' methodology of FIGS. 6A, 6B, and 7.

FIG. 8 shows a sequence of screens within the GUI that describe the process for swapping transceivers to the clinician. The process begins when a screen 158 rendered by Device A indicates that its battery is running low of charge. This is indicated by a standard 'low battery' icon located in the upper right-hand corner of the screen 158, as well as a larger icon located near the bottom of the screen. A time describing the remaining life of the battery appears near this icon when this time is 5 minutes or less. Each transceiver includes a sealed internal Li:ion battery that cannot be easily replaced in the hospital. Instead, the transceiver is inserted in a battery charger that typically includes eight or sixteen ports, each of which charges a separate transceiver. To swap Device A with Device B, the clinician taps the screen 158 to yield a new screen 160 which includes a series of six icons, each related to a unique feature. The icon in the lower left-hand corner shows two interchanging batteries. When tapped, this icon yields a new screen 160 indicating that Device A is ready to be swapped. Device B is then removed from a port in the battery charger, and a sequence of screens 150, 152, 154 are initiated as described with reference to Device A.

When Devices A and B both show, respectively, screens 162, 154, they are ready to be swapped using the 'bumping' process. At this point, as described above, a clinician 'bumps' Device B into Device A, which in turn generates two ACC waveforms 130, 132 featuring sharp, time-dependent spikes indicating the bump. The waveforms 130, 132 include spikes, as shown by the shaded box 142, which are concurrent in time, and are wirelessly transmitted in a packet that indicates their origin through the pathway shown in FIG. 7 to the PDS. There, they are analyzed by the software program described above to determine that data associated with Device A (e.g. patient information, vital signs) is now associated with Device B. When this association is complete, the PDS transmits a packet back through the pathway shown in FIG. 7 to both Device A and B, indicating that the PDS is ready to transfer the data. Device B then renders a screen 166 asking the clinician to confirm the process. Data is transferred if the clinician taps the 'check' box in the lower right-hand corner of the screen; during this process Device B renders a screen 168 that shows the patient's name to further confirm with the clinician that the transfer process is valid. When it is complete, Device A is no longer active, meaning it cannot collect data or generate alarms. Device B renders a screen 170 that instructs the clinician to disconnect the optical and electrical sensors from Device A, and to clean this device and insert it into the battery charger. During this process all alarms are paused for Device B. A screen 172 on Device B then instructs the clinician to connect the sensors and attach Device B to the patient's wrist. When this is complete, Device B renders a final confirmatory screen 176, which when checked finalizes the swapping process. At this point Device B is officially associated with the patient, renders a standard screen 178, and commences measuring vital signs from the patient. These vital signs, along with those collected from Device A, are included in a contiguous data file characterizing the patient.

Figure 7:
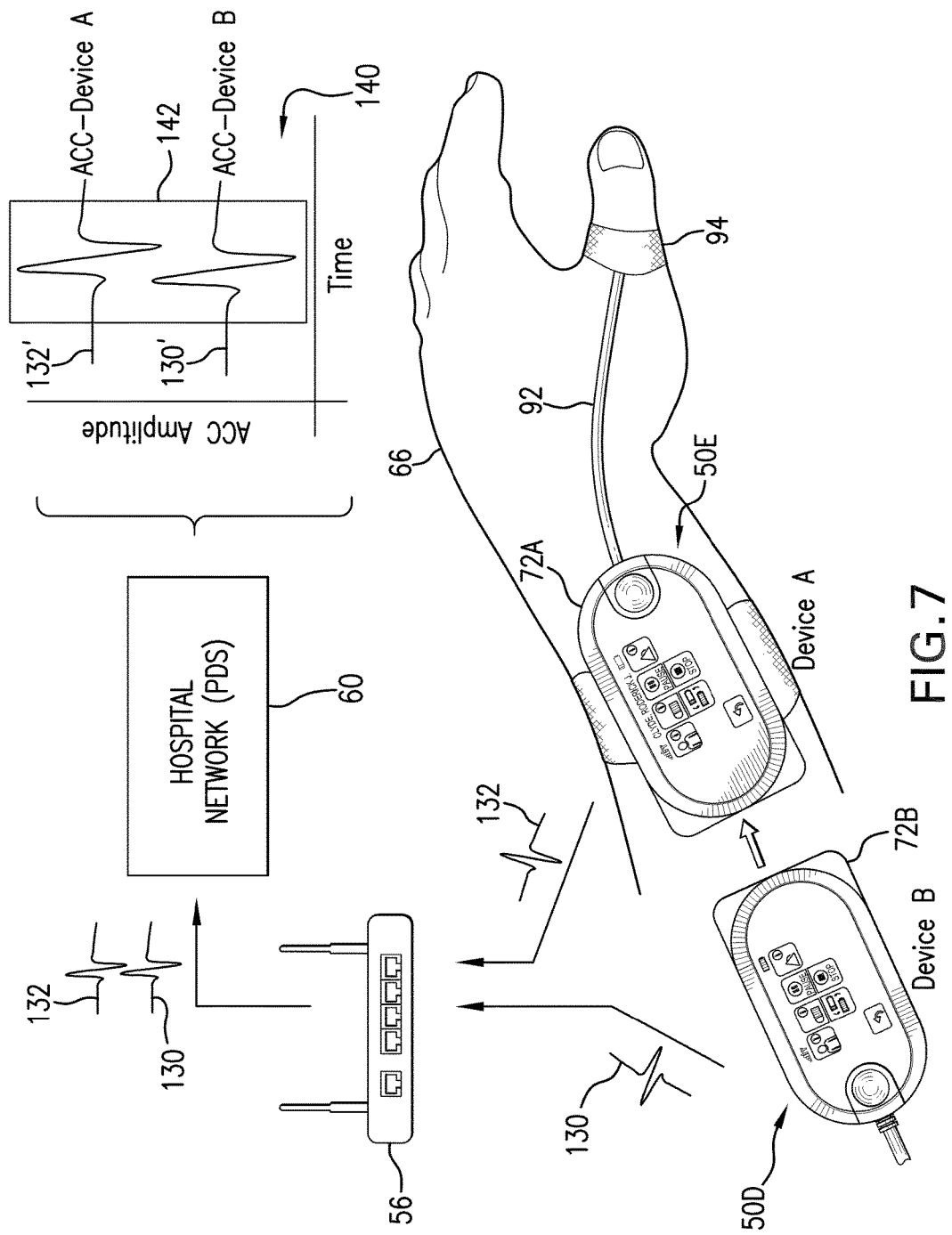
FIG. 7 shows a schematic drawing of transceivers undergoing the 'bump' methodology of FIGS. 6A and 6B and wirelessly transmitting their ACC waveforms to the PDS for analysis.

As an alternative to the 'bumping' process, Device B's barcode can be read and processed to facilitate swapping the transceivers. In this case, an icon on Device A, when tapped, renders a screen 164 indicating that Device A is ready to read the barcode printed on Device B. At this point, Device B's barcode is swiped across Device A's barcode reader, decoded, and wirelessly transmitted to the PDS as indicated in FIG. 7. The PDS uses this information to associate Device B with the patient as described above. Once this is complete, Device B uses the same screens used for the 'bumping' transfer process (screens 166, 168, 170, 172, 176, 178) to associate Device B with the patient. The 'bumping' process shown in FIG. 6 takes place along the long axes of Device A and Device B. Alternatively, it can take place along the short axes of these devices. Or the short axis of one device can be bumped against the long axis of the other device to initiate the process.

Figure 9:
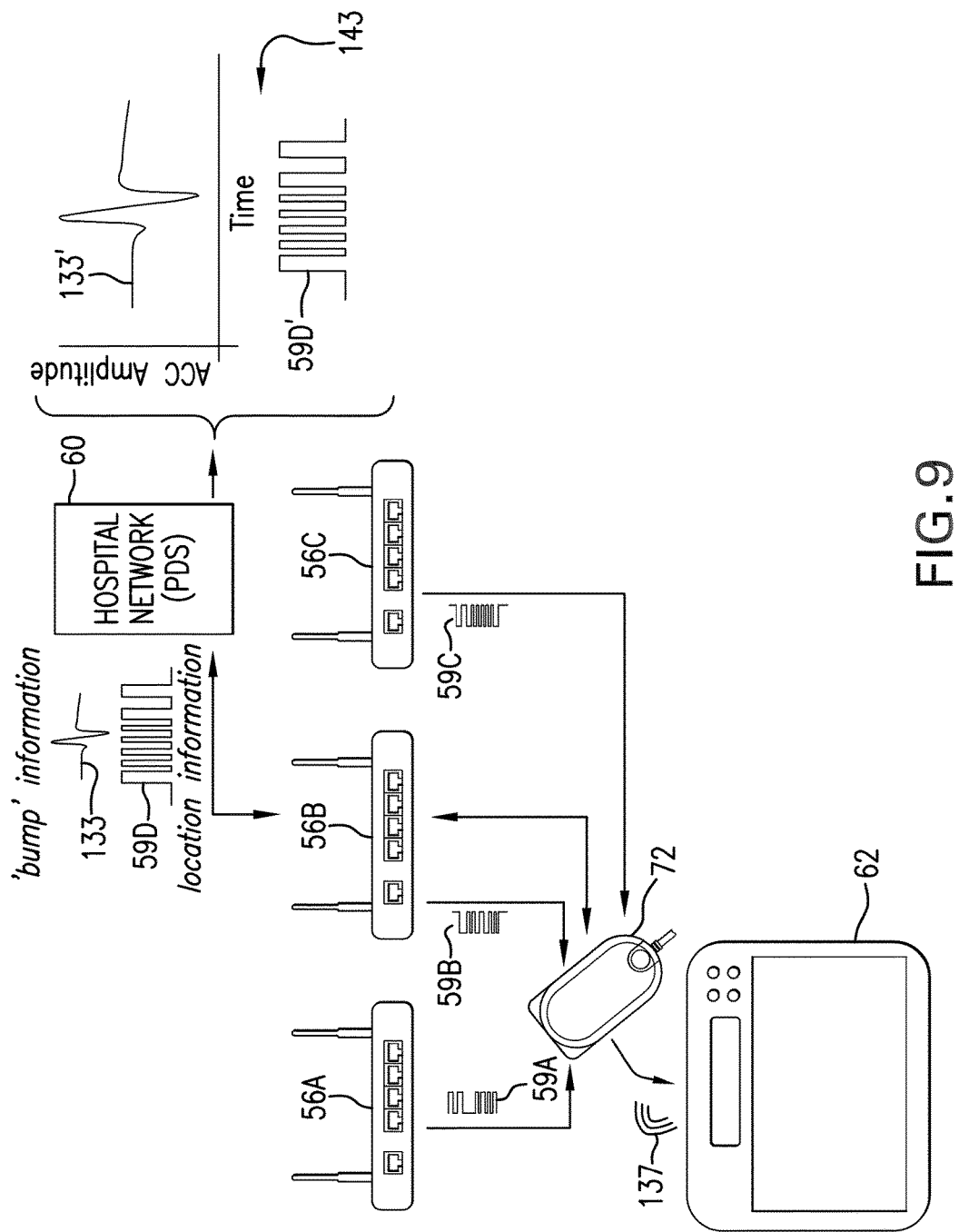
FIG. 9 shows a schematic drawing of a transceiver being 'bumped' against a RVD in order to pair the two devices.

The 'bumping' process described above can also be used for other applications relating to the wrist-worn transceiver. It can be used, for example, to pair the transceiver with an RVD, such as a display located at the patient's bedside, or at a central nursing station. In this embodiment, indicated in FIGS. 9 and 10, a clinician selects a transceiver 72 from the battery charger and brings it near an RVD 62. Before attaching the transceiver 72 to the patient, the clinician 'bumps' it against a hard surface proximal to the RVD 62 (or against the RVD itself) to generate a sharp spike in the ACC waveform 133. The waveform 133 is similar in shape to that generated when two transceivers are swapped with the bumping process, as described above. The RVD's location needs to be determined in order to pair it with the transceiver 72. To do this, at a pre-determined time period (e.g. every few minutes) all neighboring wireless access points 56A, 56B, 56C transmit a 'location beacon' 59A, 59B, 59C to the transceiver, which is received and used to calculate a value for signal strength (typically characterized by an 'RSSI value') between the transceiver 72 and the respective access point 56A, 56B, 56C. The transceiver concatenates values for RSSI and identifiers for the access points into a single 'location packet' 59D, which it then transmits along with the ACC waveform 133 and an identifying code describing the transceiver (not shown in the figure) through a single access point 56B to the PDS 60. The PDS 60 receives the location packet 56D and parses it to arrive at RSSI values for the three wireless access points 56A, 56B, 56C within wireless range of the transceiver 72. In other embodiments, the individual access points 56A, 56B, 56C determine RSSI values characterizing the signal strength between them and the transceiver, and send these as individual packets to the PDS. Software on the PDS then concatenates these packets to determine signals similar to those included in the location packet.

Figure 10:
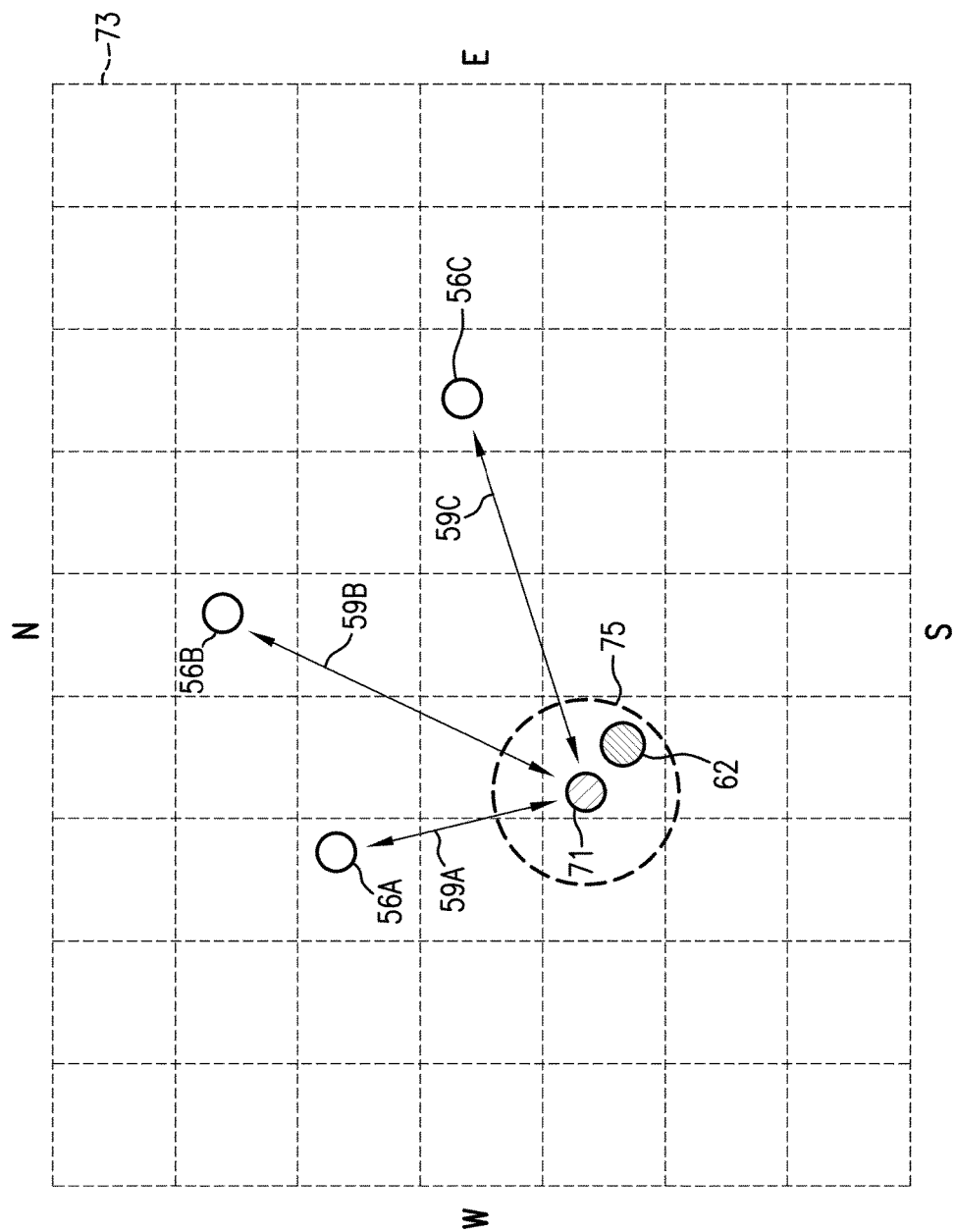
FIG. 10 shows a map indicating how the transceiver and RVD of FIG. 9 are paired to each other.

Referring to FIG. 10, location-determining software operating on the PDS triangulates the signals, along with known locations of each wireless access point 56A, 56B, 56C, to determine an approximate location 71 of the transceiver 72. The known locations of the access points are stored within a map grid 73 in a computer memory associated with the location-determining software. The transceiver's approximate location typically has an accuracy of 1-3 m. Using the map grid 73, the software then processes the approximate location 71 and a known location of any RVD 62 lying within a pre-determined radius 75. Typically the pre-determined radius is 3-5 m. If the location of the RVD 62 lies within the pre-determined radius 75, the RVD 62 is automatically 'paired' with the transceiver 72. Once paired, the RVD 62 then displays any follow-on waveform, motion, and vital sign information sent by the transceiver.

In related embodiments, the location-determining software described above uses triangulation algorithms to determine the patient's current and historical location. Such a process can be used to monitor and locate a patient in distress, and is described, for example, in the following issued patent, the contents of which are incorporated herein by reference: WIRELESS, INTERNET-BASED, MEDICAL DIAGNOSTIC SYSTEM (U.S. Pat. No. 7,396,330). If triangulation is not possible, the location-determining software may simply use proximity to a wireless access point (as determined from the strength of an RSSI value) to estimate the patient's location. Such a situation would occur if signals from at least three wireless access points were not available. In this case, the location of the patient is estimated with an accuracy of about 5-10 m. In embodiments, the RVD may be a central nursing station that displays vital sign, motion-related properties (e.g. posture and activity level) and location information from a group of patients. Such embodiments are described in the following co-pending patent application, the contents of which are fully incorporated herein by reference: BODY-WORN VITAL SIGN MONITOR (U.S. Ser. No. 12/560,077, filed Sep. 15, 2009). In other embodiments, the location-determining software determines the location of a patient-worn transceiver, and automatically pairs it to a RVD located nearby (e.g. within a pre-determined radius, such as that shown in FIG. 10). In this way, the patient's information can be displayed on different RVDs as they roam throughout the hospital.

In embodiments, the patient's location can be analyzed relative to a set of pre-determined boundaries (e.g. a 'geofence') to determine if they have wandered into a restricted area. Or their speed can be determined from their time-dependent location, and then analyzed relative to a pre-determined parameter to determine if they are walking too fast. In general, any combination of location, motion-related properties, vital signs, and waveforms can be collectively analyzed with software operating on either the transceiver or PDS to monitor the patient. Patients can be monitored, for example, in a hospital, medical clinic, outpatient facility, or the patient's home.

In the embodiments described above, location of the transceiver can be determined using off-the-shelf software packages that operate on the PDS. Companies that provide such software include, for example, by Cisco Systems (170 West Tasman Drive, San Jose, Calif. 93134; www.cisco.com), Ekahau (12930 Saratoga Avenue, Suite B-8, Saratoga, Calif. 95070; www.ekahau.com), and others.

In still other embodiments, software operating on the transceiver puts it into a 'sleep mode' when it is not attached to the patient. This way the transceiver can determine and transmit a location packet even when it is not used for patient monitoring. Using the above-described location-determining software, this allows the transceiver's location to be determined and then analyzed if it has been lost, misplaced, or stolen. For example, the transceiver's serial number can be entered into the software and then used to send a 'ping' the transceiver. The transceiver responds to the ping by collecting and transmitting a location packet as described above. Or the location of all unused transceivers can be automatically rendered on a separate interface. In still other embodiments, the location-determining software can transmit a packet to a specific transceiver (e.g. one that is stolen) to disable it from operating further.

In other embodiments, the 'bumping' process described above can be used for a variety of applications involving the body-worn monitor, wrist-worn transceiver, PDS, and RVD. In embodiments, for example, one or more 'bumps' of a transceiver can modulate the ACC waveform, which is then processed and analyzed to initiate a specific application. Applications include turning the transceiver on/off; attaching sensors to the transceiver; pairing the transceiver with a hand-held device (e.g. a cellular phone or personal digital assistant) over a peer-to-peer connection (using, e.g., 802.11 or 802.15.4); pairing the transceiver with a printer connected to a hospital network to print data stored in its computer memory; associating the transceiver with a specific clinician; and initiating display of a particular GUI. In general, the 'bumping' process can be used to initiate any application that can also be initiated with icons on the GUI.

Annotating the Medical Record Using the Wrist-Worn Transceiver

Figure 11:
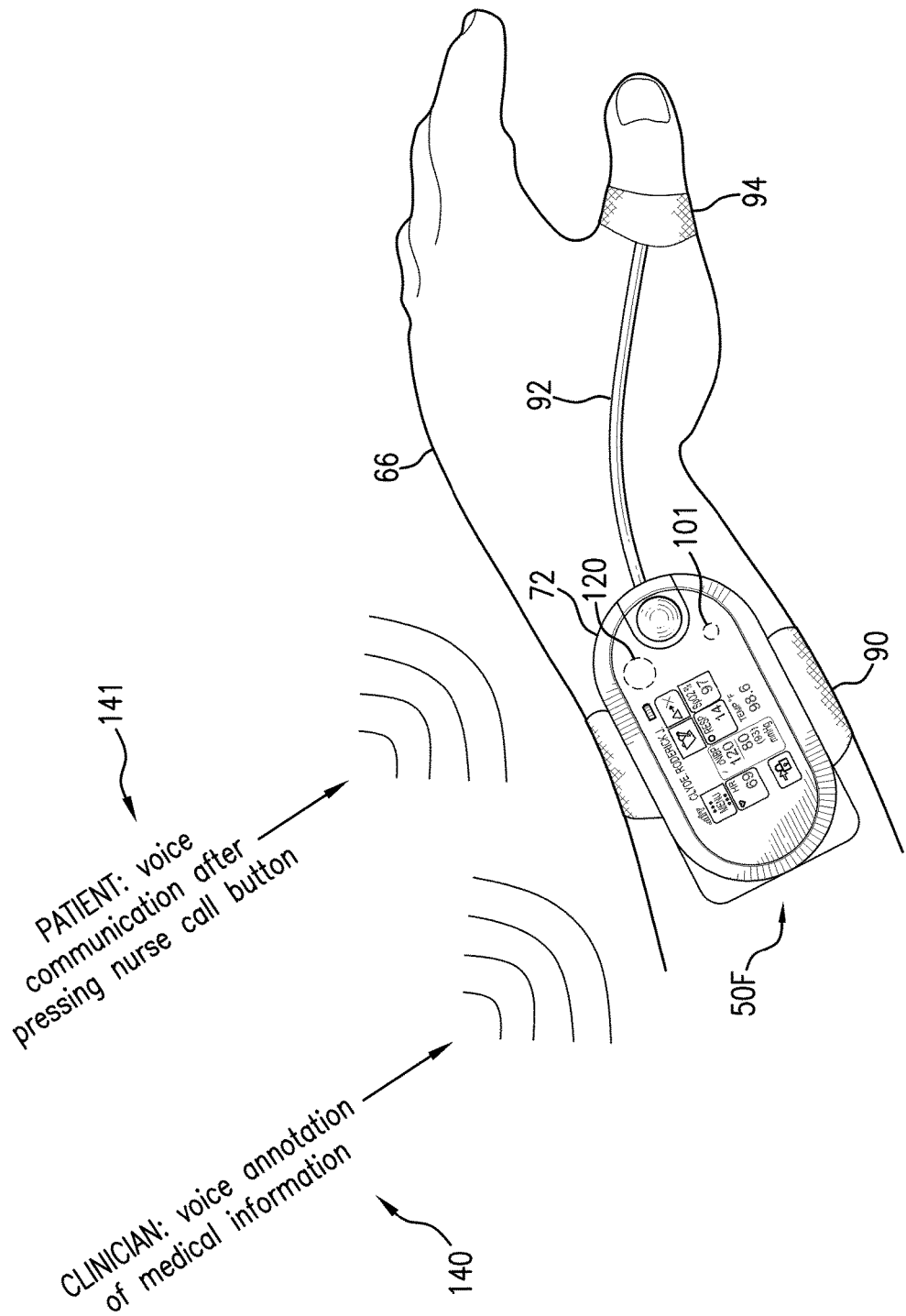
FIG. 11 shows a schematic drawing of the wrist-worn transceiver of FIG. 1 being used for voice annotation of a patient's vital sign data.
Figure 12:
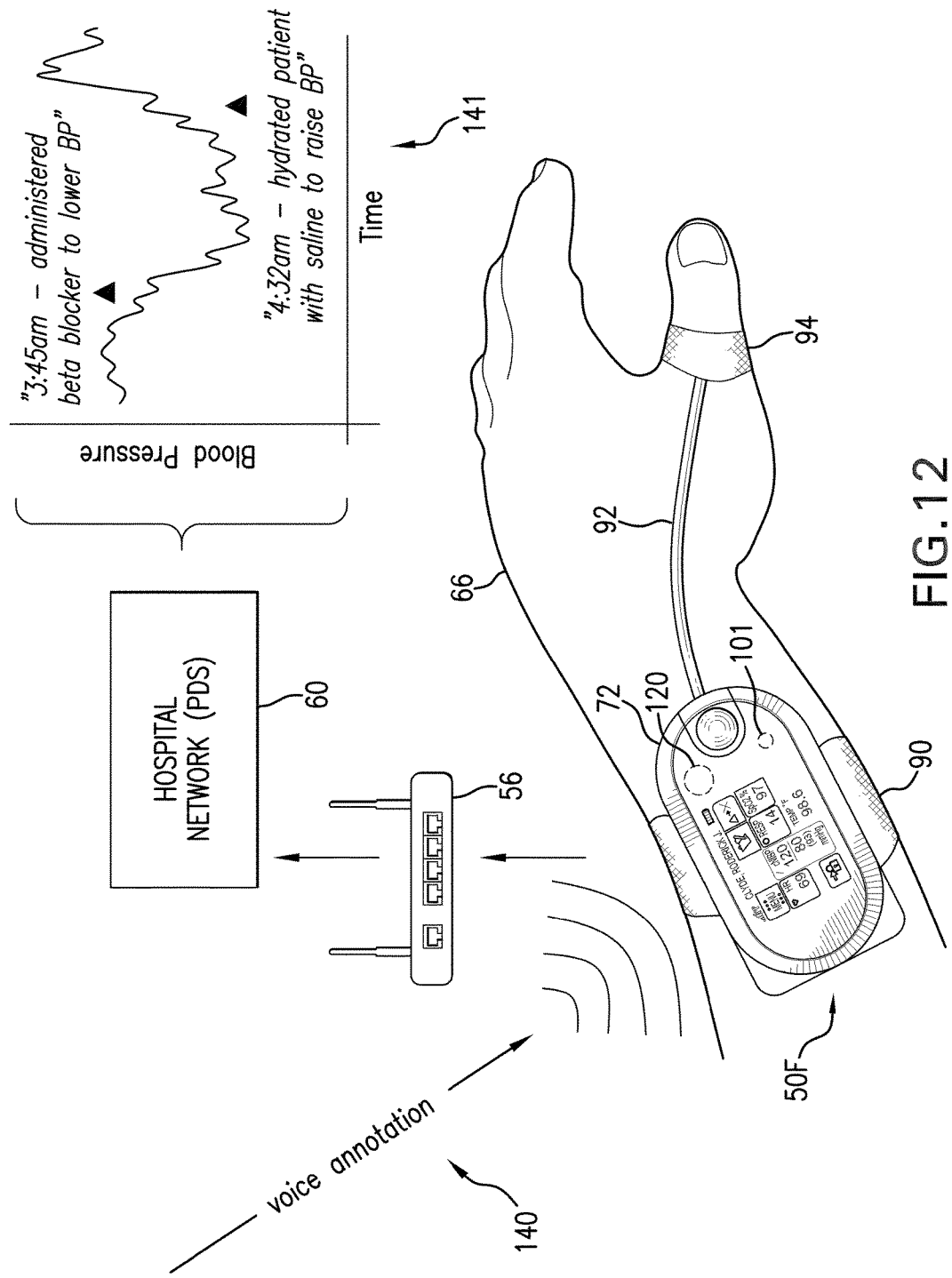
FIG. 12 shows a schematic drawing of the wrist-worn transceiver of FIG. 11 wirelessly transmitting voice annotations to the PDS for analysis.
Figure 13:
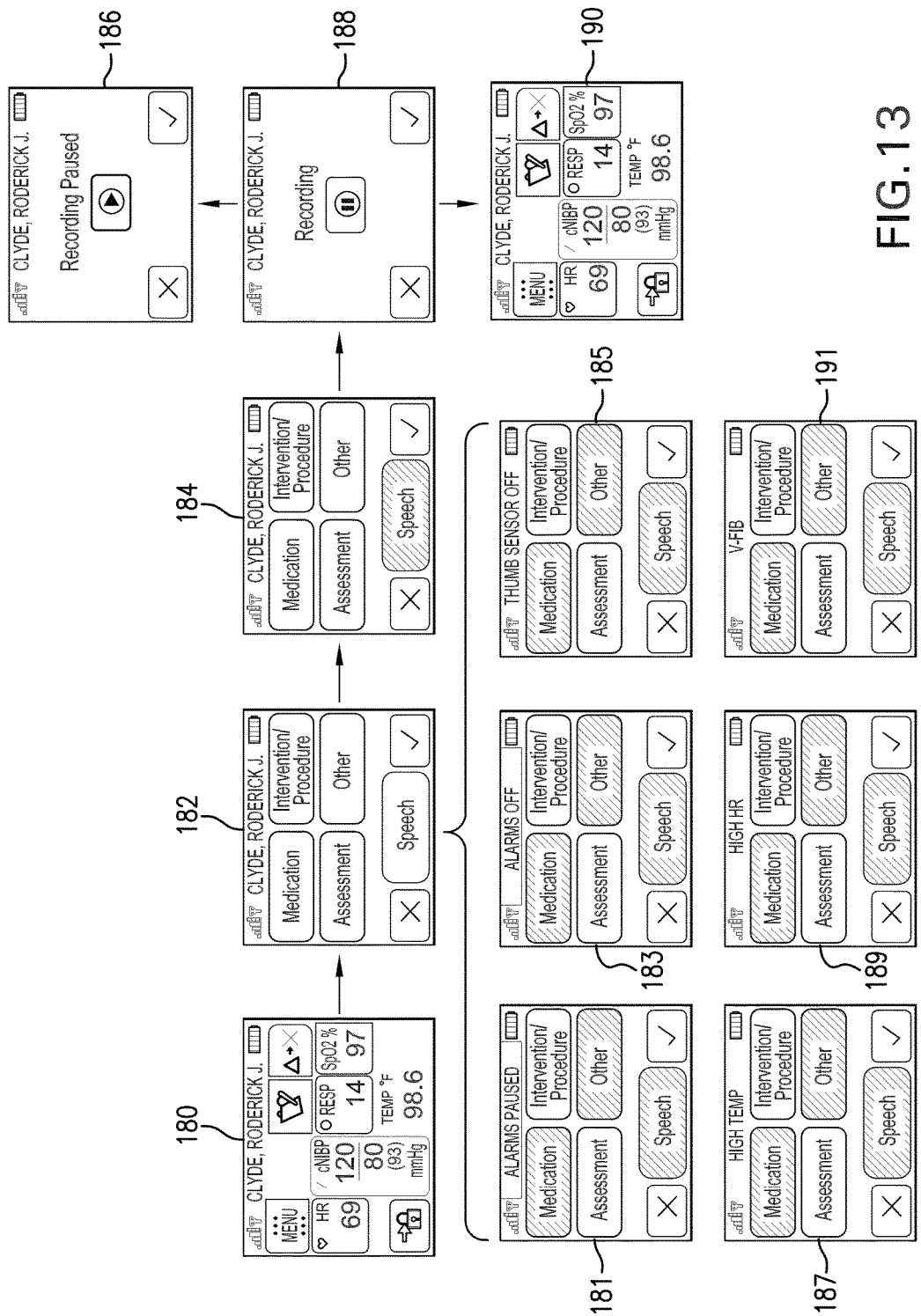
FIG. 13 shows screen captures from a GUI used to guide a clinician through the voice annotation methodology of FIGS. 11 and 12.

FIGS. 11-13 show how the wrist-worn transceiver can be used to communicate audible information from both the patient and a clinician. Audible information from the clinician 140 can be used, for example, to annotate vital sign information collected with the body-worn monitor. Audible information from the patient 141 can be transmitted to a clinician (e.g. a nurse working at a central station) to alert the clinician of a problem. In both applications, the transceiver 72 is attached to the patient's wrist 66 as described above and used to measure vital signs and waveform information. Audible information is received by a microphone 101 mounted on a circuit board within the transceiver. A speaker 120 mounted to the same circuit board enunciates voice information to the patient. In these and other voice-related applications, voice information is digitized by an internal analog-to-digital converter within the transceiver, and then wirelessly transmitted through a hospital's wireless network using conventional VOIP protocols. Systems that operate these protocols are marketed, for example, by Cisco Systems (170 West Tasman Drive, San Jose, Calif. 93134; www.cisco.com), Skype (22/24 Boulevard Royal, 6e etage, L-2449, Luxembourg; www.skype.com), and others.

FIG. 12 describes the annotation process in more detail. In this case, the transceiver 72 within the body-worn monitor is attached to the patient's wrist 66 to measure the patient's vital signs (e.g. blood pressure). During the measurement process, the clinician uses the GUI 50F to activate an 'annotation' function which enables the transceiver to receive audible signals 140 which are used, for example, to annotate different medications administered to the patient. After the annotation function is activated, the clinician orally describes the medications. The microphone 101 within the transceiver 72 detects the voice signals, digitizes them with associated hardware, and then sends them and an associated time/date sample using a VOIP protocol through an access point 56 and to a PDS located within the hospital network 60. Vital signs are transmitted before and after the annotation function is activated, and are stored along with the annotation in a computer memory associated with the PDS. Typically these data are stored within a hospital's EMR.

As shown in graph 141, annotated vital sign data can be viewed afterwards to determine, for example, how a patient responds to specific medications. In this case, administration of a beta blocker as a means of lowering the patient's blood pressure is recorded on the graph by a written description of the annotation, along with an icon (a black triangle) indicating when it occurred in time. To generate the written description the PDS requires software that performs a speech-to-text conversion. Such software is available, for example, from Nuance Systems (1 Wayside Road, Burlington, Mass. 01803; www.nuance.com). Similarly, the graph 141 shows a second annotation indicating that the patient was hydrated with saline to increase their blood pressure.

FIG. 13 shows a series of screens within the GUI 50F that are used to control the annotation process. As described above, to annotate medical information the clinician taps an icon located in the upper right-hand portion of screen 180. This action readies the voice recording features within the transceiver. Tapping the annotation icon drives the transceiver to render a second screen 182 that includes the type of annotation, e.g. audible content relating to medication, a specific intervention or procedure, a medical assessment, or another subject. Typically annotations are delivered as audible speech, in which case the 'Speech' button is tapped, as shown in screen 184. Alternatively the annotation can be text or numerical; these can be typed in, e.g., using a 'soft' keyboard on the transceiver, or scanned in using the transceiver's barcode scanner. The annotations can also be associated with an alarm condition, such as those shown on screens 181, 183, 185, 187, 189, 191. Prior to recording an annotation, the GUI renders a screen 188 that, once tapped, initiates the recording. The recording can also be paused using screen 186. After it is complete, the clinician taps the 'checkbox' on the screen 188, thus saving the recording. It is then sent to the PDS as shown in FIG. 12, and used to annotate the patient's medical information.

Other forms of annotation are also possible with the transceiver. For example, it can include a small CCD camera that allows images of the patient or their body (e.g. a wound) to be captured and used to annotate the medical information. In other applications, a barcode printed on medication administered to the patient can be scanned by the transceiver's barcode scanner, and the information encoded therein can be used to annotate vital sign information. In other embodiments, the transceiver can integrate with other equipment in the hospital room (e.g. an infusion pump, ventilator, or patient-controlled anesthesia pump) through a wired or wireless connection, and information from this equipment can be collected and transmitted to the PDS in order to annotate the vital sign information. In other embodiments, text annotations can be stored on the PDS, and then edited afterwards by the clinician.

Other GUI Applications

Figure 14:
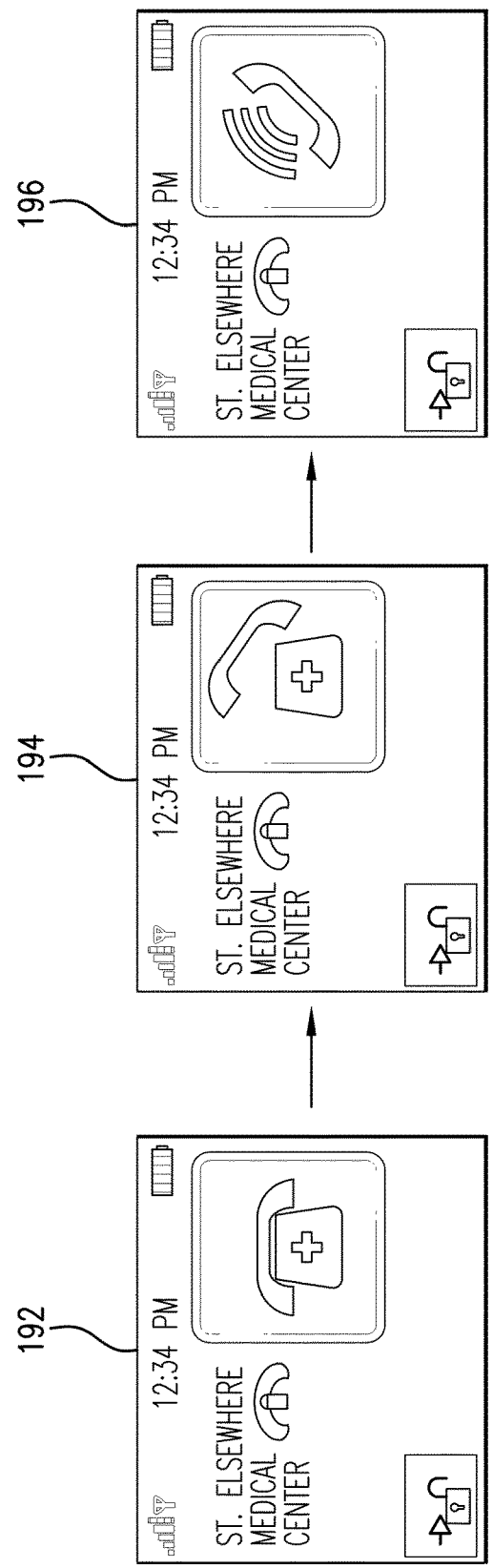
FIG. 14 shows screen captures from a GUI used when the wrist-worn transceiver functions as a two-way communicator between the patient and a clinician.

As shown in FIGS. 11 and 14, the speaker 120 and microphone 101 within the transceiver 72, combined with VOIP software operating on the hospital network, can also function as a nurse call system that communicates both distress signals and voice information. Here, the transceiver enables two-way communication between the patient and a remote clinician. During this application, the transceiver typically operates the 'patient GUI', shown schematically in FIG. 3 and in more detail in FIG. 14. Here, the GUI shows a single screen 192 that indicates a nurse call function with an icon showing a telephone. When the patient taps on the telephone the transceiver initiates a call to a pre-programmed IP address, corresponding, e.g., to a computer at a central nursing station or a VOIP-enabled phone. Alternatively the transceiver can call a pre-programmed phone number corresponding to a telephone. While the call is being place the GUI renders a screen 194 that shows the telephone's receiver being off the hook. A third screen 196 indicates that the patient is connected to the clinician. The call is terminated when the patient finishes talking to the clinician and taps the screen. Alternatively, the transceiver can include software that detects that no further voice communications are taking place, and then uses this information to terminate the call. In embodiments, the entire call can be stored in a computer memory on either the transceiver or the PDS.

The GUI operating on the wrist-worn transceiver's touchpanel display can render several other interfaces that facilitate patient monitoring in the hospital. For example, referring to FIG. 15, the GUI can be used to monitor the patient's pain level, a parameter often considered by clinicians to be as important as vital signs for characterizing a patient. The GUI 200 shown in the figure features a simple series of icons that provide a relative indication of the patient's pain level. An index value of 0 (corresponding to a 'happy' face) indicates a low level of pain; an index value of 10 (corresponding to a 'sad' face) indicates a high level of pain. During a measurement, the patient simply touches the icon that best characterizes their pain level. The numerical value corresponding to this level is then wirelessly transmitted back to the PDS and stored in the patient's EMR. The GUI, for example, may be automatically rendered periodically (e.g. every hour) on the transceiver to continuously monitor the patient's pain level. In other embodiments, the GUI could render a graphical display that provides a more sophisticated metric for determining the patient's pain, such as the McGill Pain Questionnaire. This system described in the following journal article, the contents of which are incorporated herein by reference: 'The McGill Pain Questionnaire: Major Properties and Scoring Methods', Melzak, *Pain,* 1:277-299 (1975).

Figure 15:
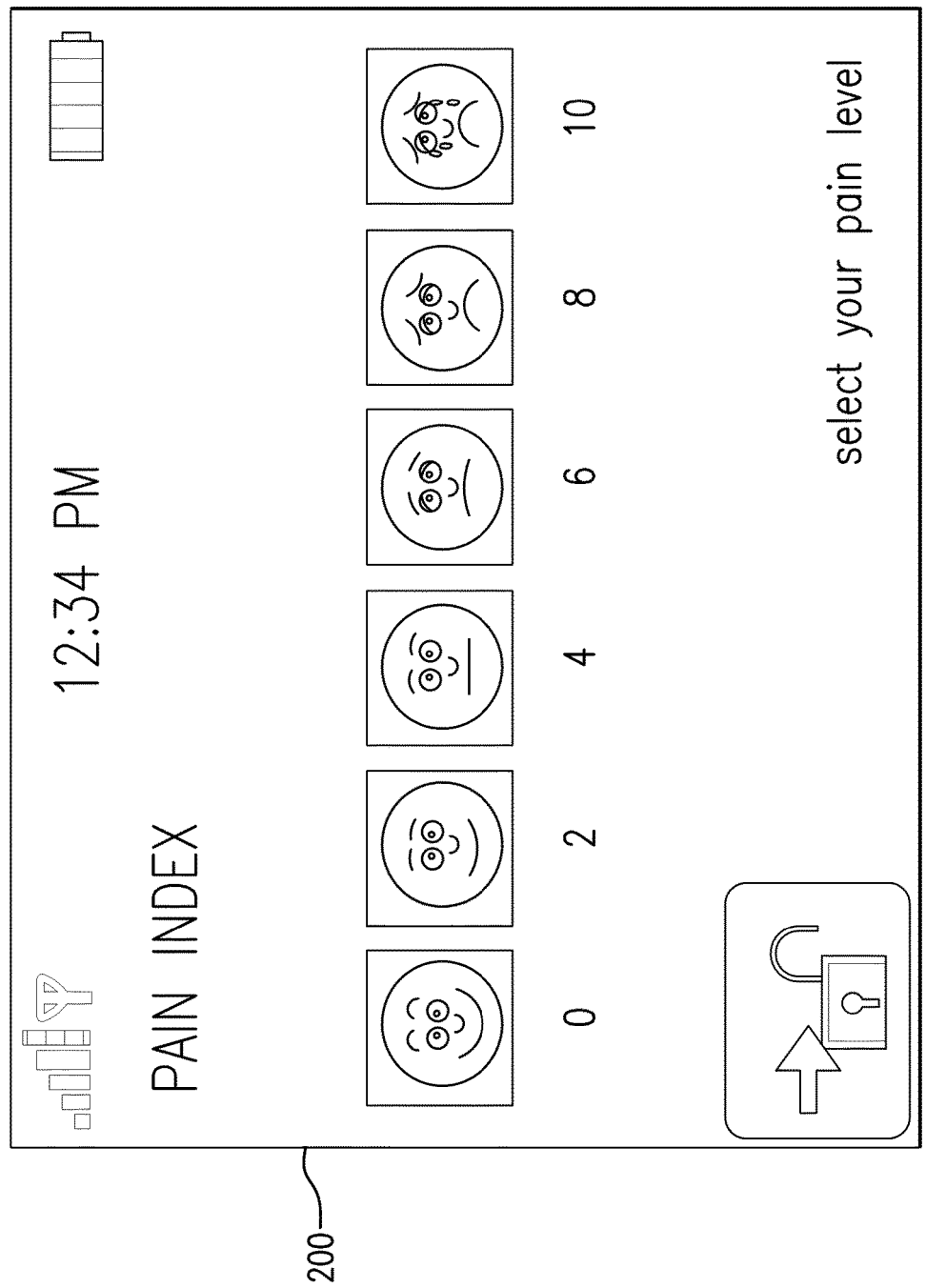
FIG. 15 shows a screen capture from a GUI used to render a 'pain index' on the wrist-worn transceiver.
Figure 16:
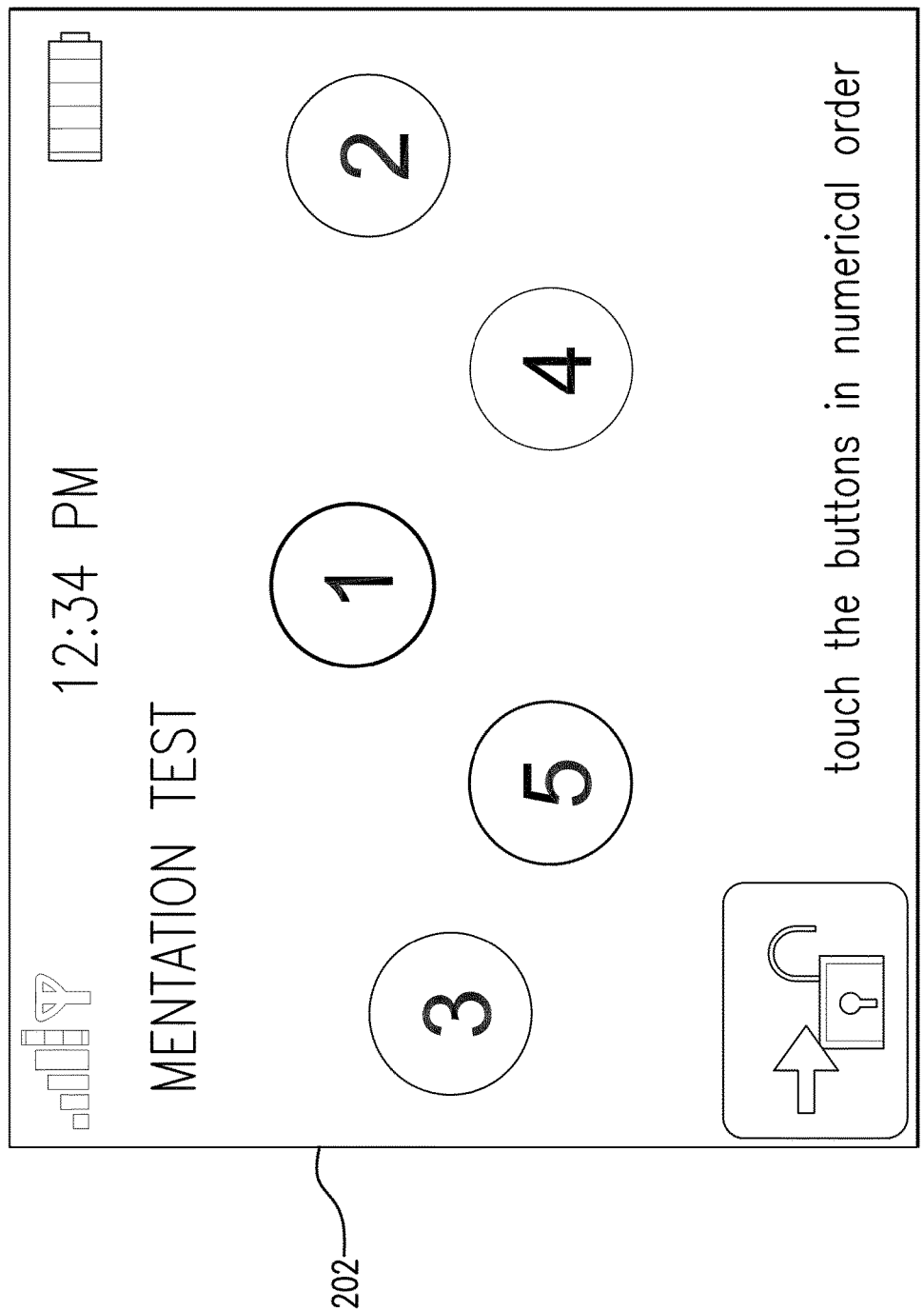
FIG. 16 shows a screen capture from a GUI used to render a mentation test on the wrist-worn transceiver.

In a similar manner, the GUI can be used to gauge the patient's level of mentation, i.e. mental activity. Mentation has been consistently shown to be a valuable tool for diagnosing a patient, but is typically determined empirically by a clinician during a check-up or hospital visit. Such a diagnosis is somewhat arbitrary and requires the clinician to meet face-to-face with the patient, which is often impractical. But with the wrist-worn transceiver, diagnosis of mentation can be made automatically at the patient's bedside without a clinician needing to be present. FIG. 16, for example, shows a GUI 202 that provides a simple 'mentation test' for the patient to complete. In this case, the mentation test involves a graphical representation of a series of non-sequential numbers. The patient completes this test by tapping on the numbers rendered by the touchpanel display in their numerical order. An algorithm then 'scores' the test based on accuracy and the time required to complete it. Once determined, the score is wirelessly transmitted back to the PDS, and then stored in the patient's EMR. Other simple tests with varying complexity can be used in place of that shown in FIG. 16. The tests can vary depending on the specific mentation function to be tested. For example, unique tests can be generated for patients with head injuries, cardiac patients, patients in severe pain, Alzheimer's patients, etc. In all cases, the tests are designed to make a quantitative assessment of the patient's mental status; the transceiver sends a numerical value representing this parameter and an identifier for the test back to the EMR for analysis. The transceiver can be programmed so that the GUI 202 for the mentation test, like the GUI 200 for pain level shown in FIG. 15, is automatically rendered at basically any time interval on the touchpanel display. This time interval can be periodic and on an hourly basis, once/day, etc.

Figure 17:
FIG. 17 shows a screen capture from a GUI used to render a photograph of the patient on the wrist-worn transceiver.

As shown in FIG. 17, the transceiver can include a GUI 204 that displays a photograph or video of the patient. The photograph could be taken by a digital camera within the transceiver, or with an external camera and then transferred to the transceiver through a variety of means, e.g. the hospital's wireless network, a peer-to-peer wireless connection, using a non-volatile memory such as an SD card, or even using a data-transfer process initiated by the 'bump' methodology described above. In general, the same means used to port a photograph from a standard digital camera to a personal computer or other device can be used in this application. Once the photograph is received, software on the transceiver displays it in either a default screen (e.g., in place of the 'beating heart' shown in FIGS. 1 and 3), or when the GUI 204 is activated through a tap of a corresponding icon. Displaying the patient's photograph in this manner provides a visual indicator which the clinician can use to correctly identify the patient. In other embodiments, a photograph of someone associated with the patient (e.g. a relative) can also be displayed on the GUI 204. Such an embodiment may be particularly useful for neo-natal hospitals wards, wherein one or more photographs of an infant's parents could be displayed on a transceiver attached to the infant. This way a clinician could check the photograph to ensure that visitors to the neo-natal hospital ward are, in fact, the infant's parents.

Figure 18:
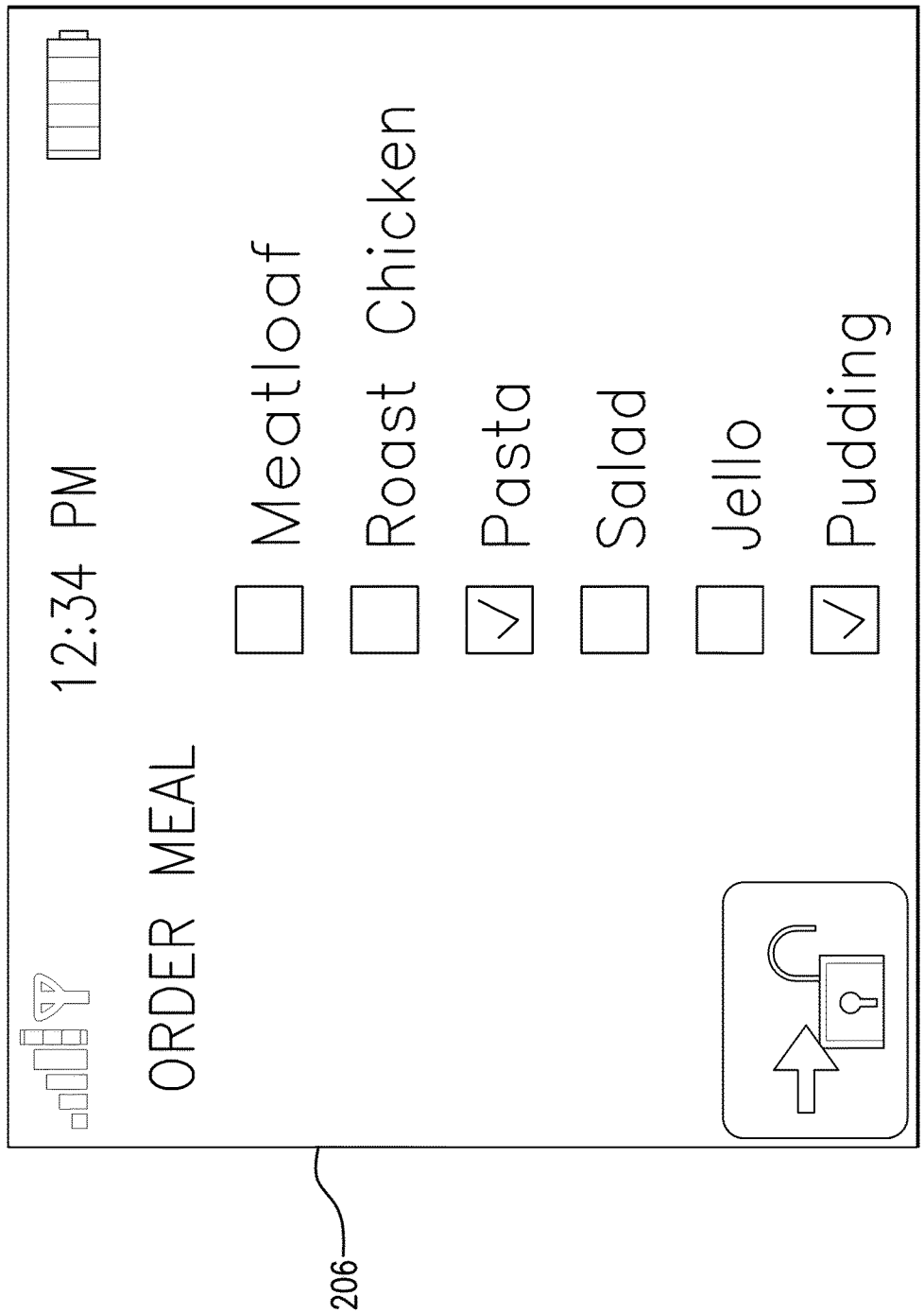
FIG. 18 shows a screen capture from a GUI used to render a food menu on the wrist-worn transceiver.
Figure 19:
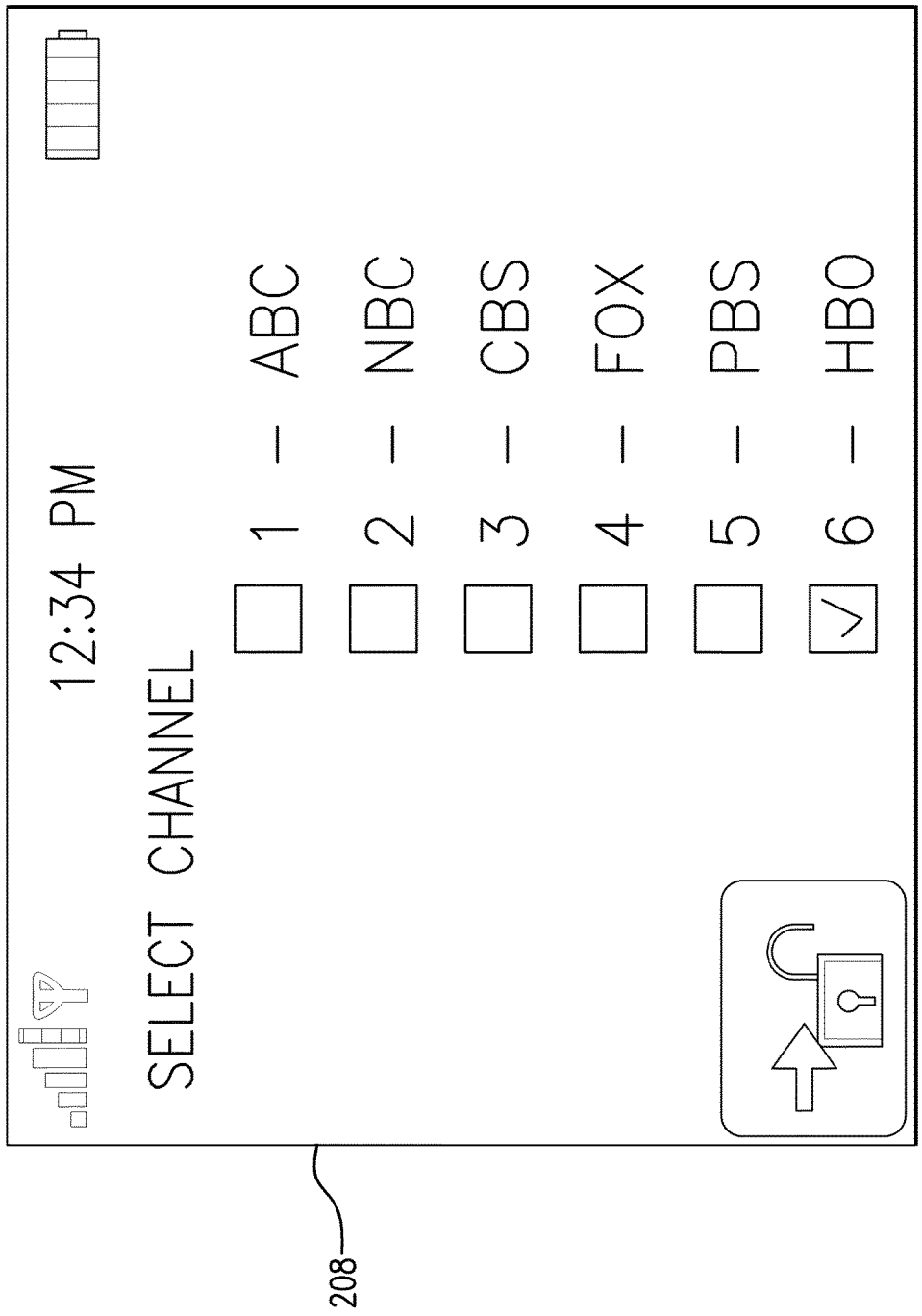
FIG. 19 shows a screen capture from a GUI used to render a menu of television channels on the wrist-worn transceiver.

FIGS. 18 and 19 show other GUIs 206, 208 that can be rendered on the wrist-worn transceiver's display to carry out basic features in the hospital, such as meal ordering (FIG. 18), and changing the channel on a television or computer (FIG. 19). In these cases, the PDS associated with the transceiver receives a packet describing the function at hand (e.g., the meal that has been ordered, or the channel that is desired), and communicates with another software application in the hospital to complete the transaction. This communication, for example, can take place using a XML-based Web Services operation, such as that described in the following patent application, the contents of which are incorporated herein by reference: CUFFLESS BLOOD PRESSURE MONITOR AND ACCOMPANYING WEB SERVICES INTERFACE (U.S. Ser. No. 10/810,237, Filed Mar. 26, 2004). In related embodiments, a GUI similar to that shown in FIG. 19 can be used to order movies, video games, television programs stored on a digital video recorder, books, and music. Content corresponding to these components is typically stored on a remote server, and then accessed using an XML-based operation, as described above.

In yet another application, as shown in FIG. 20, the wrist-worn transceiver 72 and its associated barcode scanner 102 can be used to check medication before it is administered to the patient. In this embodiment, barcodes associated with the patient 63, clinician 65, and the medication 67 are read by the barcode scanner 102 within the transceiver 72. The transceiver then wirelessly transmits decoded barcode information through a local access point 56 and to the PDS connected to the hospital network 60. Using a software program, the PDS analyzes these data and communicates with the patient's record in the hospital EMR 58 to determine if the medication is appropriate for the patient. For example, the software program may check to see if the patient is allergic to the medication, if the dosage is correct, or if the patient has previously exhibited any detrimental side effects that may affect the dosage. In related embodiments, the transceiver may also include a GUI wherein the clinician enters ancillary information, such as the dosage of the medication or demographic information describing the patient, using a 'soft' keypad. Or the GUI may include a simple questionnaire that guides the clinician through the process of checking the medication, and then administering it. In still other embodiments, the infusion pump that delivers the medication may include a wireless connection through the access point 56 to the PDS 60 or to the transceiver 72 to automatically supply information related to the medication to the software program.

Once the software program determines that it is safe to administer the medication, it sends a packet from the PDS 60, through the access point 56, and back to the transceiver 72, which then renders a GUI instructing the clinician to proceed. In other embodiments, the PDS 60 sends the packet through the access point 56 to either a remote computer 62 (e.g. a tablet computer) or a portable device 64 (e.g. a cellular telephone or personal digital assistant).

Form Factor of the Body-Worn Monitor

Figures 21A, 21B:
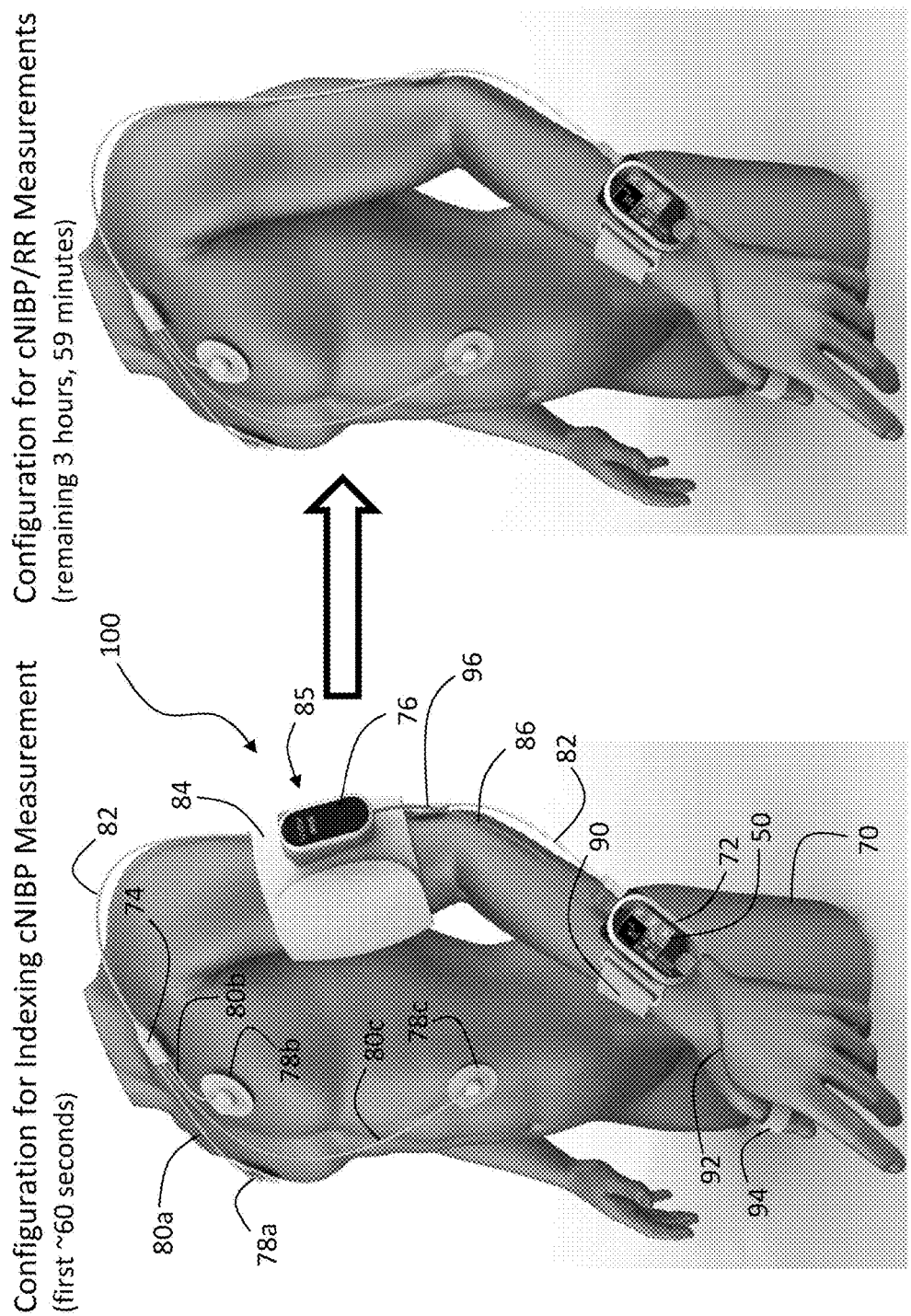
FIGS. 21A and 21B show three-dimensional images of the body-worn monitor of FIG. 4 attached to a patient with and without, respectively, a cuff-based pneumatic system used for a calibrating indexing measurement.

FIGS. 21A and 21B show how the body-worn monitor 100 described above attaches to a patient 70 to measure RR, SpO2, cNIBP, and other vital signs. These figures show two configurations of the system: FIG. 21A shows the system used during the indexing portion of the Composite Technique, and includes a pneumatic, cuff-based system 85, while FIG. 21B shows the system used for subsequent measurements. The indexing measurement typically takes about 60 seconds, and is typically performed once every 4-8 hours. Once the indexing measurement is complete the cuff-based system 85 is typically removed from the patient. The remainder of the time the monitor 100 performs the RR, HR, SpO2 and cNIBP measurements.

The body-worn monitor 100 features a wrist-worn transceiver 72, described in more detail in FIGS. 22A and 22B, featuring a touch panel interface 73 that displays the various GUIs described above and in FIG. 24. A wrist strap 90 affixes the transceiver 72 to the patient's wrist like a conventional wristwatch. A flexible cable 92 connects the transceiver 72 to an optical sensor 94 that wraps around the base of the patient's thumb. During a measurement, the optical sensor 94 generates a time-dependent PPG waveform which is processed along with an ECG to measure cNIBP, SpO2, and, in some applications, RR. To determine ACC waveforms the body-worn monitor 100 features three separate accelerometers located at different portions on the patient's arm and chest. The first accelerometer is surface-mounted on a circuit board in the wrist-worn transceiver 72 and measures signals associated with movement of the patient's wrist. As described above, this motion can also be indicative of that originating from the patient's fingers, which will affect the SpO2 measurement. The second accelerometer is included in a small bulkhead portion 96 included along the span of the cable 82. During a measurement, a small piece of disposable tape, similar in size to a conventional bandaid, affixes the bulkhead portion 96 to the patient's arm. In this way the bulkhead portion 96 serves two purposes: 1) it measures a time-dependent ACC waveform from the mid-portion of the patient's arm, thereby allowing their posture and arm height to be determined as described in detail above; and 2) it secures the cable 82 to the patient's arm to increase comfort and performance of the body-worn monitor 100, particularly when the patient is ambulatory. The third accelerometer is mounted in the sensor module 74 that connects through cables 80*a-c* to ECG electrodes 78*a-c*. Signals from these sensors are then digitized, transmitted through the cable 82 to the wrist-worn transceiver 72, where they are processed with an algorithm as described above to determine RR.

The cuff-based module 85 features a pneumatic system 76 that includes a pump, valve, pressure fittings, pressure sensor, manifold, analog-to-digital converter, microcontroller, and rechargeable Li:ion battery. During an indexing measurement, the pneumatic system 76 inflates a disposable cuff 84 and performs two measurements according to the Composite Technique: 1) it performs an inflation-based measurement of oscillometry and measurement of a corresponding OSC waveform to determine values for SYS, DIA, and MAP; and 2) it determines a patient-specific relationship between PTT and MAP. These measurements are described in detail in the co-pending patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which are incorporated herein by reference.

The cuff 84 within the cuff-based pneumatic system 85 is typically disposable and features an internal, airtight bladder that wraps around the patient's bicep to deliver a uniform pressure field. During the indexing measurement, pressure values are digitized by the internal analog-to-digital converter, and sent through a cable 86 according to a CAN protocol, along with SYS, DIA, and MAP blood pressures, to the wrist-worn transceiver 72 for processing as described above. Once the cuff-based measurement is complete, the cuff-based module 85 is removed from the patient's arm and the cable 86 is disconnected from the wrist-worn transceiver 72. cNIBP is then determined using PTT, as described in detail above.

To determine an ECG, the body-worn monitor 100 features a small-scale, three-lead ECG circuit integrated directly into the sensor module 74 that terminates an ECG cable 82. The ECG circuit features an integrated circuit that collects electrical signals from three chest-worn ECG electrodes 78*a-c* connected through cables 80*a-c*. As described above, the ECG electrodes 78*a-c* are typically disposed in a conventional Einthoven's Triangle configuration, which is a triangle-like orientation of the electrodes 78*a-c* on the patient's chest that features three unique ECG vectors. From these electrical signals the ECG circuit determines up at least three ECG waveforms, each corresponding to a unique ECG vector, which are digitized using an analog-to-digital converter mounted proximal to the ECG circuit and sent through the cable 82 to the wrist-worn transceiver 72 according to the CAN protocol. There, the ECG and PPG waveforms are processed to determine the patient's blood pressure. HR and RR are determined directly from the ECG waveform using known algorithms, such as those described above. More sophisticated ECG circuits (e.g. five and twelve-lead systems) can plug into the wrist-worn transceiver to replace the three-lead system shown in FIGS. 21A and 21B.

FIGS. 22A, 22B show three-dimensional views of the wrist-worn transceiver 72 before and after receiving cables 82, 86, 89 from sensors worn on the patient's upper arm and torso, as well as the cable 92 that connects to the optical sensor. The transceiver 72 is sealed in a water-proof plastic casing 117 featuring electrical interconnects (not shown in the figure) on its bottom surface that interface to the terminal ends 111, 119*a-c* of cables 82, 86, 89, 92 leading to the monitor's various sensors. The electrical interconnects support serial communication through the CAN protocol, described in detail herein, particularly with reference to FIG. 25. During operation, the transceiver's plastic casing 117 snaps into a plastic housing 106, which features an opening 109 on one side to receive the terminal end 111 of the cable 92 connected to the optical sensor. On the opposing side the plastic housing 106 features three identical openings 104*a-c* that receive the terminal ends 119*a-c* of cables 82, 86, 89 connected to the ECG and accelerometer systems (cable 82), the pneumatic cuff-based system (cable 86), and ancillary systems (cable 89) described above. In addition to being waterproof, this design facilitates activities such as cleaning and sterilization, as the transceiver contains no openings for fluids common in the hospital, such as water and blood, to flow inside. During a cleaning process the transceiver 72 is simply detached from the plastic housing 106 and then cleaned.

The transceiver 72 attaches to the patient's wrist using a flexible strap 90 which threads through two D-ring openings in the plastic housing 106. The strap 90 features mated Velcro patches on each side that secure it to the patient's wrist during operation. A touchpanel display 50 renders the various GUIs described above.

Figure 25:
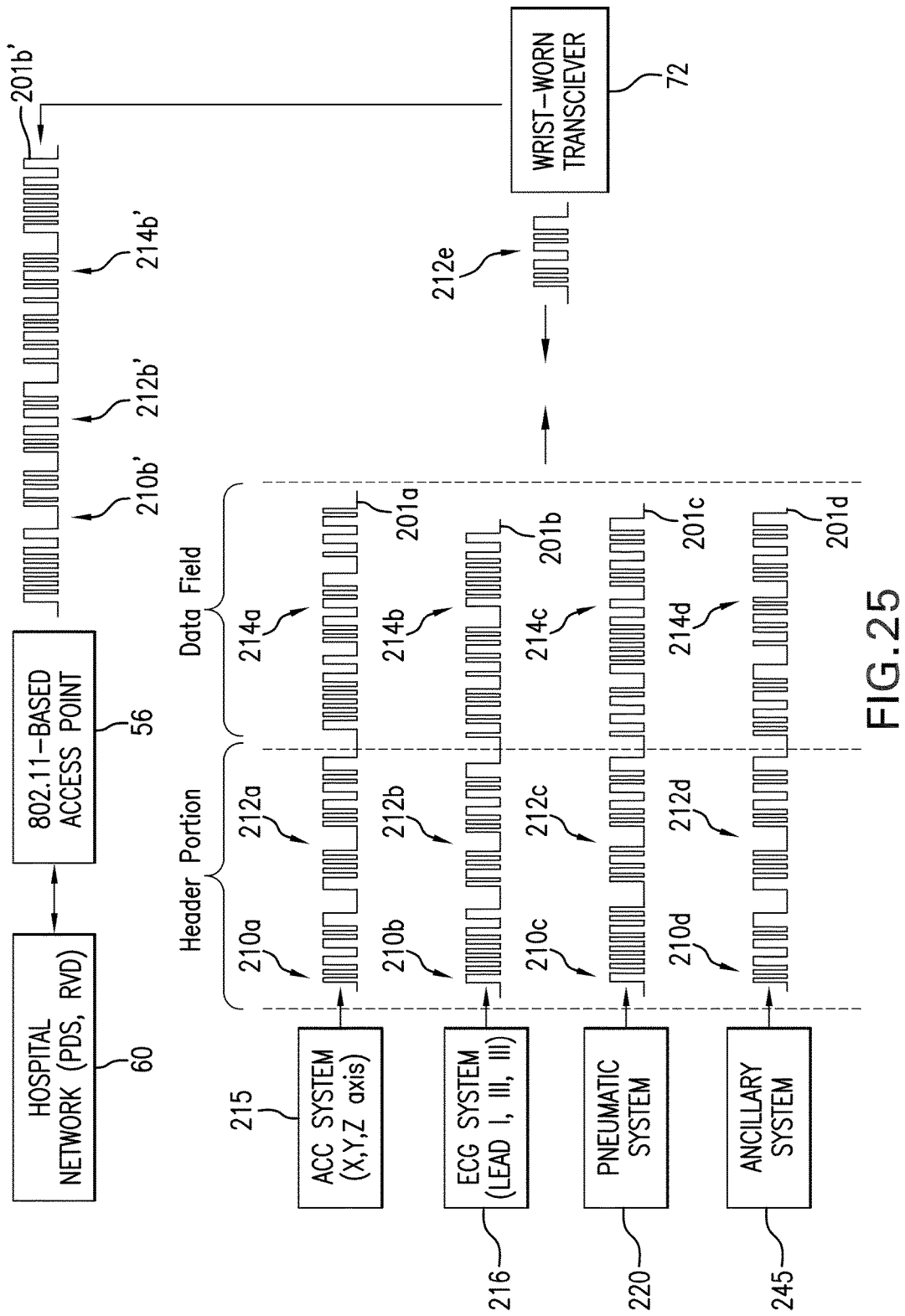
FIG. 25 shows a schematic drawing of the ACC, ECG, pneumatic, and auxiliary systems of the body-worn monitor communicating over the CAN protocol with the wrist-worn transceiver.

The electrical interconnects on the transceiver's bottom side line up with the openings 104*a-c*, and each supports the CAN protocol to relay a digitized data stream to the transceiver's internal CPU, as described in detail with reference to FIG. 25. This allows the CPU to easily interpret signals that arrive from the monitor's body-worn sensors, and means that these connectors are not associated with a specific cable. Any cable connecting to the transceiver 72 can be plugged into any opening 104*a-c*. As shown in FIG.

22A, the first opening 104a receives the cable 82 that transports digitized ECG waveforms determined from the ECG circuit and electrodes, and digitized ACC waveforms measured by accelerometers in the cable bulkhead and the bulkhead portion associated with the ECG cable 82.

The second opening 104b receives the cable 86 that connects to the pneumatic cuff-based system used for the pressure-dependent indexing measurement. This connector receives a time-dependent pressure waveform delivered by the pneumatic system to the patient's arm, along with values for SYS, DIA, and MAP determined during the indexing measurement. The cable 86 unplugs from the opening 104b once the indexing measurement is complete, and is plugged back in after approximately 4-8 hours for another indexing measurement.

The final opening 104c can be used for an auxiliary device, e.g. a glucometer, infusion pump, body-worn insulin pump, ventilator, or end-tidal $CO_2$ monitoring system. As described with reference to FIG. 25, digital information generated by these systems will include a header that indicates their origin so that the CPU can process them accordingly.

Measuring and Displaying Time-Dependent Physiological Signals

Figure 23B:
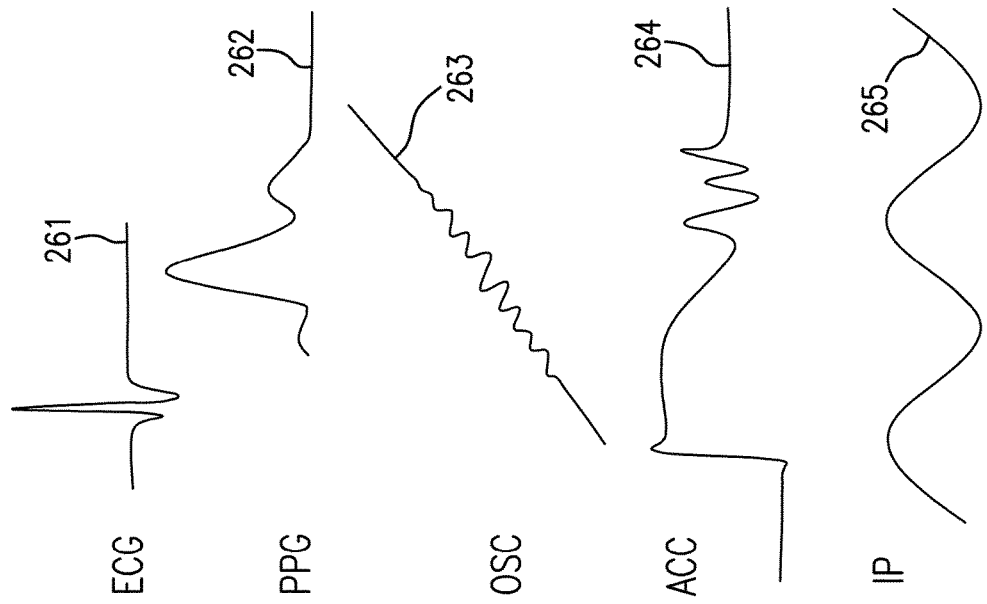
FIG. 23B shows graphs of time-dependent ECG, PPG, OSC, ACC, and IP waveforms generated with the body-worn monitor and sensors of FIG. 23A.
Figure 23A:
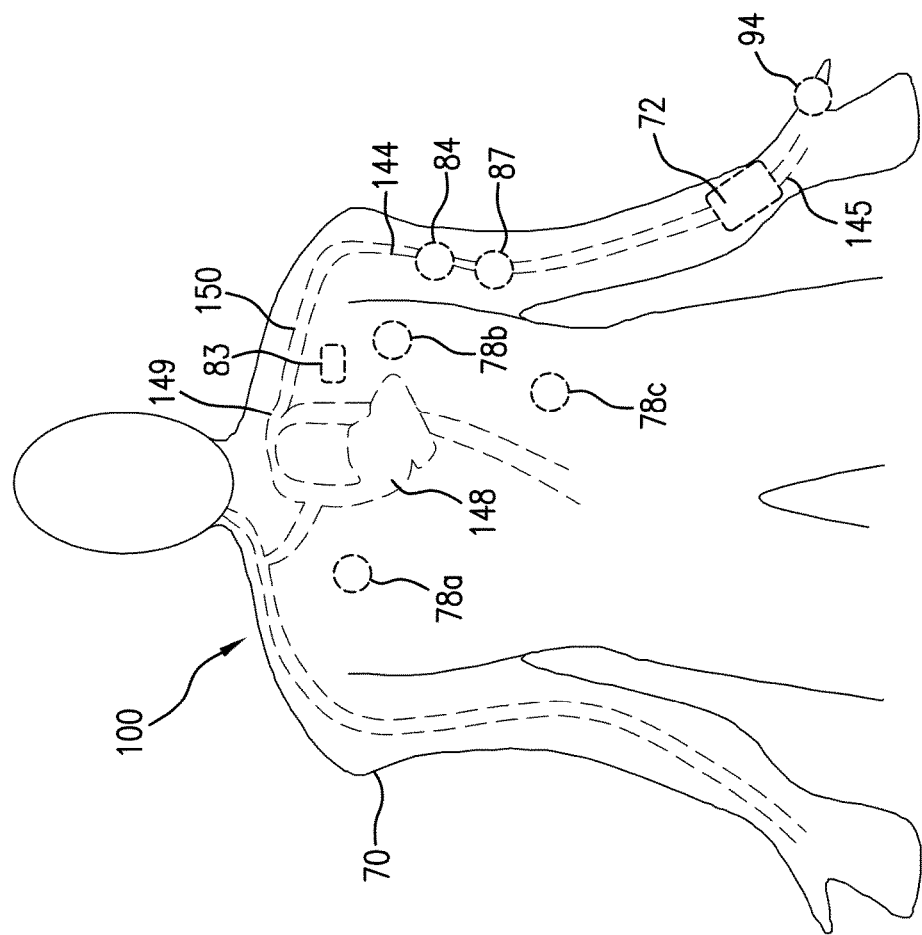
FIG. 23A shows a schematic drawing of a patient wearing the body-worn monitor of FIG. 21B and its associated sensors.

FIGS. 23A and 23B show how a network of sensors 78a-c, 83, 84, 87, 94 within the body-worn monitor 100 connect to a patient 70 to measure time-dependent ECG 261, PPG 262, OSC 263, ACC 264, and RR 265 waveforms. These, in turn, yield the patient's vital signs and motion parameters. Each waveform 261-265 relates to a unique physiological characteristic of the patient 70. For example, each of the patient's heartbeats generates electrical impulses that pass through the body near the speed of light, along with a pressure wave that propagates through the patient's vasculature at a significantly slower speed. Immediately after the heartbeat, the pressure wave leaves the heart 148 and aorta 149, passes through the subclavian artery 150 to the brachial artery 144, and from there through the radial and ulnar arteries 145 to smaller arteries in the patient's fingers. Three disposable electrodes 78a-c attached to the patient's chest measure unique electrical signals which pass to a single-chip ECG circuit 83 that terminates a distal end of the ECG cable. Typically, these electrodes attach to the patient's chest in a conventional 'Einthoven's triangle' configuration featuring three unique 'vectors', each corresponding to a different lead (e.g. LEAD 1, II, II). Related configurations can also be used when five and twelve-lead ECG systems are used in place of the three-lead system, as described above with reference to FIGS. 21A, 21B. Within the ECG circuit 83 signals are processed using an amplifier/filter circuit and analog-to-digital converter to generate a digital ECG waveform 261 corresponding to each lead. The ECG waveform 261 features a sharp, well-defined QRS complex corresponding to each heartbeat; this marks the initiation of the patient's cardiac cycle. Heart rate is determined directly from the ECG waveform 261 using known algorithms, such as those described in the following journal article, the contents of which are incorporated herein by reference: 'ECG Beat Detection Using Filter Banks', Afonso et al., *IEEE Trans. Biomed Eng.*, 46:192-202 (1999).

To generate an IP waveform 265, one of the ECG electrodes in the circuit 78a is a 'driven lead' that injects a small amount of modulated current into the patient's torso. A second, non-driven electrode 78c, typically located on the opposite side of the torso, detects the current, which is further modulated by capacitance changes in the patient's chest cavity resulting from breathing. Further processing and filtering of the IP waveforms 265 yields respiratory rate. Respiration can also be determined using an adaptive filtering approach that processes both the IP waveform and ACC waveform 264, as described in more detail in the following co-pending patent application, the contents of which are incorporated herein by reference: BODY-WORN MONITOR FOR MEASURING RESPIRATION RATE (U.S. Ser. No. 12/559,419, Filed Sep. 14, 2009).

The optical sensor 94 features two LEDs and a single photodetector that collectively measure a time-dependent PPG waveform 262 corresponding to each of the LEDs. The sensor and algorithms for processing the PPG waveforms are described in detail in the following co-pending patent application, the contents of which have been previously incorporated herein by reference: BODY-WORN PULSE OXIMETER (U.S. Ser. No. 12/559,379; filed Sep. 14, 2009). The waveform 262 represents a time-dependent volumetric change in vasculature (e.g. arteries and capillaries) that is irradiated with the sensor's optical components. Volumetric changes are induced by a pressure pulse launched by each heartbeat that travels from the heart 148 to arteries and capillaries in the thumb according to the above-describe arterial pathway. Pressure from the pressure pulse forces a bolus of blood into this vasculature, causing it to expand and increase the amount of radiation absorbed, and decrease the transmitted radiation at the photodetector. The pulse shown in the PPG waveform 262 therefore represents the inverse of the actual radiation detected at the photodetector. It follows the QRS complex in the ECG waveform 261, typically by about one to two hundred milliseconds. The temporal difference between the peak of the QRS complex and the foot of the pulse in the PPG waveform 262 is the PTT, which as described in detail below is used to determine blood pressure according to the Composite Technique. PTT-based measurements made from the thumb yield excellent correlation to blood pressure measured with a femoral arterial line. This provides an accurate representation of blood pressure in the central regions of the patient's body.

Each accelerometer generates three time-dependent ACC waveforms 264, corresponding to the x, y, and z-axes, which collectively indicate the patient's motion, posture, and activity level. The body-worn monitor, as described above, features three accelerometers that attach to the patient: one in the wrist-worn transceiver 72, one in the ECG circuit 83, and one near the bicep 87 that is included in the cable connecting these two components. The frequency and magnitude of change in the shape of the ACC waveform 264 indicate the type of motion that the patient is undergoing. For example, the waveform 264 can feature a relatively time-invariant component indicating a period of time when the patient is relatively still, and a time-variant component when the patient's activity level increases. Magnitudes of both components will depend on the relationship between the accelerometer and a gravity vector, and can therefore be processed to determine time-invariant features, such as posture and arm height. A frequency-dependent analysis of the time-variant components yields the type and degree of patient motion. Analysis of ACC waveforms 264 is described in detail in the above-mentioned patent applications, the contents of which have been fully incorporated herein by reference.

The OSC waveform 263 is generated from the patient's brachial artery 144 with the pneumatic system and a cuff-based sensor 84 during the pressure-dependent portion of the Composite Technique. It represents a time-dependent pressure which is applied to the brachial artery during inflation and measured by a digital pressure sensor within the pneumatic system. The waveform 263 is similar to waveforms measured during deflation by conventional oscillometric blood pressure monitors. During a measurement, the pressure waveform 263 increases in a mostly linear fashion as pressure applied by the cuff 84 to the brachial artery 144 increases. When it reaches a pressure slightly below the patient's diastolic pressure, the brachial artery 144 begins to compress, resulting in a series time-dependent pulsations caused by each heartbeat that couple into the cuff 84. The pulsations modulate the OSC waveform 263 with an amplitude that varies in a Gaussian-like distribution, with maximum modulation occurring when the applied pressure is equivalent to the patient's MAP. The pulsations can be filtered out and processed using digital filtering techniques, such as a digital bandpass filter that passes frequencies ranging from 0.5-20 Hz. The resulting waveform can be processed to determine SYS, DIA, and MAP, as is described in detail in the above-referenced patent applications, the contents of which have been previously incorporated herein by reference. The cuff 84 and pneumatic system are removed from the patient's bicep once the pressure-dependent component of the Composite Technique is complete.

The high-frequency component of the OSC waveform 263 (i.e. the pulses) can be filtered out to estimate the exact pressure applied to the patient's brachial artery during oscillometry. According to the Composite Technique, PTT measured while pressure is applied will gradually increase as the brachial artery is occluded and blood flow is gradually reduced. The pressure-dependent increase in PTT can be fit with a model to estimate the patient-specific relationship between PTT and blood pressure. This relationship, along with SYS, MAP, and DIA determined from the OSC waveform during inflation-based oscillometry, is used during the Composite Technique's pressure-free measurements to determine blood pressure directly from PTT.

There are several advantages to making the indexing measurement during inflation, as opposed to deflation. Measurements made during inflation are relatively fast and comfortable compared to those made during deflation. Inflation-based measurements are possible because of the Composite Technique's relatively slow inflation speed (typically 5-10 mmHg/second) and the high sensitivity of the pressure sensor used within the body sensor. Such a slow inflation speed can be accomplished with a small pump that is relatively lightweight and power efficient. Moreover, measurements made during inflation can be immediately terminated once systolic blood pressure is calculated. This tends to be more comfortable than conventional cuff-based measurements made during deflation. In this case, the cuff typically applies a pressure that far exceeds the patient's systolic blood pressure; pressure within the cuff then slowly bleeds down below the diastolic pressure to complete the measurement.

A digital temperature sensor proximal to the ECG circuit 83 measures the patient's skin temperature at their torso. This temperature is an approximation of the patient's core temperature, and is used mostly for purposes related to trending and alarms/alerts.

Figure 24:
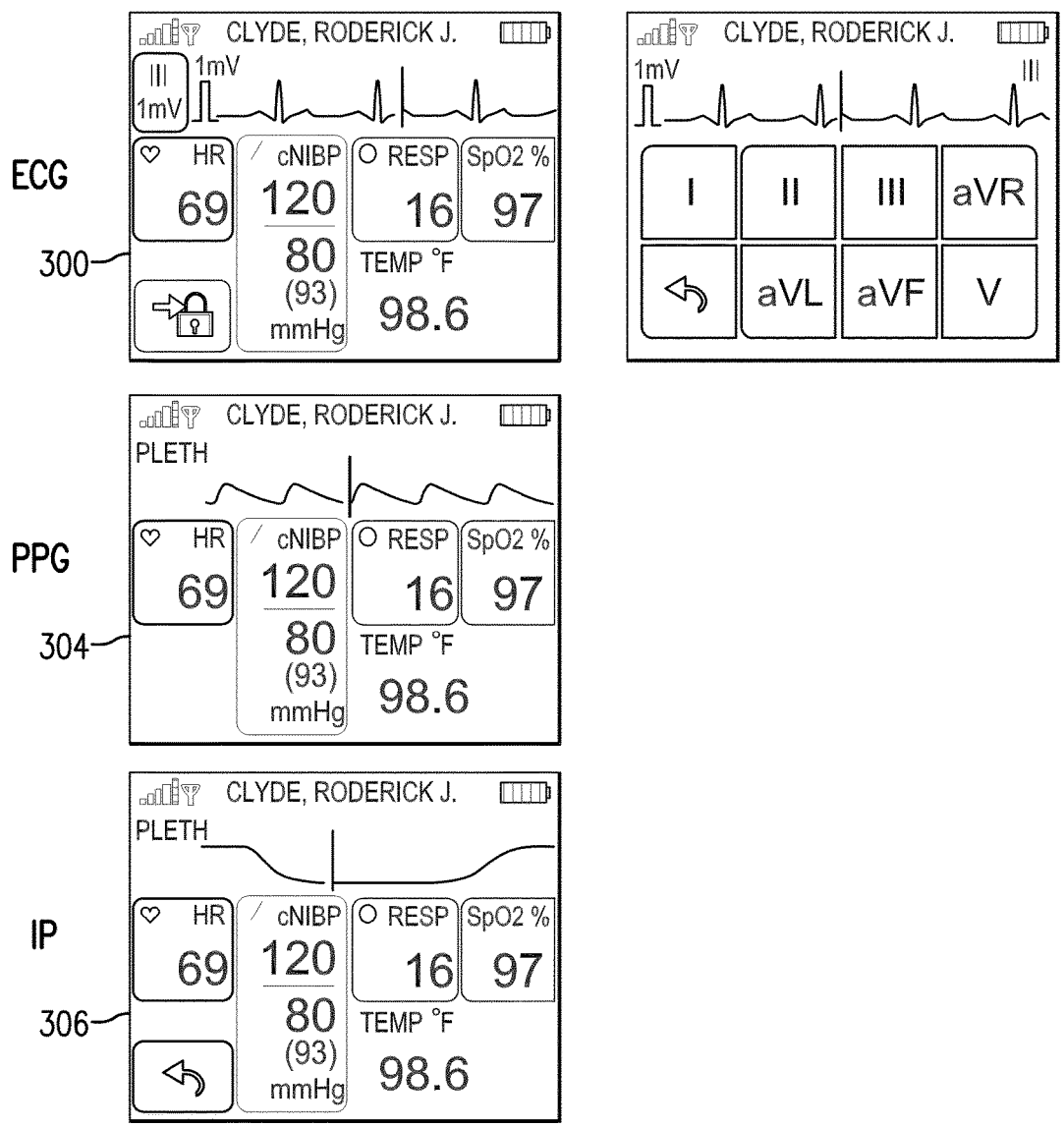
FIG. 24 shows screen captures from a GUI used to render vital signs and ECG, PPG, and IP waveforms on the wrist-worn transceiver.

FIG. 24 shows how the above-described ECG, PPG, and IP waveforms, along with vital signs calculated from them, are rendered using different screens 300, 304, 306, 308 within a GUI. In all cases, the waveforms are displayed with a rolling graphical technique, along with a moving bar that indicates the most current point in time. As per the AAMI/ANSI EC-13 reference standard, the ECG waveforms are displayed alongside a bar that indicates a signal intensity of 1 mV. Screen 308 shows different ECG vectors (corresponding to, e.g., Lead I, II, III, aVR, aVF) that are rendered when the clinician taps the ECG waveform on screen 300, and then the corresponding lead on screen 308. Waveforms for a particular vital sign (e.g. a PPG waveform for the SpO2 measurement; an IP waveform for the RR measurement) are rendered when the clinician taps on the value of the corresponding vital sign. During a measurement both waveforms and the vital signs calculated from them are wirelessly transmitted to the PDS, as described above.

Communicating with Multiple Systems Using the CAN Protocol

As described above, the ECG, ACC, and pneumatic systems within the body-worn system send digitized information to the wrist-worn transceiver through the CAN protocol. FIG. 25 shows a schematic drawing indicating how CAN packets 201a-d, 212a-e transmitted between these systems facilitate communication. Specifically, each of the ACC 215, ECG 216, pneumatic 220, and auxiliary 245 systems include a separate analog-to-digital converter, microcontroller, frequency-generating crystal oscillator (typically operating at 100 kHz), and real-time clock divider that collectively generate and transmit digital data packets 201a-d according to the CAN protocol to the wrist-worn transceiver 72. Each crystal uses the internal real-time clock on the internal microprocessor within the respective system. This allows the microcontroller within each system to be placed in a low-power state in which its real-time operating system (RTOS) dispatch system indicates that it is not ready to run a task. The real-time clock divider is programmed to create an interrupt which wakes up the microcontroller every 2 milliseconds.

The wrist-worn transceiver 72 features a 'master clock' that generates real-time clock 'ticks' at the sampling rate (typically 500 Hz, or 2 ms between samples). Each tick represents an incremented sequence number. Every second, the wrist-worn transceiver 72 transmits a packet 212e over the CAN bus that digitally encodes the sequence number. One of the criteria for accurate timing is that the time delay between the interrupt and the transmission of the synchronizing packet 212e, along with the time period associated with the CAN interrupt service routine, is predictable and stable. During initialization, the remote CAN buses do not sleep; they stay active to listen for the synchronization packet 212e. The interrupt service routine for the synchronization packet 212e then establishes the interval for the next 2 millisecond interrupt from its on-board, real-time crystal to be synchronized with the timing on the wrist-worn transceiver 72. Offsets for the packet transmission and interrupt service delays are factored into the setting for the real-time oscillator to interrupt synchronously with the microprocessor on the wrist-worn transceiver 72. The magnitude of the correction factor to the real-time counter is limited to 25% of the 2 millisecond interval to ensure stability of this system, which represents a digital phase-locked loop.

When receipt of the synchronization packet 212e results in a timing correction offset of either a 0, +1, or −1 count on the remote system's oscillator divider, software running on the internal microcontroller declares that the system is phase-locked and synchronized. At this point, it begins its power-down operation and enables measurement of data as described above.

Each remote system is driven with a 100 kHz clock, and a single count of the divider corresponds to 20 microseconds. This is because the clock divider divides the real-time clock frequency by a factor of 2. This is inherent in the microcontroller to ensure that the clock has a 50% duty cycle, and means the clock can drift+/−20 microseconds before the actual divider chain count will disagree by one count, at which time the software corrects the count to maintain a phase-locked state. There is thus a maximum of 40 microseconds of timing error between data transmitted from the remote systems over the CAN bus. Blood pressure is the one vital sign measured with the body-worn monitor that is calculated from time-dependent waveforms measured from different systems (e.g. PPG and ECG waveforms). For this measurement, the maximum 40-microsecond timing error corresponds to an error of +/−0.04 mmHg, which is well within the error (typically+/−5 mmHg) of the measurement.

In order to minimize power consumption, the wrist-worn transceiver 72 and remote systems 215, 216, 220, 245 power down their respective CAN bus transceivers between data transfers. During a data transfer, each system generates a sequence number based that is included in the synchronization packet 212e. The sequence number represents the interval between data transfers in intervals of 2 milliseconds. It is a factor of 500 (e.g. 2, 4, 5, 10) that is the number of 2 millisecond intervals between transfers on the CAN bus. Each remote system enables its CAN bus during the appropriate intervals and sends its data. When it has finished sending its data, it transmits a 'transmit complete' packet indicating that the transmission is complete. When a device has received the 'transmit complete' packet it can disable its CAN transceiver to further reduce power consumption.

Software in each of the ACC 215, ECG 216, pneumatic 220, and auxiliary 245 systems receive the sequence packet 212e and the corresponding sequence number, and set their clocks accordingly. There is typically some inherent error in this process due to small frequency differences in the crystals (from the ideal frequency of 100 kHz) associated with each system. Typically this error is on the order of microseconds, and has only a small impact on time-dependent measurements, such as PTT, which are typically several hundred milliseconds.

Once timing on the CAN bus is established using the above-described procedure, each of the ACC 215, ECG 216, and pneumatic 220 systems generate time-dependent waveforms that are transmitted in packets 201a-d, each representing an individual sample. Each packet 201a-d features a header portion which includes the sequence number 212a-d and an initial value 210a-d indicating the type of packet that is transmitted. For example, accelerometers used in the body-worn system are typically three-axis digital accelerometers, and generate waveforms along the x, y, and z-axes. In this case, the initial value 210a encodes numerical values that indicate: 1) that the packet contains ACC data; and 2) the axis (x, y, or z) over which these data are generated. Similarly, the ECG system 216 can generate a time-dependent ECG waveform corresponding to Lead I, II, or III, each of which represents a different vector measured along the patient's torso. Additionally, the ECG system 216 can generate processed numerical data, such as heart rate (measured from time increments separating neighboring QRS complexes), respiratory rate (from an internal impedance pneumography component), as well as alarms calculated from the ECG waveform that indicate problematic cardiovascular states such as VTAC, VFIB, and PVCs. Additionally, the ECG system can generate error codes indicating, for example, that one of the ECG leads has fallen off. The ECG system typically generates an alarm/alert, as described above, corresponding to both the error codes and potentially problematic cardiovascular states. In this case, the initial value 210b encodes numerical values that indicate: 1) that the packet contains ECG data; 2) the vector (Lead I, II, or III) corresponding to the ECG data; and 3) an indication if a cardiovascular state such as VTAC, VFIB, or PVCs was detected.

The pneumatic system 220 is similar to the ECG system in that it generates both time-dependent waveforms (i.e. a pressure waveform, measured during oscillometry, characterizing the pressure applied to the arm and subsequent pulsations measured during an oscillometric measurement) and calculated vital signs (SYS, DIA, and MAP measured during oscillometry). In some cases errors are encountered during the oscillometric blood pressure measurement. These include, for example, situations where blood pressure is not accurately determined, an improper OSC waveform, over-inflation of the cuff, or a measurement that is terminated before completion. In these cases the pneumatic system 220 generates a corresponding error code. For the pneumatic system 220 the initial value 210c encodes numerical values that indicate: 1) that the packet contains blood pressure data; 2) an indication that the packet includes an error code.

In addition to the initial values 210a-d, each packet 201a-d includes a data field 214a-d that encodes the actual data payload. Examples of data included in the data fields 214a-d are: 1) sampled values of ACC, ECG, and pressure waveforms; 2) calculated heart rate and blood pressure values; and 3) specific error codes corresponding to the ACC 215, ECG 216, pneumatic 220, and auxiliary 225 systems.

Upon completion of the measurement, the wrist-worn transceiver 72 receives all the CAN packets 201a-d, and synchronizes them in time according to the sequence number 212a-d and identifier 210a-d in the initial portions 216 of each packet. Every second, the CPU updates the time-dependent waveforms and calculates the patient's vital signs and motion-related properties, as described above. Typically these values are calculated as a 'rolling average' with an averaging window ranging from 10-20 seconds. The rolling average is typically updated every second, resulting in a new value that is displayed on the wrist-worn transceiver 72. Each packet received by the transceiver 72 is also wirelessly retransmitted as a new packet 201b' through a wireless access point 56 and to both an PDS and RVD within a hospital network 60. The new packet 201b' includes the same header 210b', 212b' and data field information 214b' as the CAN packets transmitted between systems within the body-worn monitor. Also transmitted are additional packets encoding the cNIBP, SpO2, and processed motion states (e.g. posture, activity level, degree of motion), which unlike heart rate and SYS, DIA, and MAP are calculated by the CPU in the wrist-worn transceiver. Upon receipt of the packet 201b', the RVD displays vital signs, waveforms, motion information, and alarms/alerts, typically with a large monitor that is easily viewed by a clinician. Additionally the PDS can send information through the hospital network (e.g. in the case of an alarm/alert), store information in an internal database, and transfer it to a hospital EMR.

Alternate IT Configurations

Figure 26:
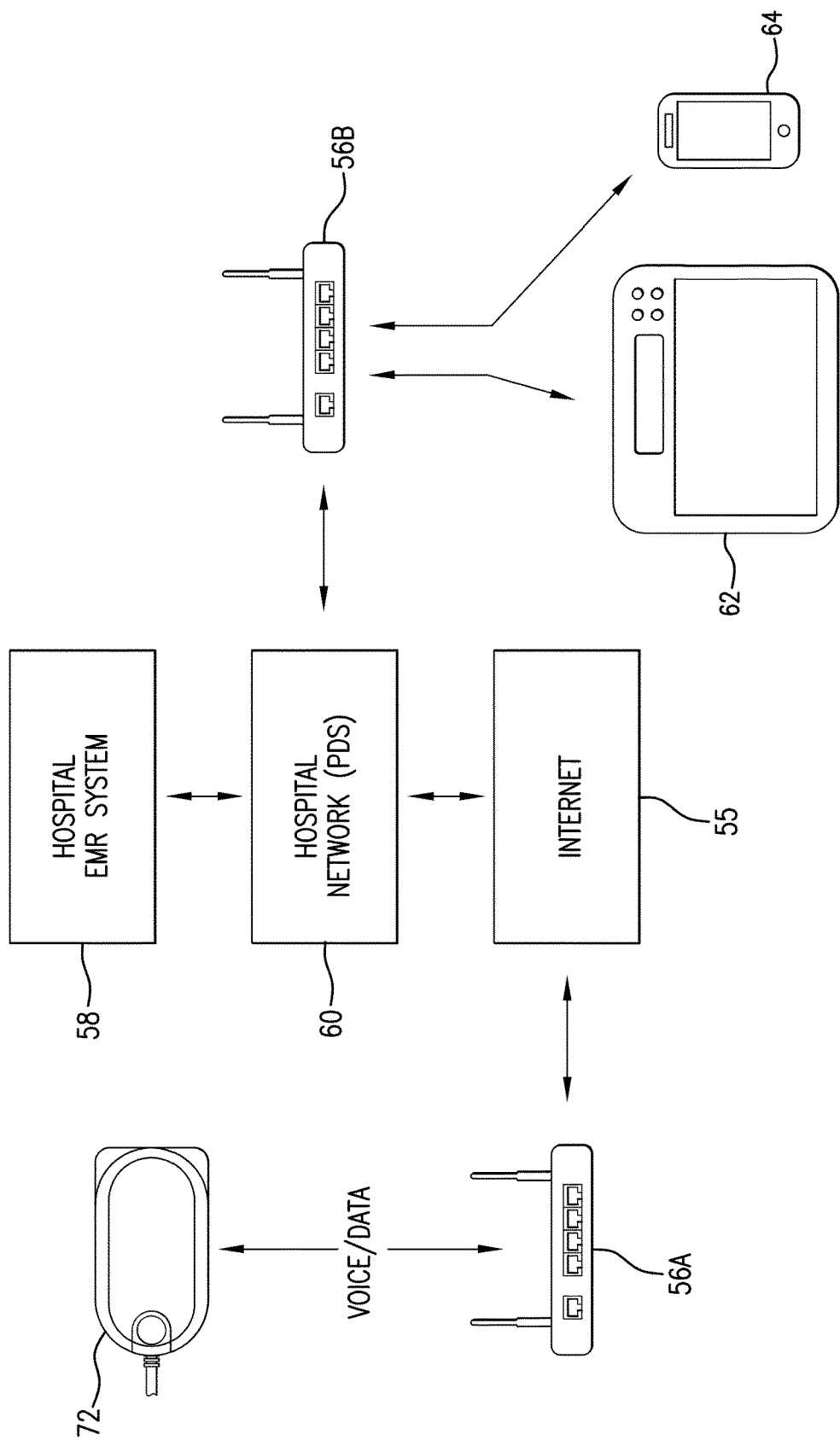
FIG. 26 shows an alternate IT configuration of the invention where the wrist-worn transceiver of FIG. 1 communicates with the PDS through a wireless access point connected to the Internet.

FIG. 26 shows an alternate configuration of the invention wherein the transceiver 72 transmits both voice and data information through a wireless access point 56A and to the Internet 55, and from there to the hospital network and PDS 60. Such a configuration would be used, for example, when the patient is located outside of the hospital (e.g. at home). It allows clinicians to monitor and care for a patient as if they were located in the hospital. Once information arrives at the PDS 60, it can be transferred to the hospital EMR system 58, or through a wireless access point 56B within the hospital to an external computer 62 or a portable device 64.

Figure 27:
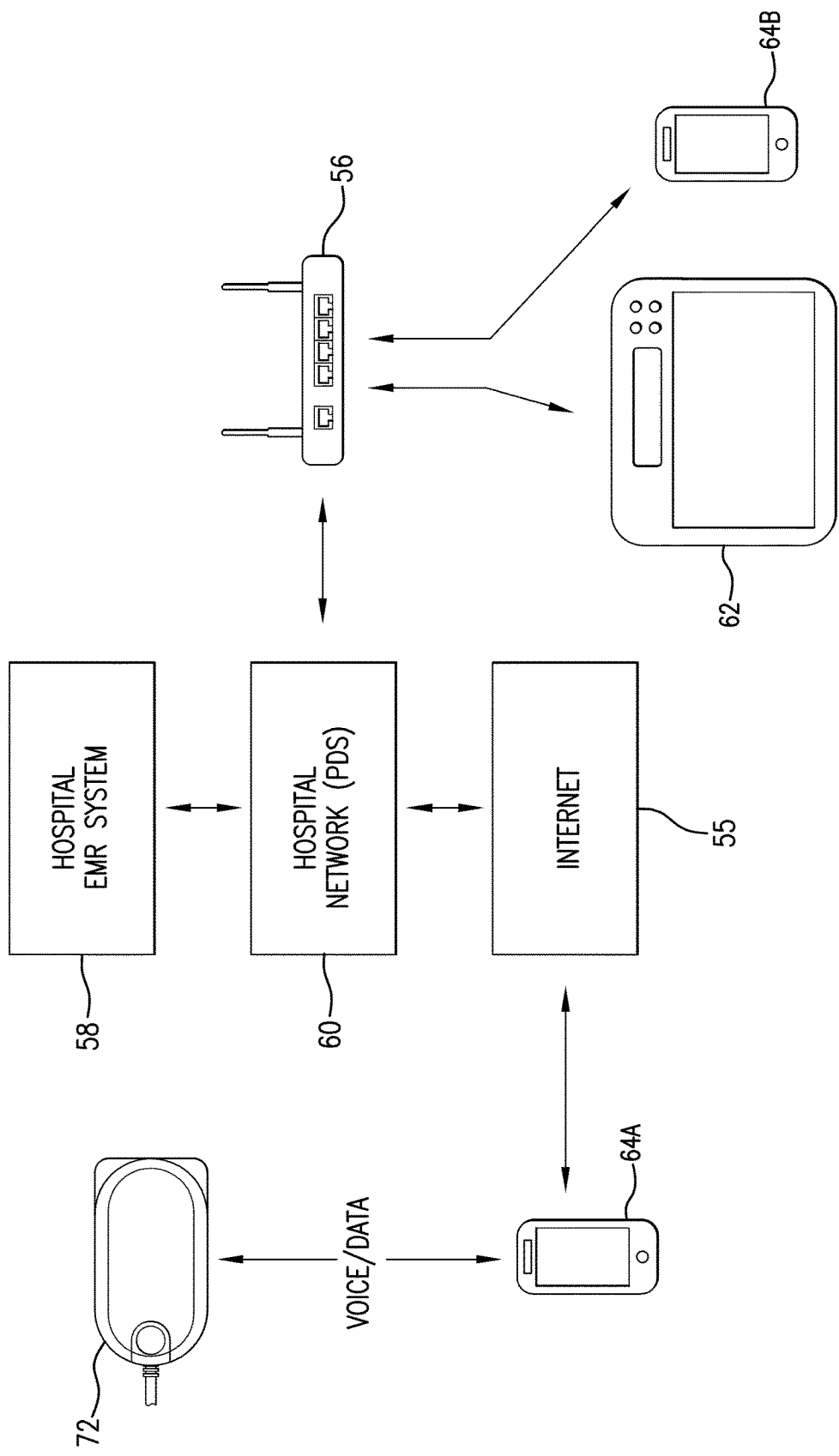
FIG. 27 shows an alternate IT configuration of the invention where the wrist-worn transceiver of FIG. 1 communicates with the PDS through a wireless device connected to the Internet.

In an alternate embodiment, as shown in FIG. 27, the first wireless access point 56A shown in FIG. 26 is replaced by a wireless modem 64A, such as a cellular telephone or personal digital assistant. Here, the wireless modem 64A receives voice and data information from the transceiver through a peer-to-peer wireless interface (e.g. an interface based on 802.11b/g or 802.15.4). The wireless modem 64A then transmits the voice and data information to the Internet 55 using, e.g., a cellular connection, such as one based on GSM or CDMA. In yet another embodiment, as shown in FIG. 28, the transceiver 72 includes an internal long-range wireless transmitter based on a cellular protocol (e.g. GSM or CDMA), allowing it to transmit voice and data information directly to the Internet 55. In the embodiments shown in both FIGS. 27 and 28, information sent through the Internet is ultimately received by the PDS 60, and is sent from there through a wireless access point 56 to either the remote computer 62 or portable device 64.

In embodiments, the transceiver 72 features multiple wireless transmitters, and can operate in multiple modes, such as each of those shown in FIGS. 26-28. In this case the wireless protocol (based on, e.g. 802.11 or cellular) is manually selected using the GUI, or automatically selected based on the strength of the ambient wireless signal.

Other Embodiments of the Invention

In addition to those methods described above, the body-worn monitor can use a number of additional methods to calculate blood pressure and other properties from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) BILATERAL DEVICE, SYSTEM AND METHOD FOR MONITORING VITAL SIGNS (U.S. Ser. No. 11/420,774; filed May 27, 2006); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS, DIA, and MAP for the above-described algorithms. Additionally, processing units and probes for measuring pulse oximetry similar to those described above can be modified and worn on other portions of the patient's body. For example, optical sensors with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area.

Further embodiments of the invention are within the scope of the following claims:

What is claimed is:

1. A vital sign monitoring system configured to be worn on the patient's body and comprising:
 a least one vital sign sensor configured to generate and transmit a time-dependent vital sign waveform; and
 a vital sign monitor configured to be worn on the wrist of the patient and comprising:
  a housing,
  a motion sensor within the housing configured to measure a time-dependent motion waveform,
  a display device on a surface of the housing, and
  a processing component within the housing comprising a microprocessor, wherein the microprocessor comprises a first interface operably connected to the vital sign sensor to receive the time-dependent vital sign waveform, a second interface operably connected to the motion sensor to receive the time-dependent motion waveform, and a third interface operably connected to the display device,
  wherein the microprocessor is configured to (i) collectively process the time-dependent motion waveform and the time-dependent vital sign waveform, (ii) determine using the time-dependent motion waveform an orientation of the vital sign monitor and in response control an orientation of a graphical user interface displayed on the display device, wherein the orientation of the graphical user interface comprises a first orientation directed towards the patient and a second orientation directed away from the patient, and wherein the graphical user interface displays different information in the first orientation as compared to that displayed in the second orientation, (iii) determine using the time-dependent motion waveform a degree of motion of the patient's wrist, (iv) determine using the time-dependent vital sign waveform and the degree of motion of the patient's wrist a vital sign value, and (v) display the vital sign value or a parameter calculated therefrom on the display device through the third interface.

2. The vital sign monitor of claim 1, wherein the first orientation is rotated from the second orientation by 180 degrees.

3. The vital sign monitor of claim 1, wherein the first orientation is rotated from the second orientation by 90 degrees.

4. The vital sign monitor of claim 1, wherein the microprocessor is further configured to render a first graphical user interface on the display device in a first display mode and a second graphical user interface on the display device in a second display mode, wherein the second display mode is accessed by entry of unlocking data into the vital sign monitor.

5. The vital sign monitor of claim 1, wherein the time dependent vital sign waveform is one of a photoplethysmograph, echocardiogram, impedance pneumography, oscillometeric, or accelerometer waveform.

6. The vital sign monitor of claim 1, wherein the parameter calculated from the vital sign signal is one of heart rate, systolic blood pressure, continuous non-invasive blood pressure, diasolic blood pressure, mean arterial pressure, blood oxygen saturation, or respiration rate.

7. The vital sign monitor of claim 1, wherein the motion sensor is an accelerometer.

8. The vital sign monitor of claim 7, wherein the motion signal is a time-dependent waveform measured along the x, y, and z-axes corresponding to an orientation of the accelerometer.

9. The vital sign monitor of claim 1, wherein the motion sensor is one of a tilt switch or a mercury switch.

10. The vital sign monitor of claim 1, wherein the microprocessor is further configured to process the time-dependent motion waveform to determine one of the patient's motion, posture, and arm height.

11. The vital sign monitor of claim 1, wherein the display device is one of an LCD or OLED display.

12. The vital sign monitor of claim 11, wherein the display device comprises a touch panel.

13. The vital sign monitor of claim 1, wherein the vital sign monitor comprises a flexible strap configured to attach the monitor to the patient's wrist.

* * * * *